(12) United States Patent
Ratcliffe et al.

(10) Patent No.: US 8,841,289 B2
(45) Date of Patent: Sep. 23, 2014

(54) HETEROCYCLIC DERIVATIVES

(75) Inventors: Paul David Ratcliffe, Newhouse (GB);
Thomas Russell Clarkson, Newhouse (GB); Fiona Jeremiah, Newhouse (GB);
John Kinnard Ferguson MacLean, Brookline, MA (US)

(73) Assignee: Merck Sharp & Dohme B.V., Rahway, NJ (US)

( * ) Notice: Subject to any disclaimer, the term of this patent is extended or adjusted under 35 U.S.C. 154(b) by 176 days.

(21) Appl. No.: 13/501,587

(22) PCT Filed: Oct. 11, 2010

(86) PCT No.: PCT/EP2010/065160
§ 371 (c)(1),
(2), (4) Date: Apr. 12, 2012

(87) PCT Pub. No.: WO2011/045258
PCT Pub. Date: Apr. 21, 2011

(65) Prior Publication Data
US 2012/0208796 A1     Aug. 16, 2012

Related U.S. Application Data

(60) Provisional application No. 61/251,101, filed on Oct. 13, 2009.

(30) Foreign Application Priority Data

Oct. 13, 2009    (EP) ..................... 09172872

(51) Int. Cl.
*C07D 487/08*    (2006.01)
*C07D 519/00*    (2006.01)
*C07D 471/08*    (2006.01)
*A61K 31/551*    (2006.01)
*A61K 31/517*    (2006.01)
*A61K 31/55*     (2006.01)

(52) U.S. Cl.
USPC ...... 514/214.03; 514/249; 514/221; 540/556; 540/582; 544/287

(58) Field of Classification Search
USPC .............. 544/287; 540/556, 582; 514/214.03, 514/249, 221
See application file for complete search history.

(56) References Cited

FOREIGN PATENT DOCUMENTS

| WO | 03/062235 A1 | 7/2003 |
| WO | 2008/033764 A2 | 3/2008 |
| WO | 2008/077555 A2 | 7/2008 |
| WO | 2009/017236 A1 | 5/2009 |

*Primary Examiner* — Kahsay Habte
(74) *Attorney, Agent, or Firm* — Keith D. MacMillan; John C. Todaro

(57) ABSTRACT

The present invention relates to a heterocyclic derivative of formula (I) wherein the variables are as defined in the specification or to a pharmaceutically acceptable salt or solvate thereof. The present invention further relates to pharmaceutical compositions comprising said heterocyclic derivatives and to their use in therapy, for instance in the treatment or prevention of disorders mediated by nicotinic acetylcholine receptors, such as schizophrenia and Alzheimer's disease.

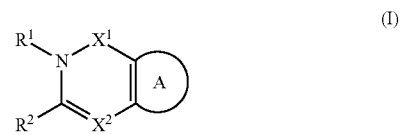

16 Claims, No Drawings

HETEROCYCLIC DERIVATIVES

RELATED APPLICATIONS

This application is a national stage entry under 35 U.S.C. §371 of PCT/EP2010/065160 filed on Oct. 11, 2010 which claims priority to U.S. Application No. 61/251,101 filed on Oct. 13, 2009.

The present invention relates to heterocyclic derivatives, to pharmaceutical compositions comprising these compounds and to their use in therapy, in particular, to their use in the treatment or prevention of diseases or disorders mediated by nicotinic acetylcholine receptors such as schizophrenia or Alzheimer's disease.

Acetylcholine receptors (AChRs) can be divided into two distinct protein families: the metabotrophic muscarinic acetylcholine receptors (mAChRs) and the ionotrophic nicotinic acetylcholine receptors (nAChRs). Both receptors are activated by the endogenous neurotransmitter acetylcholine (ACh). Muscarinic acetylcholine receptors (MAChRs) are G-protein coupled proteins. Nicotinic acetylcholine receptors (nAChRs) are members of the ligand-gated ion channel family. When activated, the conductance of ions across the nicotinic ion channel increases. The nicotinic alpha 7 receptor channel is a homomeric pentamer and is expressed both in the periphery and central nervous system (CNS). The nicotinic alpha 7 receptor channel is expressed in various brain regions and is therefore involved in many important biological processes in the CNS, including learning and memory. Compounds which bind to nicotinic acetylcholine receptors are therefore useful for the treatment of a range of disorders involving reduced cholinergic function such as Alzheimer's disease, cognitive or attention disorders, anxiety, neuroprotection, schizophrenia, analgesia, Tourette's syndrome, Parkinson's disease and immune disorders. For recent reviews on nicotinic acetylcholine receptors and their therapeutic use see D'hoedt and Bertrand in Expert Opin. Ther. Targets (2009), 13(4), 395-411; Cincotta, S. L. et al. in Current Opin. Invest. Drugs (2008), 9, 47-56 and Hashimoto et al. in Current Med. Chem., (2005), 5(3), 171-184.

Nicotinic acetylcholine receptor ligands comprising bridged multicyclic amines are known in the art. For example, WO 01/60821 relates to biarylcarboxamides indicated to be useful in the treatment of a range of disorders involving reduced cholinergic function, such as psychotic and intellectual impairment disorders. WO2004/022556 relates to azabicycloalkyl ethers indicated to be α7 nicotinic acetylcholine receptor agonists and useful in the treatment of psychotic disorders, neurodegenerative disorders and other intellectual impairment disorders.

WO 03/062235 relates to thio-bridged aryl compounds capable of modulating acetylcholine receptors and their use in the treatment of nervous system disorders.

WO 2008/033764 relates to quinazolinone and isoquinolinone acetamide derivatives indicated to be useful for the treatment of disorders or diseases influenced by modulation of the activity of the HPA axis, such as depression and stress related disorders. WO2009/107236 relates to pyridopyrimidin-4-one derivatives indicated to be vasopressin $V_{1b}$ antagonists and their use in therapy.

In a first aspect, the present invention relates to a heterocyclic derivative of formula I

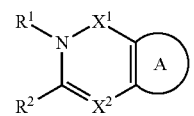

formula I wherein $R^1$ is H, $C_{1-8}$alkyl, $C_{2-8}$alkenyl, $C_{2-8}$alkynyl, $C_{3-8}$cycloalkyl, $C_{3-8}$cycloalkyl$C_{1-2}$alkyl, Z—$C_{1-2}$alkyl or a 4-8 membered heterocyclyl comprising one or more heteroatomic moiety independently selected from O, S, SO and $SO_2$ wherein Z is a 5-6 membered heteroaryl comprising one or more heteroatom independently selected from O, N, and S, said $C_{1-8}$alkyl, $C_{3-8}$cycloalkyl, $C_{3-8}$cycloalkyl$C_{1-2}$alkyl, 5-6 membered heteroaryl and 4-8 membered heterocyclyl being optionally substituted with one or more substituent independently selected from halogen, hydroxyl, $C_{1-6}$alkoxyl, $CONR^3R^4$, $SO_2NR^5R^6$ and $CO_2C_{1-6}$alkyl;

$R^2$ is H, $C_{1-8}$alkyl, $C_{3-8}$cycloalkyl or $C_{3-8}$cycloalkyl$C_{1-2}$alkyl, said $C_{1-8}$alkyl, $C_{3-8}$cycloalkyl and $C_{3-8}$cycloalkyl$C_{1-2}$alkyl being optionally substituted with one or more substituent independently selected from halogen, hydroxyl and methoxy or $R^2$ is $C_{6-10}$aryl optionally substituted with one or more substituent independently selected from halogen, hydroxy, cyano, $C_{1-8}$alkyl, $C_{3-8}$cycloalkyl, $C_{1-6}$alkyloxy and $C_{3-6}$cycloalkyloxy, said $C_{1-8}$alkyl, $C_{3-8}$cycloalkyl, $C_{1-6}$alkyloxy and $C_{3-6}$cycloalkyloxy being optionally substituted with one or more halogens or $R^2$ is a 5-10 membered heteroaryl ring system comprising a heteroatom selected from N, O and S and optionally substituted with methyl, $C_{1-6}$alkyloxy, halogen or cyano;

$R^3$ and $R^4$ are independently H or $C_{1-6}$alkyl or $R^3$ and $R^4$ together with the N to which they are bonded form a 4-7 membered heterocyclic ring optionally comprising a further heteroatomic moiety selected from O, S, SO and $SO_2$, said $C_{1-6}$alkyl and 4-7 membered heterocyclic ring being optionally substituted with one or more halogens;

$R^5$ and $R^6$ are independently H or $C_{1-6}$alkyl or $R^5$ and $R^6$ together with the N to which they are bonded form a 4-7 membered heterocyclic ring optionally comprising a further heteroatomic moiety selected from O, S, SO and $SO_2$, said $C_{1-6}$alkyl and 4-7 membered heterocyclic ring being optionally substituted with one or more halogens;

$X^1$ is CO or $SO_2$;

$X^2$ is N or CH;

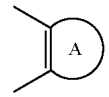

is a substituted arylene or heteroarylene fused to the pyrimidinone at adjacent carbon atoms and is selected from:

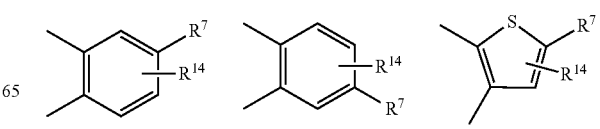

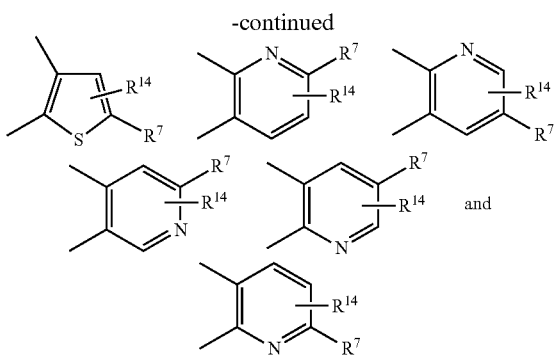

$R^7$ is $(Y)_m R^8$, wherein
Y is O, $NR^9$ or $CR^{10}R^{11}$;
m is 0 or 1;
$R^8$ is a 6-10 membered bridged or fused multicyclic saturated or partially unsaturated ring system comprising a $N(R^{12})_n$ moiety and optionally comprising a $N(R^{13})_p$ moiety, said bridged or fused multicyclic ring system being optionally substituted with methyl or hydroxyl;
$R^9$ is H or $C_{1-6}$alkyl;
$R^{10}$ and $R^{11}$ are independently H or $C_{1-6}$alkyl;
$R^{12}$ and $R^{13}$ are independently H, $C_{1-6}$alkyl or oxo;
$R^{14}$ is a further optional substituent selected from methyl, halogen and cyano;
n is 0 or 1 and
p is 0 or 1
with the proviso that when $R^7$ is 1,4-diazabicyclo[3.2.2]non-4-yl or octahydropyrrolo[1,2-a]pyrazin-2-yl, one or both of $R^3$ and $R^4$ cannot be H.
or a pharmaceutically acceptable salt or solvate thereof.

The term $C_{1-8}$alkyl, as used herein, represents a branched or unbranched alkyl group having 1-8 carbon atoms. Examples of such groups are methyl, ethyl, isopropyl, tertiary butyl and n-heptyl. Similarly the term $C_{1-6}$alkyl, as used herein, represents a branched or unbranched alkyl group having 1-6 carbon atoms. Examples of such groups are methyl, ethyl, isopropyl, tertiary butyl and n-pentyl.

The term $C_{2-8}$alkenyl, as used herein, represents a branched or unbranched alkenyl group having 2-8 carbon atoms and at least one double bond. Examples of such groups are ethenyl, isopropenyl and 2-methylbuten-2-yl.

The term $C_{2-8}$alkynyl, as used herein, represents a branched or unbranched alkynyl group having 2-8 carbon atoms and at least one triple bond. Examples of such groups are ethynyl, propynyl and 3-methylbuten-1-yl.

The term $C_{3-8}$cycloalkyl, as used herein, represents a branched or unbranched cyclic alkyl group having 3-8 carbon atoms. Examples of such groups are cyclopropyl, cyclopentyl and 2-methylcyclohexyl.

The term $C_{3-8}$cycloalkyl$C_{1-2}$alkyl, as used herein, represents a $C_{1-2}$alkyl group which is substituted with a $C_{3-8}$cycloalkyl group. Examples of such groups are cyclopropylmethyl, and 2-cyclobutylethyl.

The term $C_{1-6}$alkyloxy, as used herein, represents a branched or unbranched alkyloxy group having 1-6 carbon atoms. Examples of such groups are $CO_2CH_3$ and $CO_2C_2H_5$.

The term $CO_2C_{1-6}$alkyl, as used herein, represents a carboxylic acid ester formed from an alcohol having 1-6 carbon atoms. Examples of such groups are methoxymethyl, and ethoxyethyl.

The term $C_{6-10}$aryl, as used herein, represents an aromatic group having 6-10 carbon atoms and comprising one ring or two rings fused together, at least one of which must be aromatic. Examples of such groups include phenyl and naphthyl.

The term halogen, as used herein, represents a fluorine, chlorine, bromine or iodine.

The term solvate, as used herein, refers to a complex of variable stoichiometry formed by a solvent and a solute (in this invention, a compound of formula I). Such solvents may not interfere with the biological activity of the solute. Examples of suitable solvents include water, ethanol and acetic acid.

Examples of 4-8 membered heterocyclyl comprising one or more moiety independently selected from O, S, SO and $SO_2$ include tetrahydrofuranyl, tetrahydropyranyl, tetrahydrothienyl and tetrahydrothiopyranyl.

Examples of 5-10 membered heteroaryl ring system comprising a heteroatom selected from N, O and S include furanyl, pyrrolyl, thienyl, imidazolyl, pyrrazolyl, thiazolyl, pyridinyl pyrimidinyl, indolyl, benzthienyl and quinazolinyl. Likewise, examples of 5-6 membered heteroaryl comprising one or more heteroatom independently selected from O, N and S include furanyl, pyrrolyl, thienyl, imidazolyl, pyrrazolyl, thiazolyl, pyridinyl and pyrimidinyl.

Examples of 4-7 membered heterocyclic rings formed by $R^3$ and $R^4$ together with the N to which they are bonded optionally comprising a further heteroatomic moiety selected from O, S, SO and $SO_2$ include azetidine, piperidine, pyrrolidine and morpholine.

Similarly, examples of 4-7 membered heterocyclic rings formed by $R^5$ and $R^6$ together with the N to which they are bonded optionally comprising a further heteroatomic moiety selected from O, S, SO and $SO_2$ include azetidine, piperidine, pyrrolidine and morpholine.

A 6-10 membered bridged multicyclic ring system comprising a $N(R^{12})_n$ moiety and optionally comprising a $N(R^{13})_p$ moiety, as used herein, represents a multicyclic ring system, wherein atoms in one ring having at least one atom between them, are joined together with further atoms to form an additional ring thereby bridging over the first ring.

Examples of 6-10 membered bridged multicyclic saturated ring systems comprising a $N(R^{12})_n$ moiety and optionally comprising a $N(R^{13})_p$ moiety include:

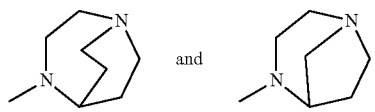

Examples of 6-10 membered bridged multicyclic, partially unsaturated, ring systems comprising a $N(R^{12})_n$ moiety and optionally comprising a $N(R^{13})_p$ moiety include:

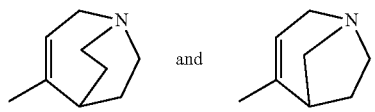

A 6-10 membered fused multicyclic ring system comprising a $N(R^{12})_n$ moiety and optionally comprising a $N(R^{13})_p$ moiety, as used herein, represents a multicyclic ring system, wherein adjacent atoms in one ring are joined together with further atoms to form an additional ring.

Examples of 6-10 membered fused multicyclic saturated ring systems comprising a $N(R^{12})_n$ moiety and optionally comprising a $N(R^{13})_p$ moiety include:

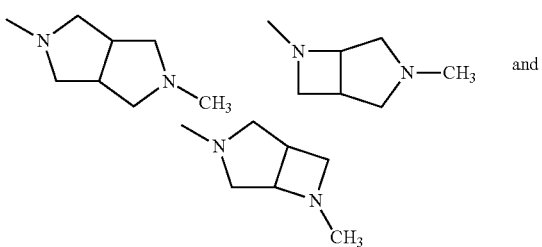

Examples of 6-10 membered fused multicyclic partially unsaturated ring systems comprising a N(R$^{12}$)$_n$ moiety and optionally comprising a N(R$^{13}$)$_p$ moiety include:

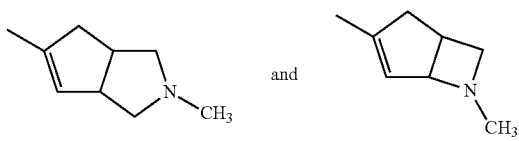

The skilled person will appreciate that when

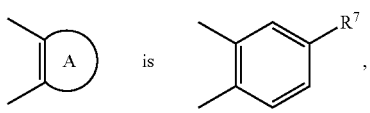

the compound of formula I is,

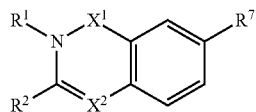

Similarly, the skilled person will appreciate that when

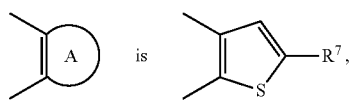

the compound of formula I is

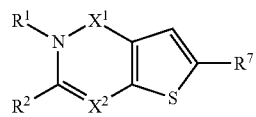

and when

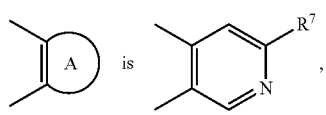

the compound of formula I is

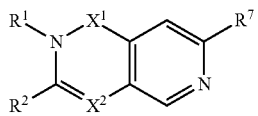

In one embodiment of the present invention R$^1$ is H or C$_{1-8}$alkyl optionally substituted with halogen, hydroxyl, C$_{1-6}$alkoxyl, CONR$^3$R$^4$ or SO$_2$NR$^5$R$^6$, wherein R$^3$-R$^6$ have the previously defined meanings. In another embodiment, R$^1$ is H or C$_{1-4}$alkyl optionally substituted with halogen, hydroxyl, C$_{1-6}$alkoxyl, CONR$^3$R$^4$ or SO$_2$NR$^5$R$^6$, wherein R$^3$-R$^6$ have the previously defined meanings. In a further embodiment, R$^1$ is H, methyl, ethyl, propyl or isopropyl, optionally substituted with halogen, hydroxyl, C$_{1-6}$alkoxyl, CONR$^3$R$^4$ or SO$_2$NR$^5$R$^6$, wherein R$^3$-R$^6$ have the previously defined meanings. In a further embodiment, R$^1$ is H, methyl, ethyl, propyl or isopropyl, optionally substituted with halogen, methoxyl, hydroxyl, CO$_2$CH$_3$ or CON(CH$_3$)$_2$. In a further embodiment, R$^1$ is H, methyl, ethyl, propyl or isopropyl, optionally substituted with methoxyl or hydroxyl. In a still further embodiment, R$^1$ is H or methyl.

In another embodiment of the present invention R$^1$ is C$_{3-8}$cycloalkyl or C$_{3-8}$cycloalkylC$_{1-2}$alkyl, said C$_{3-8}$cycloalkyl and C$_{3-8}$cycloalkylC$_{1-2}$alkyl being optionally substituted with halogen, hydroxyl, C$_{1-6}$alkoxyl, CONR$^3$R$^4$ or SO$_2$NR$^5$R$^6$, wherein R$^3$-R$^6$ have the previously defined meanings. In another embodiment, R$^1$ is C$_{3-8}$cycloalkyl or C$_{3-8}$cycloalkylC$_{1-2}$alkyl, said C$_{3-8}$cycloalkyl and C$_{3-8}$cycloalkylC$_{1-2}$alkyl being optionally substituted with hydroxyl or methoxyl. In another embodiment, R$^1$ is cyclopropyl, cyclobutyl, cyclopropylmethyl or cyclobutylmethyl, said cyclopropyl, cyclobutyl, cyclopropylmethyl and cyclobutylmethyl being optionally substituted with hydroxyl or methoxyl. In a further embodiment, R$^1$ is cyclopropyl or cyclobutyl, optionally substituted with hydroxyl or methoxyl.

In a further embodiment of the present invention, R$^1$ is a 4-8 membered heterocyclyl comprising one or more heteroatomic moiety independently selected from O, S, SO and SO$_2$, said 4-8 membered heterocyclyl being optionally substituted with halogen, hydroxyl, C$_{1-6}$alkyl or C$_{1-6}$alkoxyl. In a further embodiment, R$^1$ is a 4-6 membered heterocyclyl comprising one or more heteroatomic moiety independently selected from O, S, SO and SO$_2$, said 4-6 membered heterocyclyl being optionally substituted with halogen, hydroxyl, C$_{1-6}$alkyl or C$_{1-6}$alkoxyl. In a further embodiment, R$^1$ is a 4-6 membered heterocyclyl comprising O, S, SO or SO$_2$, said 4-8 membered heterocyclyl being optionally substituted with hydroxyl or methyl.

In a further embodiment of the present invention, R$^1$ is Z—C$_{1-2}$alkyl, wherein Z is a 5-6 membered heteroaryl comprising one or more heteroatom independently selected from O, S and N said 5-6 membered heteroaryl being optionally substituted with halogen, hydroxyl, C$_{1-6}$alkyl or C$_{1-6}$alkoxyl. In a further embodiment, R$^1$ is Z—CH$_2$, wherein Z is a 5-6 membered heteroaryl comprising one or more heteroatom independently selected from O, S and N said 5-6 membered heteroaryl being optionally substituted with halogen, methyl or methoxyl.

In one embodiment of the present invention R$^2$ is H, C$_{1-8}$alkyl, C$_{3-8}$cycloalkyl or C$_{3-8}$cycloalkylC$_{1-2}$alkyl, said C$_{1-8}$alkyl, C$_{3-8}$cycloalkyl and C$_{3-8}$cycloalkylC$_{1-2}$alkyl being optionally substituted with one or more halogen. In a further embodiment, R$^2$ is H, C$_{1-4}$alkyl or C$_{3-6}$cycloalkyl. In a further embodiment, $R^2$ is H, methyl, ethyl, isopropyl or t-butyl. In a still further embodiment, $R^2$ is cyclopropyl, cyclobutyl, cyclopentyl or cyclohexyl.

In another embodiment of the present invention, $R^2$ is $C_{6-10}$aryl optionally substituted with one or more substituent independently selected from halogen, hydroxy, cyano, $C_{1-8}$alkyl, $C_{3-8}$cycloalkyl, $C_{1-6}$alkyloxy and $C_{3-6}$cycloalkyloxy, said $C_{1-8}$alkyl, $C_{3-8}$cycloalkyl, $C_{1-6}$alkyloxy and $C_{3-6}$cycloalkyloxy being optionally substituted with one or more halogens. In a further embodiment, $R^2$ is phenyl optionally substituted with one or more substituent independently selected from halogen, hydroxy, cyano, $C_{1-8}$alkyl, $C_{3-8}$cycloalkyl, $C_{1-6}$alkyloxy and $C_{3-6}$cycloalkyloxy, said $C_{1-8}$alkyl, $C_{3-8}$cycloalkyl, $C_{1-6}$alkyloxy and $C_{3-6}$cycloalkyloxy being optionally substituted with one or more halogens. In a still further embodiment, $R^2$ is phenyl optionally substituted with one or two substituents selected from chloro, fluoro, methyl, methoxyl and cyano.

In another embodiment of the present invention, $R^2$ is a 5-10 membered heteroaryl system comprising a heteroatom selected from N, O and S and optionally substituted with methyl, $C_{1-6}$alkyloxy or halogen. In a further embodiment, $R^2$ is a heteroaryl selected from pyridyl, thienyl, pyrrolyl, furanyl, imidazolyl, thiazolyl and pyrazolyl, said heteroaryl being optionally substituted with methyl, $C_{1-6}$alkyloxy or halogen. In a still further embodiment, $R^2$ is pyridyl, thiazolyl or furanyl, said pyridyl, thiazolyl and furanyl being optionally substituted with methyl or halogen.

In one embodiment of the present invention,

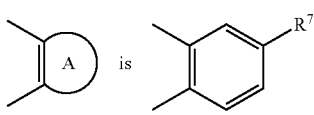

In a further embodiment of the present invention,

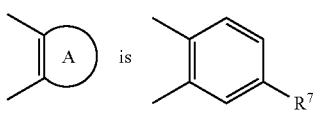

In a further embodiment of the present invention,

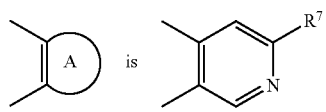

In one embodiment of the present invention, $R^7$ is

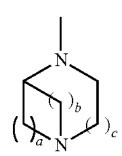

wherein a, b and c are independently 1 or 2.

In another embodiment of the present invention, $R^7$ is selected from:

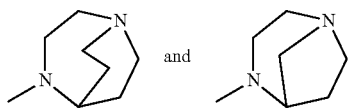

In another embodiment of the present invention, $R^7$ is

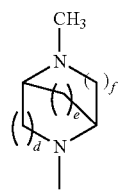

wherein d, e and f are independently 1 or 2.

In another embodiment of the present invention, $R^7$ is:

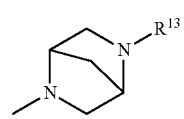

wherein $R^{13}$ has the previously defined meanings.

In another embodiment of the present invention, $R^7$ is

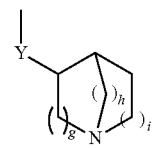

wherein Y is O, CH or N and g, h and i are independently 1 or 2.

In another embodiment of the present invention, Y is O and m is 1;

In another embodiment of the present invention, Y is NH and m is 1;

In another embodiment of the present invention, $R^7$ is selected from:

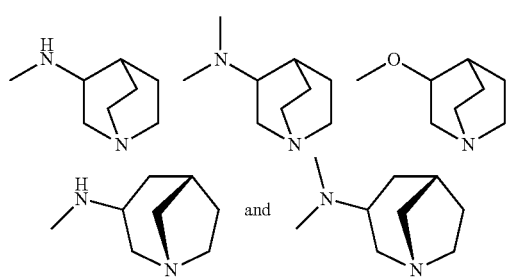

In another embodiment of the present invention, R$^7$ is

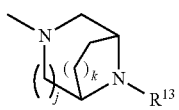

wherein j, and k are independently 1 or 2 and wherein R$^{13}$ has the previously defined meanings.

In another embodiment of the present invention, R$^7$ is:

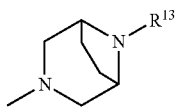

wherein R$^{13}$ has the previously defined meanings.

In another embodiment of the present invention, R$^7$ is:

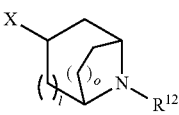

wherein l, and o are independently 1 or 2 and wherein R$^{12}$ has the previously defined meanings.

In another embodiment of the present invention, R$^7$ is selected from:

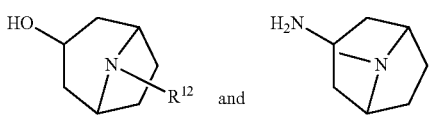

wherein R$^{12}$ has the previously defined meanings.

In another embodiment of the present invention, R$^7$ is

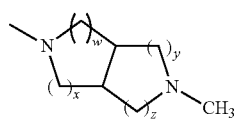

wherein w, x, y and z are independently 1 or 2.

In another embodiment of the present invention, R$^7$ is selected from:

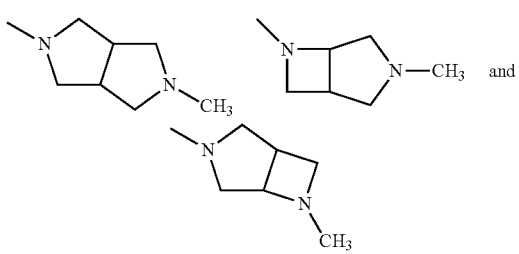

In a further embodiment, R$^8$ is a 6-10 membered saturated bridged tricyclic ring system comprising a N(CH$_3$)$_n$ moiety and optionally comprising a further N(CH$_3$)$_p$ moiety, wherein n and p are independently 0 or 1 and wherein said saturated bridged bicyclic ring system is optionally substituted with methyl or hydroxyl.

In a further embodiment, R$^8$ is a 6-10 membered saturated fused bicyclic ring system comprising a N(CH$_3$)$_n$ moiety and optionally comprising a further N(CH$_3$)$_n$ moiety, wherein n and p are independently 0 or 1 and wherein said saturated bridged bicyclic ring system is optionally substituted with methyl or hydroxyl.

In a further embodiment of the present invention is a heterocyclic derivative of formula II

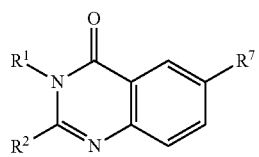

Formula II wherein R$^1$, R$^2$ and R$^7$ have the previously defined meanings.

In a further embodiment of the present invention is a heterocyclic derivative of formula III

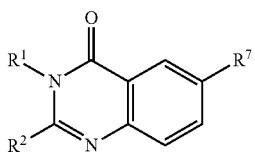

Formula III wherein,

R$^1$ is H, methyl, ethyl, propyl or isopropyl, optionally substituted with hydroxyl or methoxyl;

R$^2$ is H, methyl, ethyl, isopropyl, t-butyl, cyclopropyl, cyclobutyl, cyclopentyl or cyclohexyl or R$^2$ is phenyl optionally substituted with one or two substituents selected from chloro, fluoro, methyl, methoxyl and cyano or R$^2$ is pyridyl, thiazolyl or furanyl, said pyridyl, thiazolyl and furanyl being optionally substituted with methyl or halogen and R$^7$ is

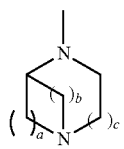

wherein a, b and c are independently 1 or 2 or a pharmaceutically acceptable salt or solvate thereof.

In a still further embodiment of the present invention is a heterocyclic derivative of formula IV

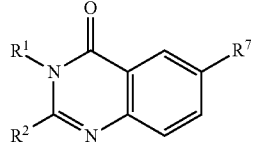

Formula IV wherein,

R¹ is H, methyl, ethyl, propyl or isopropyl, optionally substituted with hydroxyl or methoxyl;

R² is H, methyl, ethyl, isopropyl, t-butyl, cyclopropyl, cyclobutyl, cyclopentyl or cyclohexyl or R² is phenyl optionally substituted with one or two substituents selected from chloro, fluoro, methyl, methoxyl and cyano or R² is pyridyl, thiazolyl or furanyl, said pyridyl, thiazolyl and furanyl being optionally substituted with methyl or halogen and R⁷ is

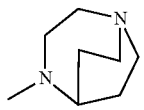

or a pharmaceutically acceptable salt or solvate thereof.

In a still further embodiment of the present invention is a heterocyclic derivative of formula V

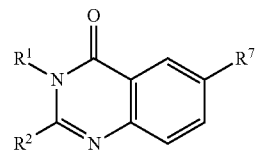

Formula V wherein,

R¹ is H or methyl;

R² is phenyl optionally substituted with one or two substituents selected from chloro, fluoro, methyl, methoxyl and cyano or R² is pyridyl, thiazolyl or furanyl, said pyridyl, thiazolyl and furanyl being optionally substituted with methyl or halogen and R⁷ is

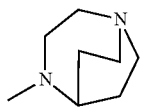

or a pharmaceutically acceptable salt or solvate thereof.

In a still further embodiment of the present invention is a heterocyclic derivative of formula VI

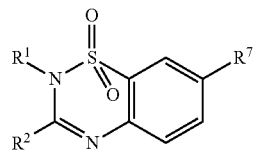

Formula VI wherein,

R¹ is H or methyl;

R² is phenyl optionally substituted with one or two substituents selected from chloro, fluoro, methyl, methoxyl and cyano or R² is pyridyl, thiazolyl or furanyl, said pyridyl, thiazolyl and furanyl being optionally substituted with methyl or halogen and R⁷ is

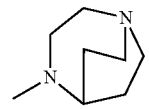

or a pharmaceutically acceptable salt or solvate thereof.

In a still further embodiment of the present invention is a heterocyclic derivative of formula VII

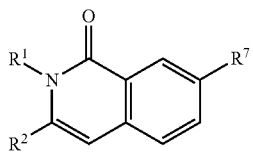

Formula VII wherein,

R¹ is H or methyl;

R² is phenyl optionally substituted with one or two substituents selected from chloro, fluoro, methyl, methoxyl and cyano or R² is pyridyl, thiazolyl or furanyl, said pyridyl, thiazolyl and furanyl being optionally substituted with methyl or halogen and R⁷ is

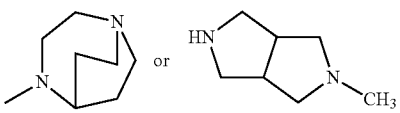

or a pharmaceutically acceptable salt or solvate thereof.

In another embodiment of the present invention is a heterocyclic derivative selected from:

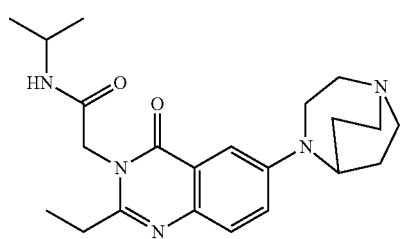
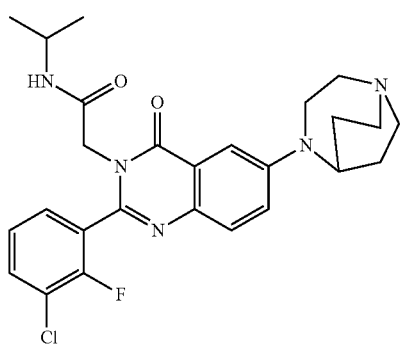
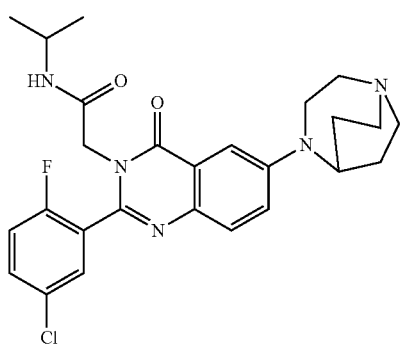
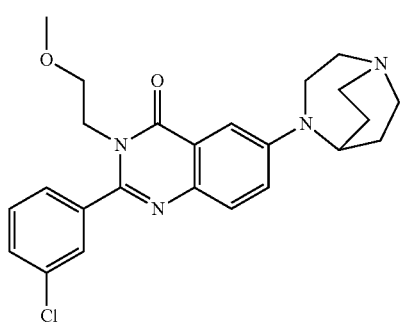
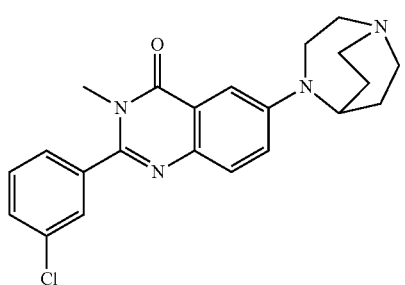
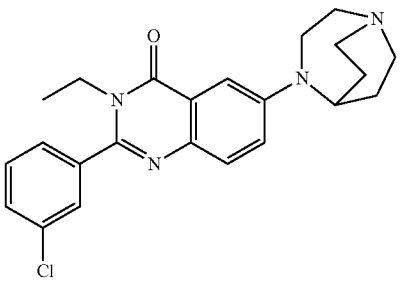
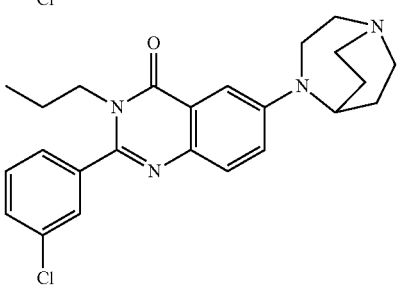
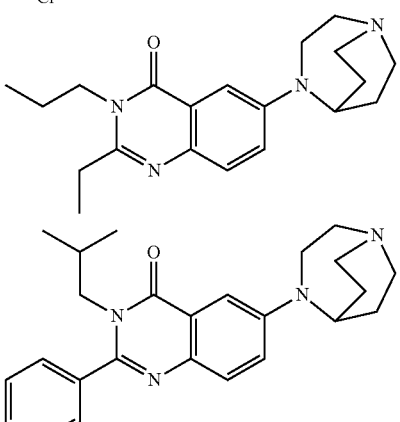
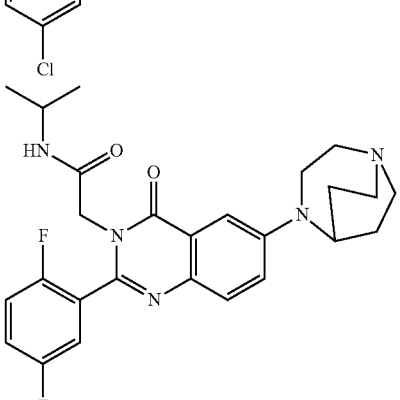
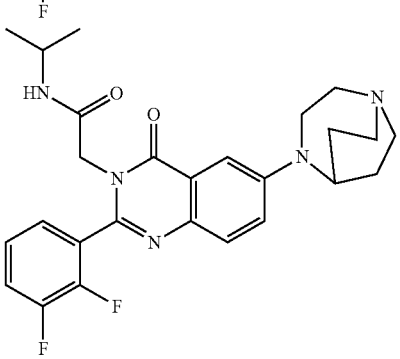

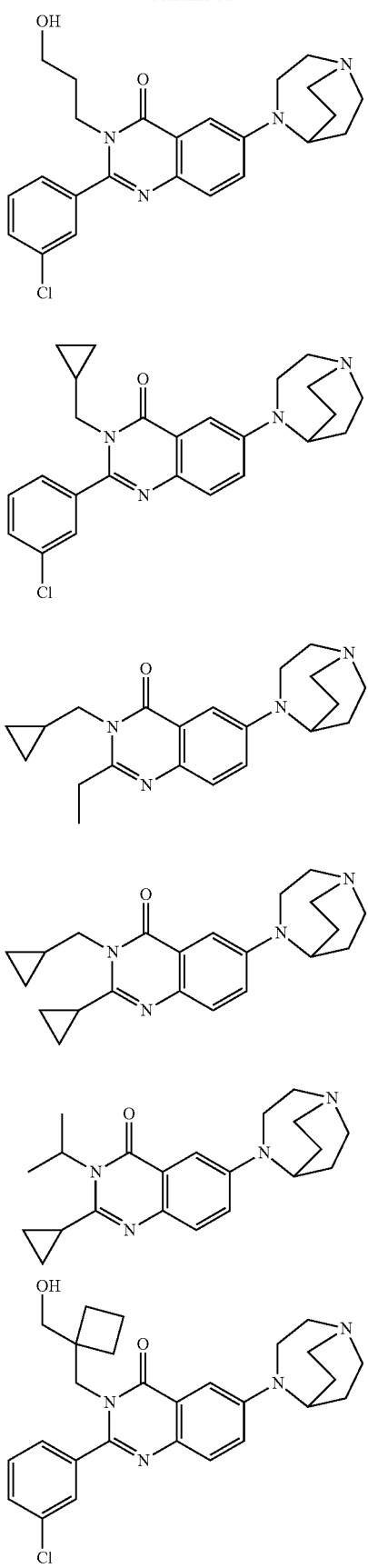
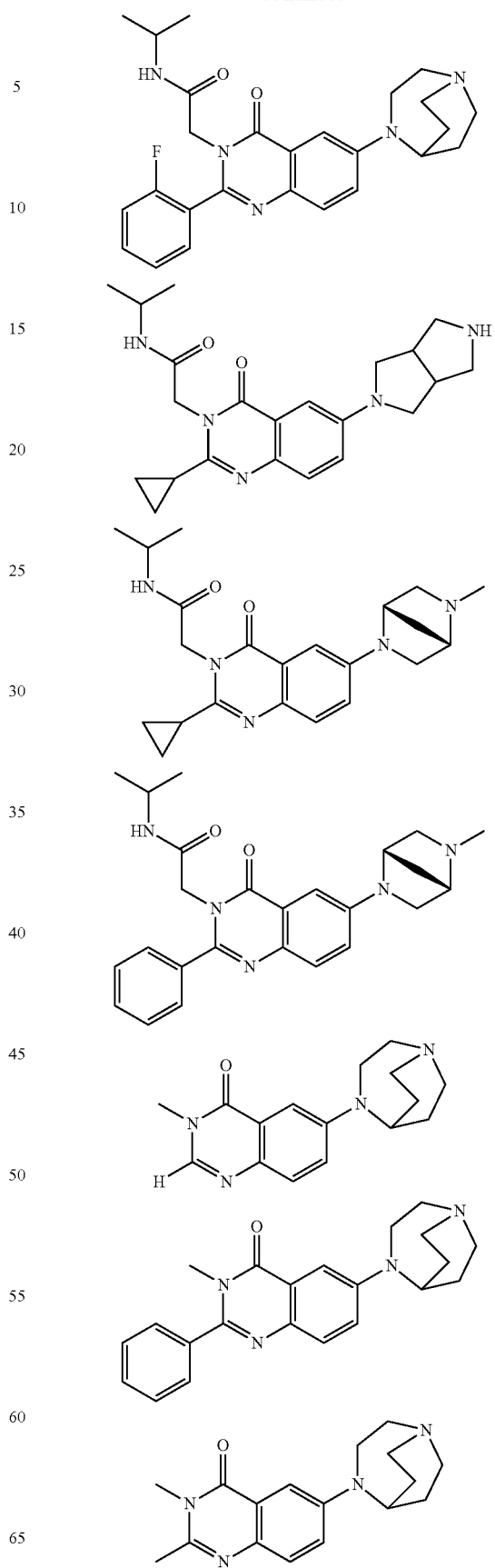

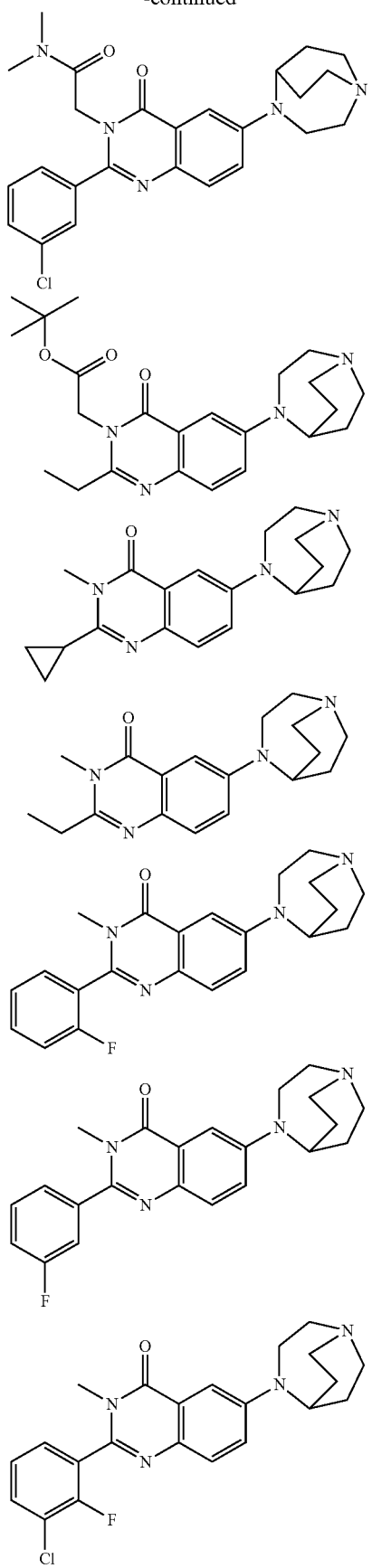
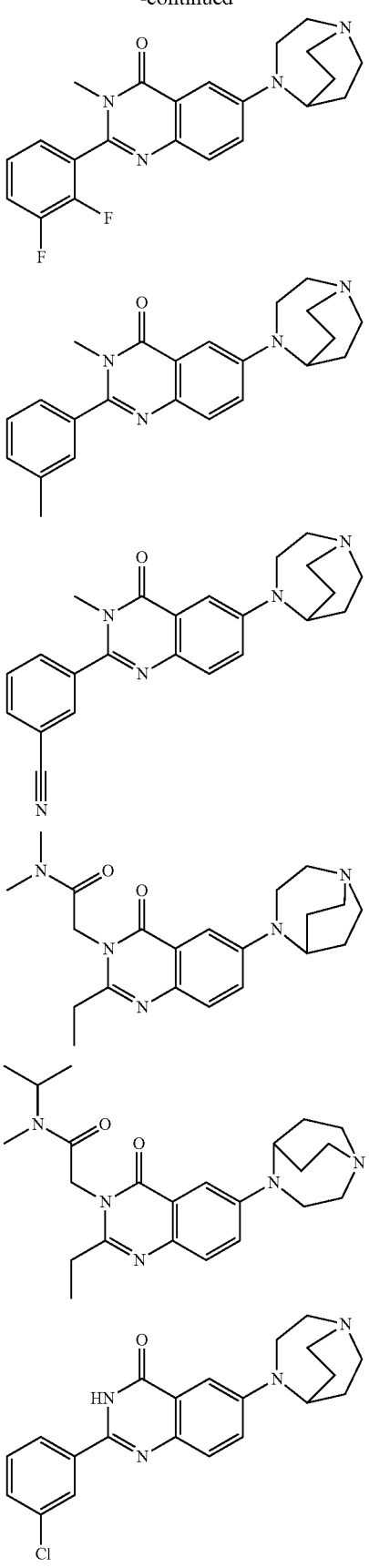

-continued
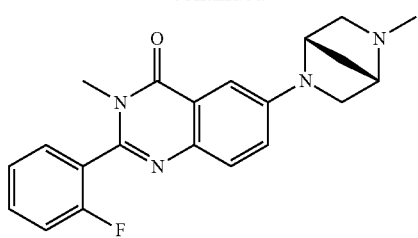
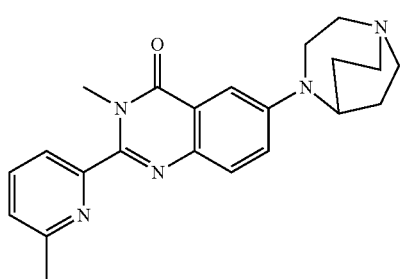
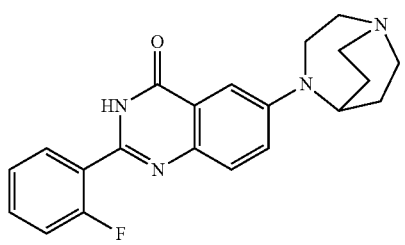
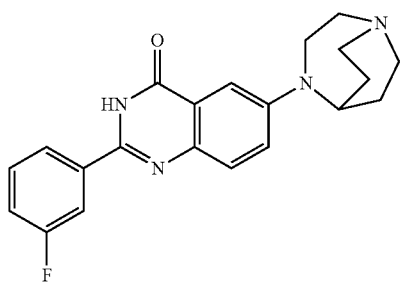
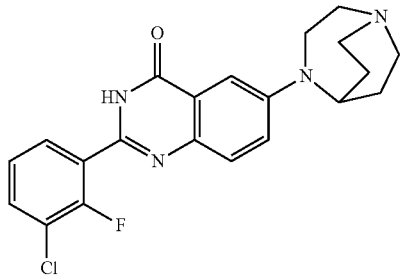
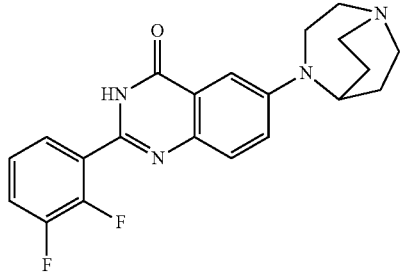
-continued
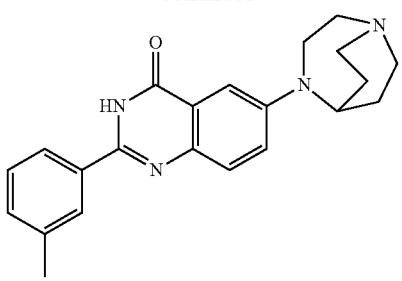
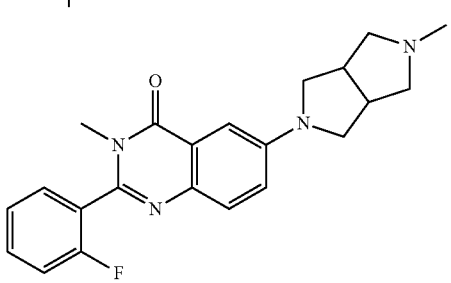
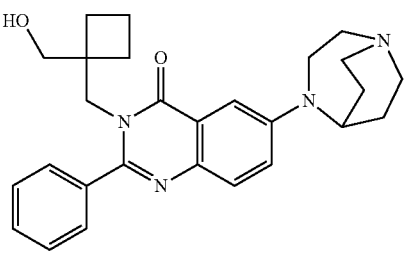
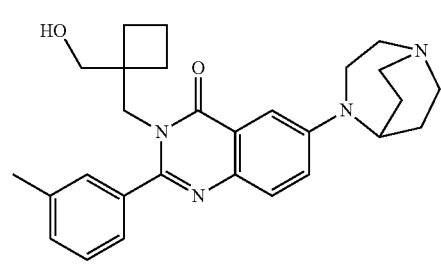
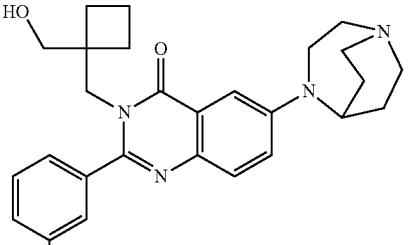
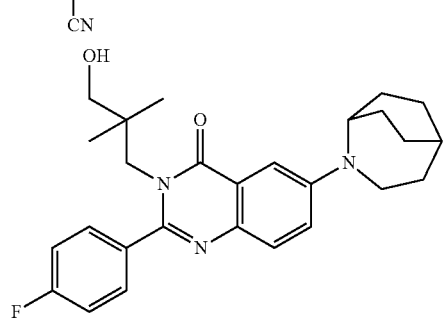

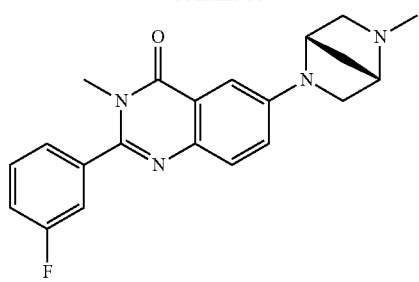
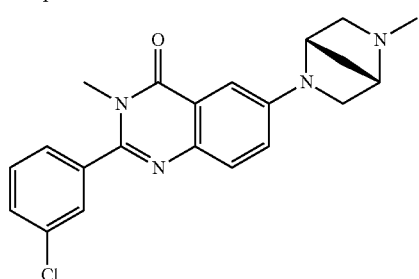
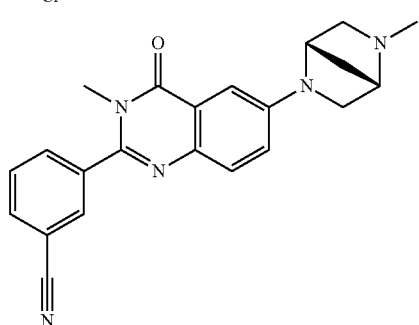
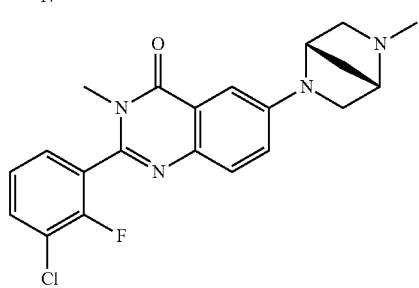
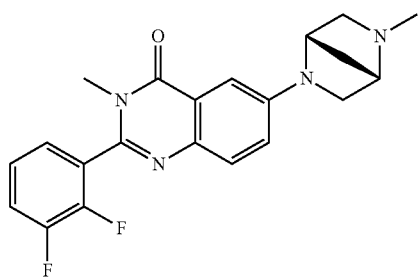
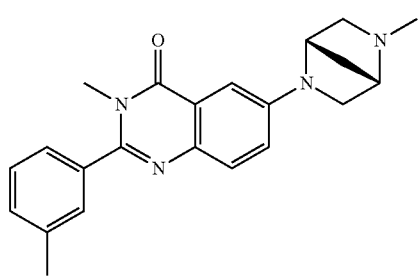
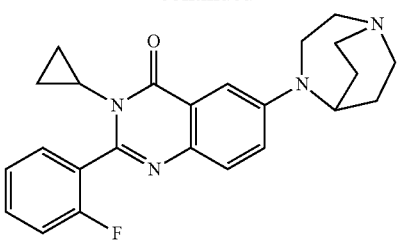
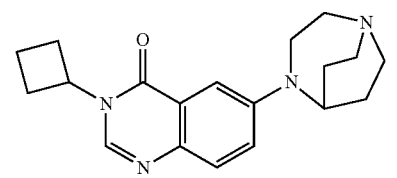
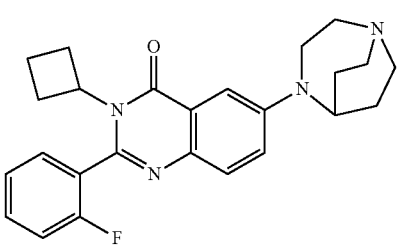
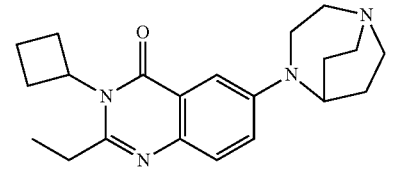
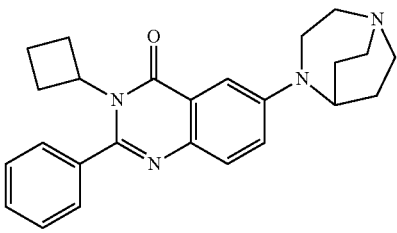
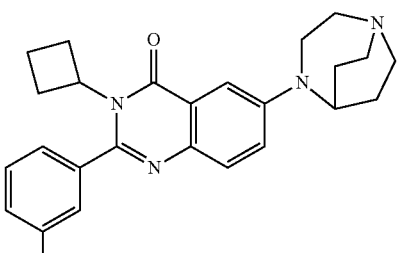
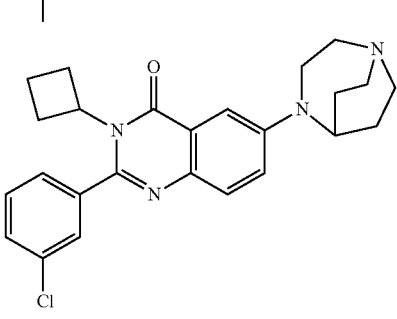

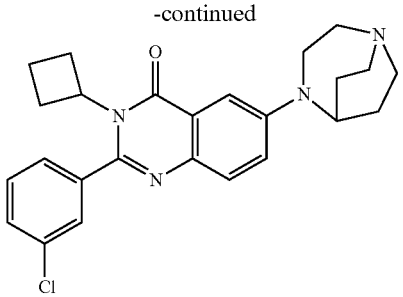
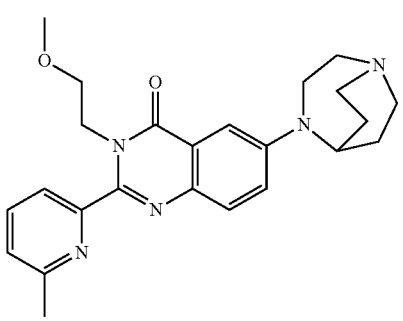
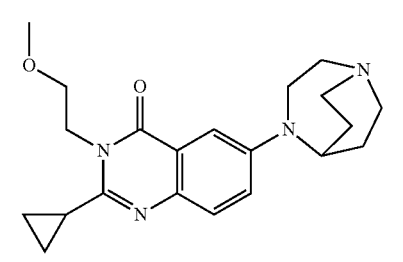
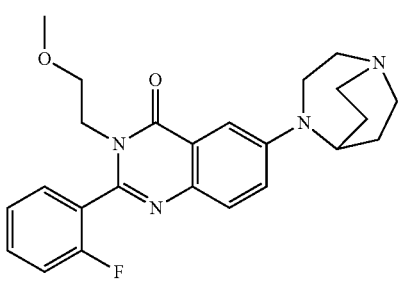
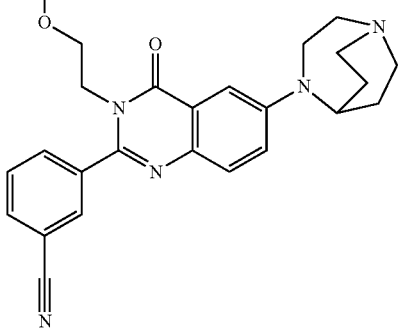
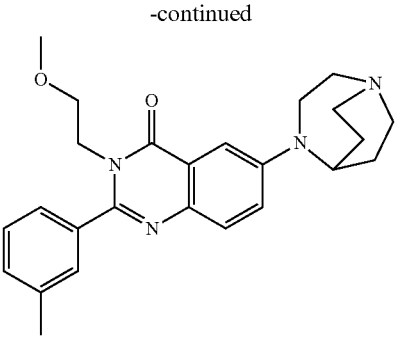
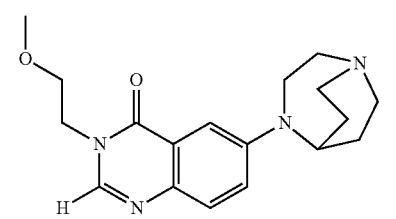
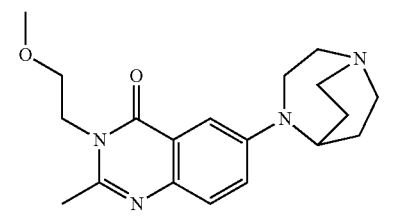
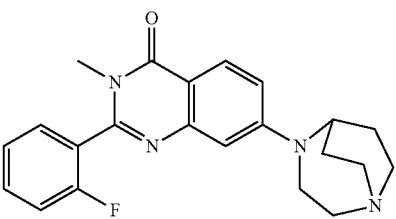
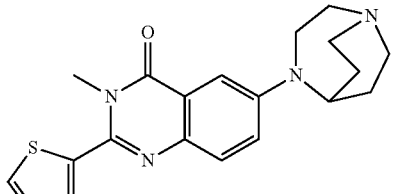
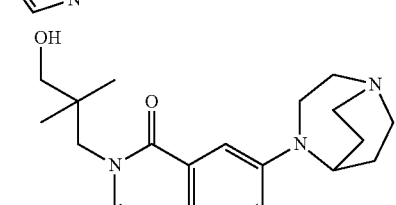
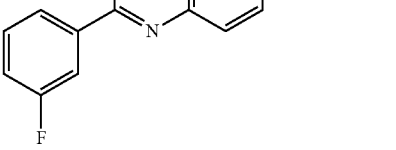

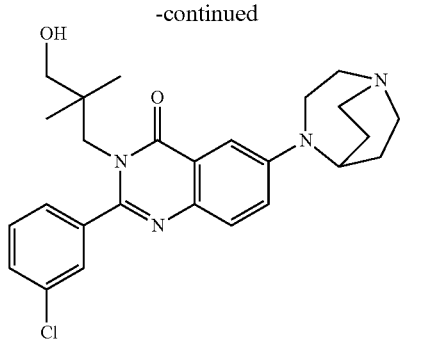
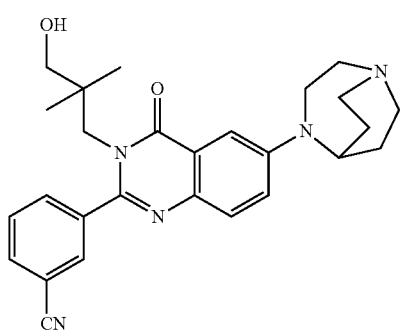
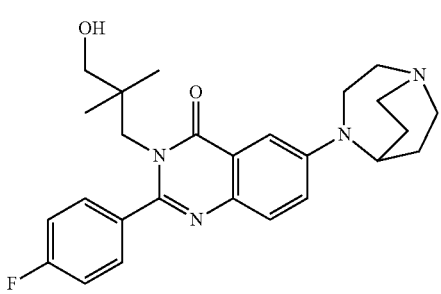
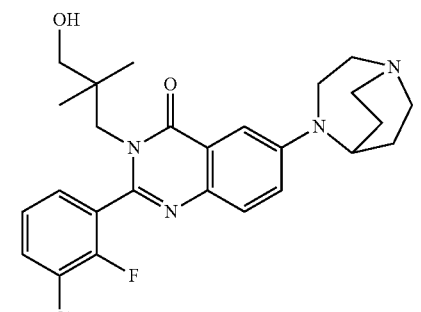
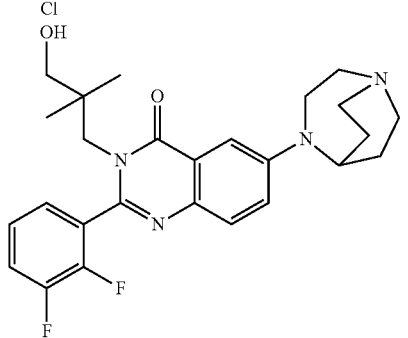
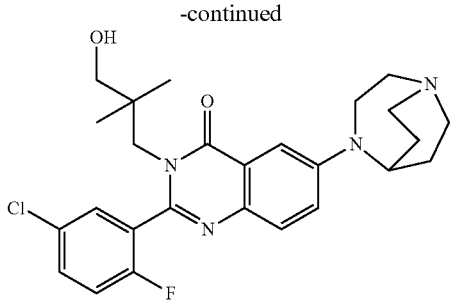
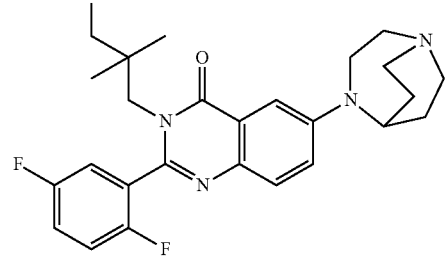
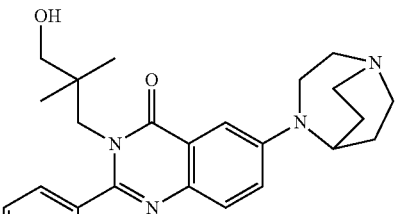
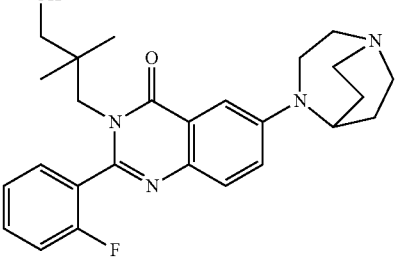
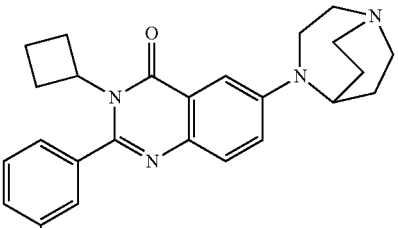
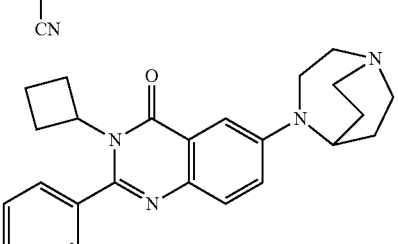

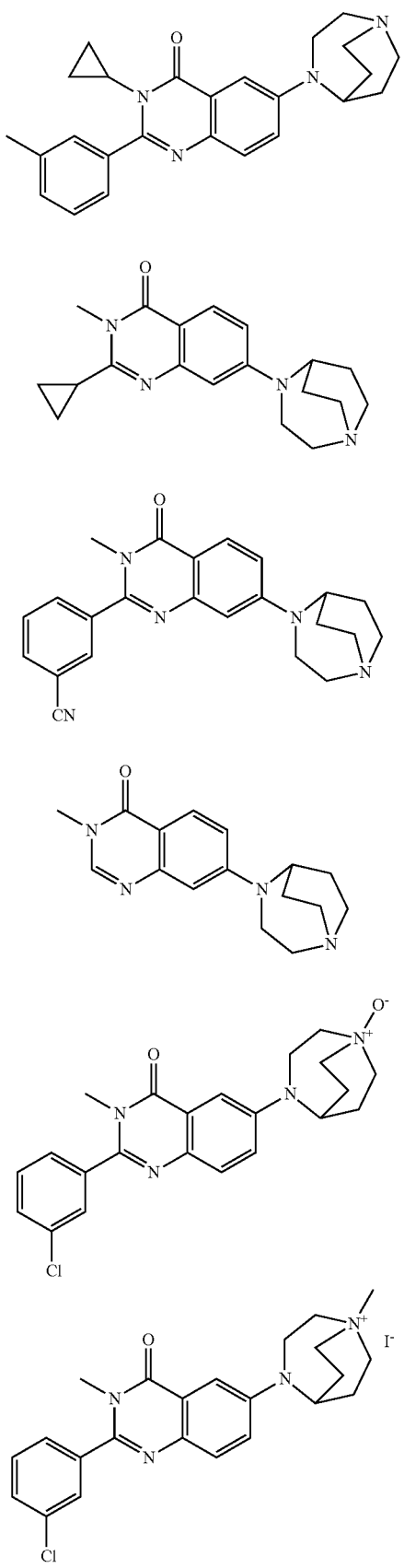
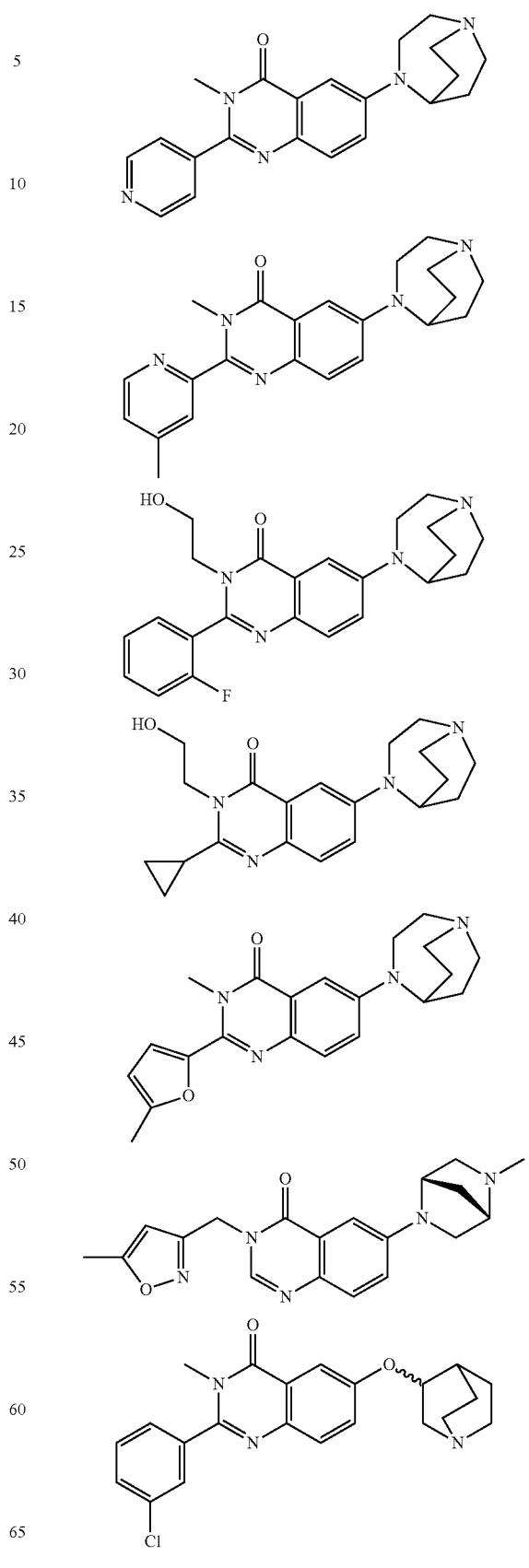

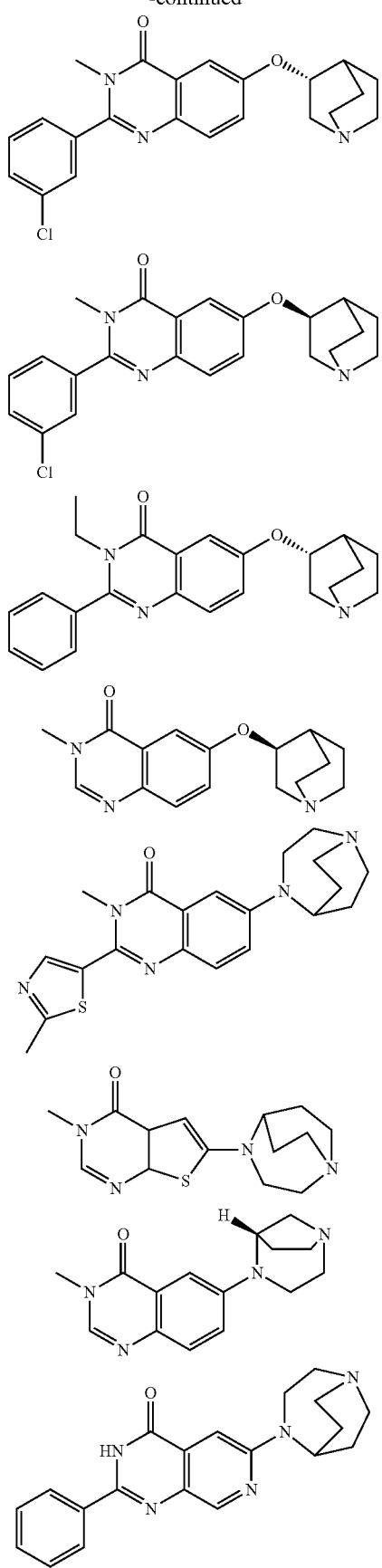
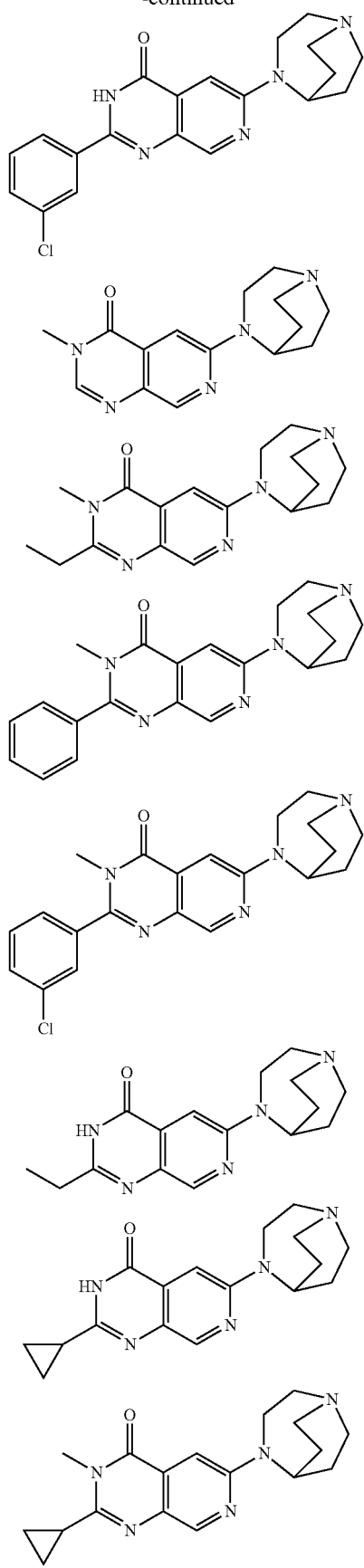

31
-continued
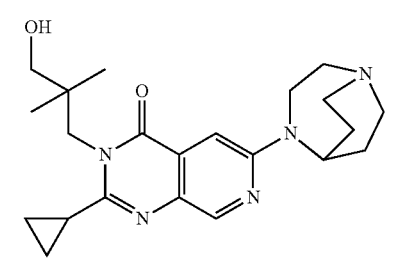
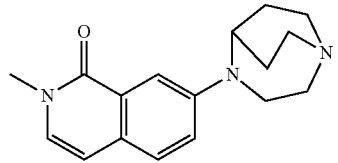
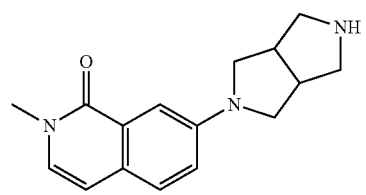
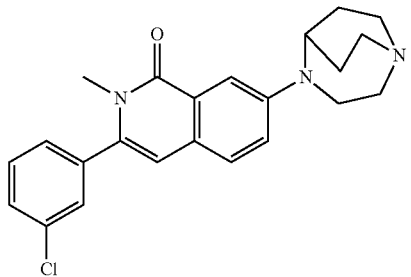
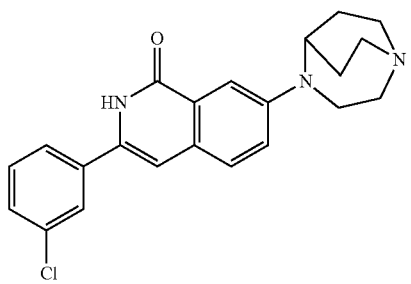
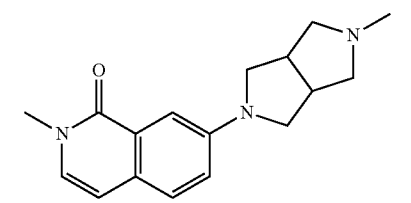
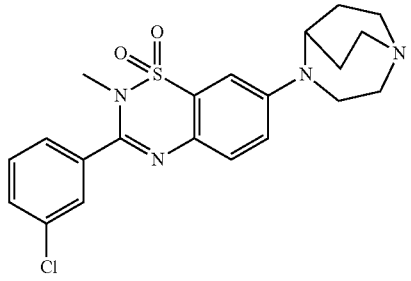
32
-continued
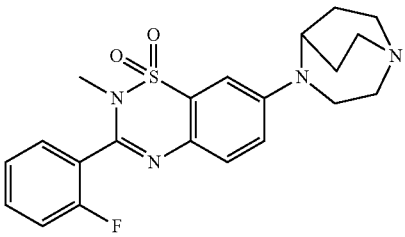
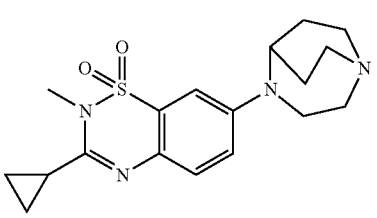
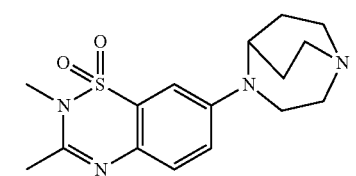
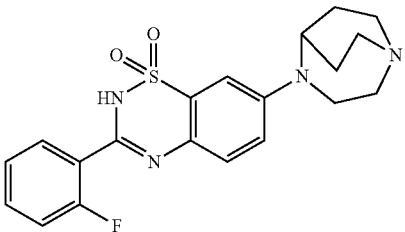
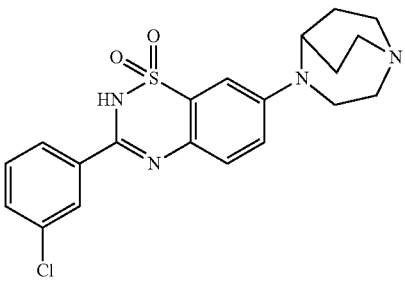
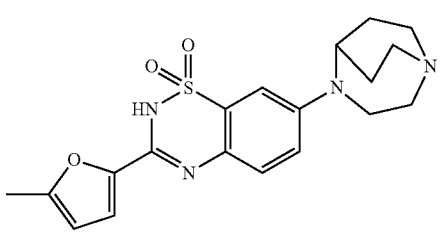

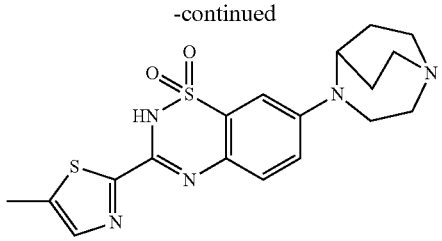

or a pharmaceutically acceptable salt or solvate thereof.

The heterocyclic derivatives of the present invention are prepared by methods well known in the art of organic chemistry. See, for example, J. March, 'Advanced Organic Chemistry' 4th Edition, John Wiley and Sons. During synthetic sequences it may be necessary and/or desirable to protect sensitive or reactive groups on any of the molecules concerned. This is achieved by means of conventional protecting groups, such as those described in T. W. Greene and P. G. M. Wutts 'Protective Groups in Organic Synthesis' 2nd Edition, John Wiley and Sons, 1991. The protective groups are optionally removed at a convenient subsequent stage using methods well known in the art.

formula I

In particular, heterocyclic derivatives of formula I may also be prepared according to the general synthetic sequences presented in WO2008033764 pages 14-20. The skilled person will appreciate that the methods shown can be adapted for the synthesis of analogous derivatives wherein the heteroaryl ring A is a fused thienyl or a fused pyridyl or wherein $X^1$ is a $SO_2$ or wherein $X^2$ is a CH.

The present invention also includes within its scope all stereoisomeric forms of heterocyclic derivatives according to the present invention resulting, for example, because of configurational or geometrical isomerism. Such stereoisomeric forms are enantiomers, diastereoisomers, cis and trans isomers etc. In the case of the individual stereoisomers of heterocyclic derivatives of formula I or salts or solvates thereof, the present invention includes the aforementioned stereoisomers substantially free, i.e., associated with less than 5%, preferably less than 2% and in particular less than 1% of the other stereoisomer. Mixtures of stereoisomers in any proportion, for example a racemic mixture comprising substantially equal amounts of two enantiomers are also included within the scope of the present invention.

For chiral compounds, methods for asymmetric synthesis whereby the pure stereoisomers are obtained are well known in the art, e.g., synthesis with chiral induction, synthesis starting from chiral intermediates, enantioselective enzymatic conversions, separation of stereoisomers using chromatography on chiral media. Such methods are described in *Chirality In Industry* (edited by A. N. Collins, G. N. Sheldrake and J. Crosby, 1992; John Wiley). Likewise methods for synthesis of geometrical isomers are also well known in the art.

The heterocyclic derivatives of the present invention, in the form of a free base, are isolated from reaction mixtures as pharmaceutically acceptable salts. These salts are also obtained by treatment of said free base with an organic or inorganic acid, for example, hydrogen chloride, hydrogen bromide, hydrogen iodide, sulfuric acid, phosphoric acid, acetic acid, trifluoroacetic acid, propionic acid, glycolic acid, maleic acid, malonic acid, methanesulfonic acid, fumaric acid, succinic acid, tartaric acid, citric acid, benzoic acid and ascorbic acid.

The heterocyclic derivatives of the present invention may also exist as amorphous forms. Multiple crystalline forms are also possible. All these physical forms are included within the scope of the present invention.

Preparation of solvates is generally known. Thus, for example, M. Caira et al, *J. Pharmaceutical Sci.*, 93(3), 601-611 (2004) describes the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

The present invention also embraces isotopically labelled compounds of the heterocyclic derivatives described and claimed herein which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically labelled compounds of Formula I (e.g., those labelled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labelled compounds of Formula (I) can generally be prepared by following procedures analogous to those disclosed in the Schemes and/or in the Examples hereinbelow, by substituting an appropriate isotopically labelled reagent for a non-isotopically labelled reagent.

Prodrugs of the heterocyclic derivatives of the invention are also contemplated within the scope of the invention. A prodrug is a compound which acts as a drug precursor which, upon administration to a subject, undergoes conversion by metabolic or other chemical processes to yield a tetracyclic heterocyclic derivative of formula I or a solvate or salt thereof. A discussion of prodrugs and their use is provided in T. Higuchi and V. Stella, *Pro-drugs as Novel Delivery Systems* (1987) 14 of the A.C.S. Symposium Series, and in *Bioreversible Carriers in Drug Design*, Edward B. Roche, ed., American Pharmaceutical Association and Pergamon Press, 1987.

In a further aspect, the heterocyclic derivatives of the present invention and their pharmaceutically acceptable salts and solvates are useful in therapy. As such the heterocyclic derivatives of the present invention are useful for the manufacture of a medicament for the treatment or prevention of disorders mediated by nicotinic acetylcholine receptors, such as Alzheimer's disease, cognitive or attention disorders, anxiety, neuroprotection, schizophrenia, pain, Tourette's syndrome, Parkinson's disease and immune disorders.

The present invention further includes a heterocyclic derivative for use in the treatment of any of the aforementioned diseases or disorders.

The present invention further includes a method for the treatment of a mammal, including a human, suffering from or liable to suffer from any of the aforementioned diseases or disorders, which comprises administering an effective amount of a heterocyclic derivative according to the present invention or a pharmaceutically acceptable salt or solvate thereof. By effective amount or therapeutically effective amount is meant an amount of compound or a composition of the present invention effective in inhibiting the above-noted diseases and thus producing the desired therapeutic, ameliorative, inhibitory or preventative effect.

The amount of a heterocyclic derivative of the present invention or a pharmaceutically acceptable salt or solvate thereof, also referred to herein as the active ingredient, which is required to achieve a therapeutic effect will, of course, vary with the particular compound, the route of administration, the age and condition of the recipient and the particular disorder or disease being treated.

A suitable daily dose for any of the above mentioned disorders will be in the range of 0.001 to 50 mg per kilogram body weight of the recipient (e.g. a human) per day, preferably in the range of 0.01 to 20 mg per kilogram body weight per day. The desired dose may be presented as multiple sub-doses administered at appropriate intervals throughout the day.

Whilst it is possible for the active ingredient to be administered alone, it is preferable to present it as a pharmaceutical composition. The present invention therefore also provides a pharmaceutical composition comprising a heterocyclic derivative according to the present invention in admixture with one or more pharmaceutically acceptable excipient, such as the ones described in Gennaro et. al., Remmington: *The Science and Practice of Pharmacy*, 20$^{th}$ Edition, Lippincott, Williams and Wilkins, 2000; see especially part 5: pharmaceutical manufacturing. Suitable excipients are also described e.g., in the Handbook of Pharmaceutical Excipients, 2$^{nd}$ Edition; Editors A. Wade and P. J. Weller, American Pharmaceutical Association, Washington, The Pharmaceutical Press, London, 1994. Compositions include those suitable for oral, nasal, topical (including buccal, sublingual and transdermal), parenteral (including subcutaneous, intravenous and intramuscular) or rectal administration.

The mixtures of a heterocyclic derivative according to the present invention and one or more pharmaceutically acceptable excipient or excipients may be compressed into solid dosage units, such as tablets, or be processed into capsules or suppositories. By means of pharmaceutically suitable liquids the compounds can also be applied as an injection preparation in the form of a solution, suspension, emulsion, or as a spray, e.g., a nasal or buccal spray. For making dosage units e.g., tablets, the use of conventional additives such as fillers, colorants, polymeric binders and the like is contemplated. In general, any pharmaceutically acceptable additive can be used. The heterocyclic derivatives of the invention are also suitable for use in an implant, a patch, a gel or any other preparation for immediate and/or sustained release.

Suitable fillers with which the pharmaceutical compositions can be prepared and administered include lactose, starch, cellulose and derivatives thereof, and the like, or mixtures thereof used in suitable amounts. For parenteral administration, aqueous suspensions, isotonic saline solutions and sterile injectable solutions may be used, containing pharmaceutically acceptable dispersing agents and/or wetting agents, such as propylene glycol or butylene glycol.

The present invention further includes a pharmaceutical composition, as hereinbefore described, in combination with packaging material suitable for said composition, said packaging material including instructions for the use of the composition for the use as hereinbefore described.

The invention is further illustrated by the following examples which are not intended to limit the scope thereof.
Methods General Chemical Procedures: All reagents were either purchased from common commercial sources or synthesised according to literature procedures beginning from commercial reagents. Commercial reagents were used without further purification. Unless otherwise indicated, percent is percent by weight given the component and the total weight of the composition, temperature is in ° C. or is at ambient temperature and pressure is at or near atmospheric. Ion exchange chromatography was performed using Isolute Flash SCX-II (acidic) resin cartridges. Flash column chromatography was performed using pre-packed silica cartridges (RediSep or Biotage) on a Combiflash™ Retrieve™ system or similar. Microwave reactions were performed using an Emrys Optimizer™ (Personal Chemistry). Semi-preparative high pressure liquid chromatography (semi-prep. HPLC) was performed using the methods outlined below:

Method (i): Phenomenex Gemini (C18, 5 μm) 30 mm ID×100 mm; 10-95% acetonitrile-water over a 30 minute gradient; 30 ml/min; 0.1% trifluoroacetic acid buffer; detection by UV at 254 nm.

Method (ii): Waters XBridge (C18, 5 μm) 19 mm×50 mm; 5-20% acetonitrile-water over a 3 minute gradient then 20-95% acetonitrile-water over a 2 minute gradient; 20 ml/min; 0.1% trifluoroacetic acid buffer; detection by UV at 254 nm.

Method (iii): Waters XBridge (C18, 5 μm) 19 mm×50 mm; 5-95% acetonitrile-water over a 8 minute gradient; 20 ml/min; 0.1% trifluoroacetic acid buffer; detection by UV at 254 nm.

Mass spectra were recorded on a Shimadzu LC-8A (HPLC) PE Sciex API 150EX LC/MS or on an Agilent 1200 HPLC with Agilent 6140 LC/MS.
Abbreviations dimethylformamide (DMF), dichloromethane (DCM), diethylamime (DEA), ethyl acetate (EtOAc), ethanol (EtOH), high pressure liquid chromatography (HPLC), hour (hr), liquid chromatography/mass spectroscopy (LC/MS), methanol (MeOH), mass spectroscopy (MS), preparative (prep), racemic (rac), strong cation exchange (SCX), tetrahydrofuran (THF), acid base wash (ABW).

Procedure 1

Intermediate 1A: 5-Fluoro-2-nitrobenzoyl chloride

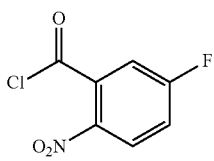 [SMILES: O=C(Cl)c1cc(F)ccc1[N+](=O)[O-]]

5-Fluoro-2-nitrobenzoic acid (15.0 g, 81.0 mmol) was refluxed in thionyl chloride (67.5 g, 567 mmol) for 2.5 hours. The reaction mixture was allowed to cool to room temperature and the excess thionyl chloride removed under reduced pressure, to afford 5-fluoro-2-nitrobenzoyl chloride (16.5 g, 81.0 mmol).

Procedure 2

Intermediate 2A: 5-Fluoro-N-(2-(isopropylamino)-2-oxoethyl)-2-nitrobenzamide

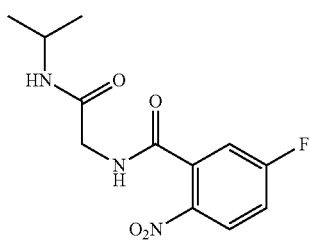 [SMILES: CC(C)NC(=O)CNC(=O)c1cc(F)ccc1[N+](=O)[O-]]

A solution of 2-amino-N-isopropylacetamide (11.3 g, 97.0 mmol) and N,N-diisopropylethylamine (20.1 g, 162 mmol) in dichloromethane (200 mL) was cooled using an ice water bath. A solution of 5-fluoro-2-nitrobenzoyl chloride (16.5 g, 81.0 mmol) in dichloromethane (200 mL) was added dropwise over 15 minutes. The resulting solution was stirred overnight. The reaction mixture was washed with 2N HCl solution (2×250 mL), brine (250 mL) and then dried over magnesium sulphate. The solution was filtered before concentrating under reduced pressure to afford 5-fluoro-N-(2-(isopropylamino)-2-oxoethyl)-2-nitrobenzamide (18.5 g, 65.0 mmol).

MS (ESI) m/z 284.0 [M+H]+

Similarly Prepared were

Intermediate 2B: 5-Fluoro-2-nitrobenzamide

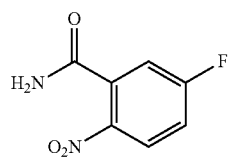 [SMILES: NC(=O)c1cc(F)ccc1[N+](=O)[O-]]

Intermediate 2C: 5-Fluoro-N-((1-(hydroxymethyl)cyclobutyl)methyl)-2-nitrobenzamide

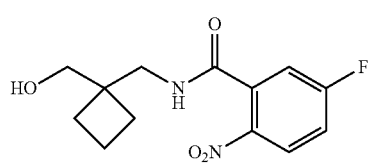 [SMILES: O=C(NCC1(CO)CCC1)c1cc(F)ccc1[N+](=O)[O-]]

Intermediate 2D: N-Cyclopropyl-5-fluoro-2-nitrobenzamide

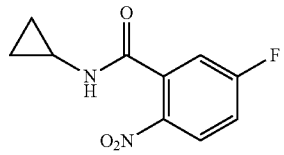 [SMILES: O=C(NC1CC1)c1cc(F)ccc1[N+](=O)[O-]]

Intermediate 2E: N-Cyclobutyl-5-fluoro-2-nitrobenzamide

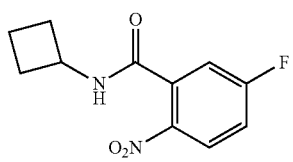 [SMILES: O=C(NC1CCC1)c1cc(F)ccc1[N+](=O)[O-]]

Intermediate 2F: 5-Fluoro-N-(3-hydroxy-2,2-dimethylpropyl)-2-nitrobenzamide

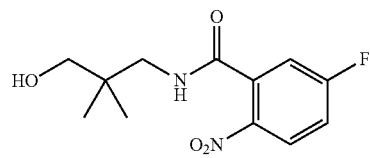 [SMILES: CC(C)(CO)CNC(=O)c1cc(F)ccc1[N+](=O)[O-]]

Procedure 3

Intermediate 3A: 5-Fluoro-N-methyl-2-nitrobenzamide

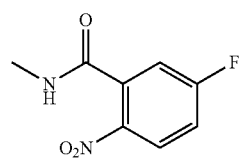

A solution of 5-fluoro-2-nitrobenzoic acid (0.5 g, 2.7 mmol) in dichloromethane (10 mL) was cooled with an ice water bath before the addition of N,N-diisopropylethylamine (1.13 g, 8.1 mmol). To this solution 2M methylamine in tetrahydrofuran (1.6 g, 3.24 mmol) was added dropwise over 5 minutes. 1-Propanephosphonic acid cyclic anhydride as a 50% wt solution in ethyl acetate (2.56 mL, 4.05 mmol) was added dropwise. The ice bath was then removed and stirring continued overnight. The mixture was purified on a 2 g ABW column to afford 5-fluoro-N-methyl-2-nitrobenzamide (0.26 g, 1.31 mmol).

Similarly Prepared were

Intermediate 3B: 5-Fluoro-N-ethyl-2-nitrobenzamide

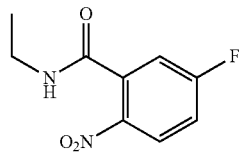

Intermediate 3C:
5-Fluoro-N-propyl-2-nitrobenzamide

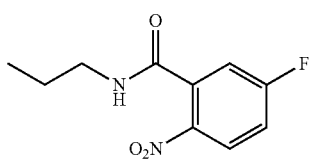 [SMILES: CCCNC(=O)c1cc(F)ccc1[N+](=O)[O-]]

Intermediate 3D:
5-Fluoro-N-isobutyl-2-nitrobenzamide

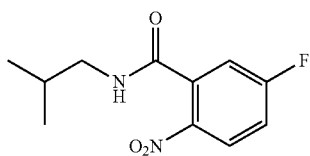 [SMILES: CC(C)CNC(=O)c1cc(F)ccc1[N+](=O)[O-]]

Intermediate 3E: 5-Fluoro-N-((tetrahydro-2H-pyran-4-yl)methyl)-2-nitrobenzamide

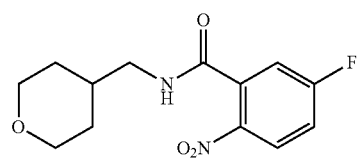 [SMILES: O=C(NCC1CCOCC1)c1cc(F)ccc1[N+](=O)[O-]]

Intermediate 3F: 5-Fluoro-N-(3-hydroxy-3-methyl-butyl)-2-nitrobenzamide

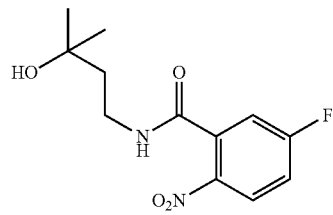 [SMILES: CC(C)(O)CCNC(=O)c1cc(F)ccc1[N+](=O)[O-]]

Intermediate 3G:
5-Fluoro-N-(propan-3-ol)-2-nitrobenzamide

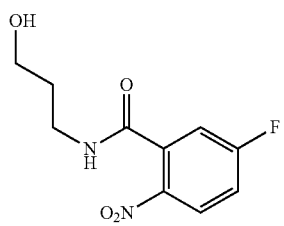 [SMILES: O=C(NCCCO)c1cc(F)ccc1[N+](=O)[O-]]

Intermediate 3H:
5-Fluoro-N-(cyclopropylmethyl)-2-nitrobenzamide

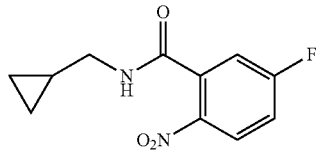 [SMILES: O=C(NCC1CC1)c1cc(F)ccc1[N+](=O)[O-]]

Intermediate 3I:
5-Fluoro-N-(isopropyl)-2-nitrobenzamide

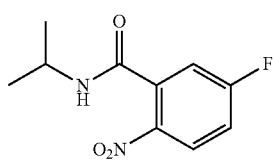 [SMILES: CC(C)NC(=O)c1cc(F)ccc1[N+](=O)[O-]]

Intermediate 3J: 5-Fluoro-N-((tetrahydro-2H-thiopyran-4-yl 1,1-dioxide)methyl)-2-nitrobenzamide

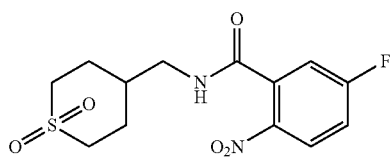

Intermediate 3K: tert-Butyl 2-(5-fluoro-2-nitrobenzamido)acetate

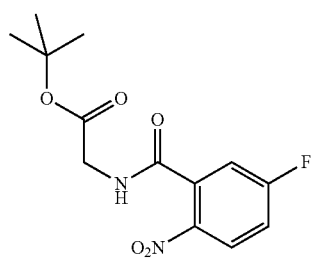 [SMILES: CC(C)(C)OC(=O)CNC(=O)c1cc(F)ccc1[N+](=O)[O-]]

Intermediate 3L: 4-Fluoro-N-methyl-2-nitrobenzamide

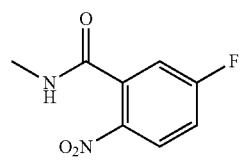

Intermediate 3M: 5-Fluoro-N-(2-methoxyethyl)-2-nitrobenzamide

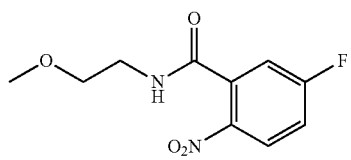 [SMILES: COCCNC(=O)c1cc(F)ccc1[N+](=O)[O-]]

Procedure 4

Intermediate 4A: 5-(1,4-Diazabicyclo[3.2.2]nonan-4-yl)-N-(2-(isopropylamino)-2-oxoethyl)-2-nitrobenzamide

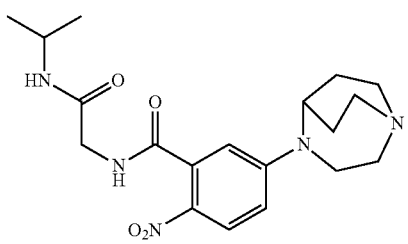 [SMILES: CC(C)NC(=O)CNC(=O)c1cc(N2CCN3CCC2CC3)ccc1[N+](=O)[O-]]

To a solution of 5-fluoro-N-(2-(isopropylamino)-2-oxoethyl)-2-nitrobenzamide (Intermediate 2A) (7.39 g, 26.1 mmol) in acetonitrile (240 mL) was added potassium carbonate (14.6 g, 104 mmol) followed by 1,4-diazabicyclo[3.2.2]nonane dihydrochloride (5.45 g, 27.4 mmol). The resulting suspension was heated to reflux at 96° C. overnight. The reaction mixture was filtered and concentrated. Sample was diluted in methanol (100 mL) and split between two 20 g SCX cartridges. Purification by SCX and evaporation to dryness afforded 5-(1,4-diazabicyclo[3.2.2]nonan-4-yl)-N-(2-(isopropylamino)-2-oxoethyl)-2-nitrobenzamide (7.0 g, 18.0 mmol).

MS (ESI) m/z 390.0 [M+H]+

Similarly Prepared were

Intermediate 4B: tert-Butyl 2-(5-(1,4-diazabicyclo[3.2.2]nonan-4-yl)-2-nitrobenzamido)acetate (from Intermediate 3K)

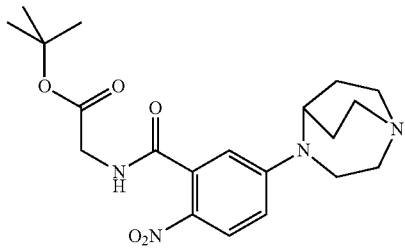

Intermediate 4C: N-(2-(Isopropylamino)-2-oxoethyl)-5-(8-methyl-8-azabicyclo[3.2.1]octan-3-ylamino)-2-nitrobenzamide (from Intermediate 2A)

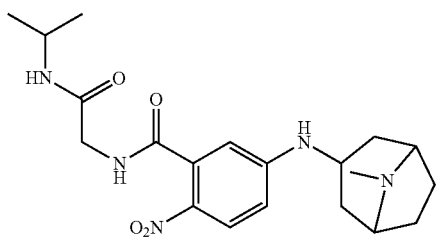 [SMILES: CC(C)NC(=O)CNC(=O)c1cc(NC2CC3CCC(C2)N3C)ccc1[N+](=O)[O-]]

Intermediate 4D: 5-(1,4-Diazabicyclo[3.2.2]nonan-4-yl)-2-nitrobenzamide (from Intermediate 2B)

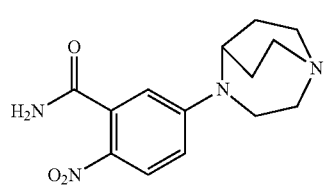 [SMILES: NC(=O)c1cc(N2CCN3CCC2CC3)ccc1[N+](=O)[O-]]

Intermediate 4E: 5-(1,4-Diazabicyclo[3.2.2]nonan-4-yl)-N-methyl-2-nitrobenzamide (from Intermediate 3A)

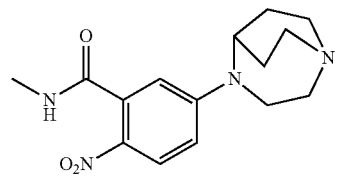 [SMILES: CNC(=O)c1cc(N2CCN3CCC2CC3)ccc1[N+](=O)[O-]]

Intermediate 4F: 5-(1,4-Diazabicyclo[3.2.2]nonan-4-yl)-N-ethyl-2-nitrobenzamide (from Intermediate 3B)

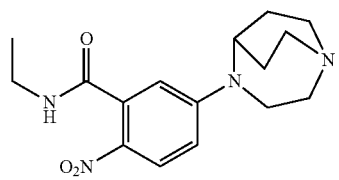

Intermediate 4G: 5-(1,4-Diazabicyclo[3.2.2]nonan-4-yl)-2-nitro-N-propylbenzamide (from Intermediate 3C)

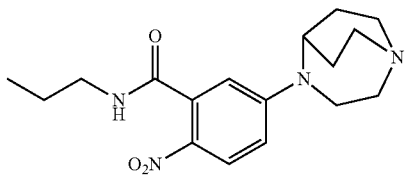 [SMILES: CCCNC(=O)c1cc(N2CCN3CCC2CC3)ccc1[N+](=O)[O-]]

Intermediate 4H: 5-(1,4-Diazabicyclo[3.2.2]nonan-4-yl)-N-isobutyl-2-nitrobenzamide (from Intermediate 3D)

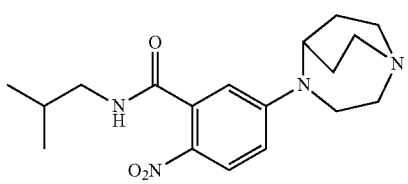 [SMILES: CC(C)CNC(=O)c1cc(N2CCN3CCC2CC3)ccc1[N+](=O)[O-]]

Intermediate 4I: 5-(1,4-Diazabicyclo[3.2.2]nonan-4-yl)-N-(cyclopropylmethyl)-2-nitrobenzamide (from Intermediate 3H)

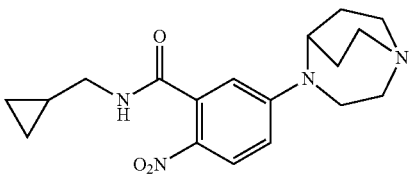 [SMILES: O=C(NCC1CC1)c1cc(N2CCN3CCC2CC3)ccc1[N+](=O)[O-]]

Intermediate 4J: 5-(1,4-Diazabicyclo[3.2.2]nonan-4-yl)-N-isopropyl-2-nitrobenzamide (from Intermediate 3I)

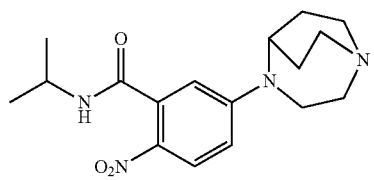

Intermediate 4K: 5-(1,4-Diazabicyclo[3.2.2]nonan-4-yl)-N-cyclopropyl-2-nitrobenzamide (from Intermediate 2D)

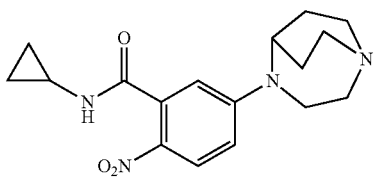

Intermediate 4L: 5-(1,4-Diazabicyclo[3.2.2]nonan-4-yl)-N-cyclobutyl-2-nitrobenzamide (from Intermediate 2E)

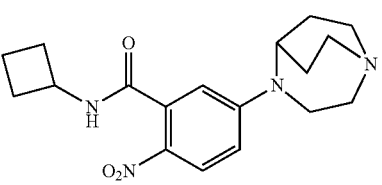

Intermediate 4M: 5-(1,4-Diazabicyclo[3.2.2]nonan-4-yl)-2-nitro-N-(tetrahydro-2H-pyran-4-yl)benzamide (from Intermediate 2E)

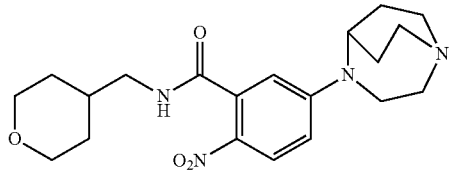

Intermediate 4N: 5-(1,4-Diazabicyclo[3.2.2]nonan-4-yl)-N-(3-hydroxy-3-methylbutyl)-2-nitrobenzamide (from Intermediate 3F)

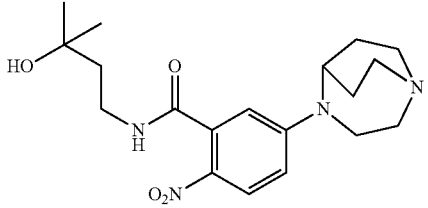

Intermediate 4O: 5-(1,4-Diazabicyclo[3.2.2]nonan-4-yl)-N-(3-hydroxypropyl)-2-nitrobenzamide (from Intermediate 3G)

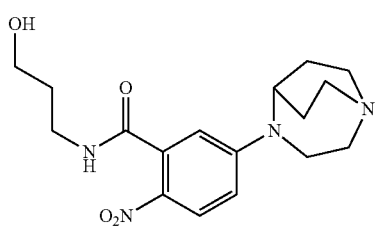 [SMILES: O=C(NCCCO)c1cc(N2CCN3CCC2CC3)ccc1[N+](=O)[O-]]

Intermediate 4P: 5-(1,4-Diazabicyclo[3.2.2]nonan-4-yl)-N-(tetrahydro-2H-thiopyran-4-yl 1,1-dioxide)methyl)-2-nitrobenzamide (from Intermediate 3J)

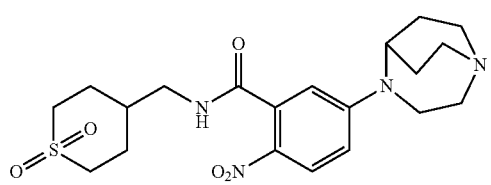

Intermediate 4Q: 5-(1,4-Diazabicyclo[3.2.2]nonan-4-yl)-N-((1-(hydroxymethyl)cyclobutyl)methyl)-2-nitrobenzamide (from Intermediate 2C)

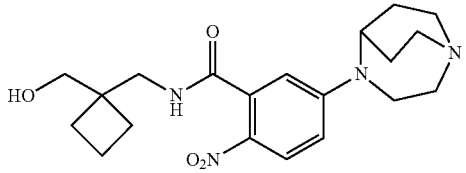 [SMILES: O=C(NCC1(CO)CCC1)c1cc(N2CCN3CCC2CC3)ccc1[N+](=O)[O-]]

Intermediate 4R: 5-(1,4-Diazabicyclo[3.2.2]nonan-4-yl)-N-(3-hydroxy-2,2-dimethylpropyl)-2-nitrobenzamide (from Intermediate 2F)

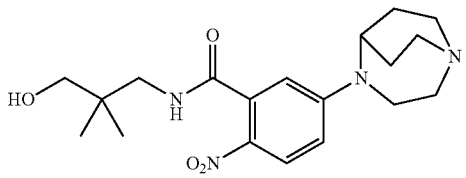

Intermediate 4S: 5-(1,4-Diazabicyclo[3.2.2]nonan-4-yl)-N-(2-methoxyethyl)-2-nitrobenzamide (from Intermediate 3M)

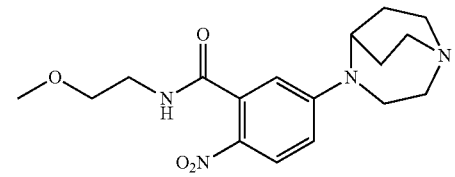 [SMILES: COCCNC(=O)c1cc(N2CCN3CCC2CC3)ccc1[N+](=O)[O-]]

Procedure 5

Intermediate 5A: (1S,4S)-tert-Butyl 5-(3-(2-(isopropylamino)-2-oxoethylcarbamoyl)-4-nitrophenyl)-2,5-diazabicyclo[2.2.1]heptane-2-carboxylate

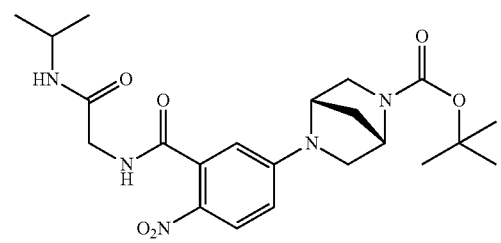 [SMILES: CC(C)NC(=O)CNC(=O)c1cc(N2C[C@@H]3C[C@H]2CN3C(=O)OC(C)(C)C)ccc1[N+](=O)[O-]]

To a solution of 5-fluoro-N-(2-(isopropylamino)-2-oxoethyl)-2-nitrobenzamide (1.0 g, 3.53 mmol) (Intermediate 2A) in acetonitrile (20 mL) was added potassium carbonate (1.46 g, 10.9 mmol) followed by (1S,4S)-tert-butyl 2,5-diazabicyclo[2.2.1]heptane-2-carboxylate (0.70 g, 3.53 mmol). The resulting suspension was heated to reflux at 90° C. for 6 hours. The reaction mixture was allowed to cool to room temperature, then filtered and concentrated. The resultant crude material was purified by a 25 g silica column in neat ethylacetate (Biotage Snap cartridge). Fractions of the product were combined and reduced to dryness under reduced pressure to afford (1S,4S)-tert-butyl 5-(3-(2-(isopropylamino)-2-oxoethylcarbamoyl)-4-nitrophenyl)-2,5-diazabicyclo[2.2.1]heptane-2-carboxylate (1.5 g, 3.25 mmol).

MS (ESI) m/z 484.0 [M+Na]+

Similarly Prepared were

Intermediate 5B: tert-Butyl 5-(3-(2-(isopropylamino)-2-oxoethylcarbamoyl)-4-nitrophenyl)hexahydropyrrolo[3,4-c]pyrrole-2(1H)-carboxylate (from Intermediate 2A)

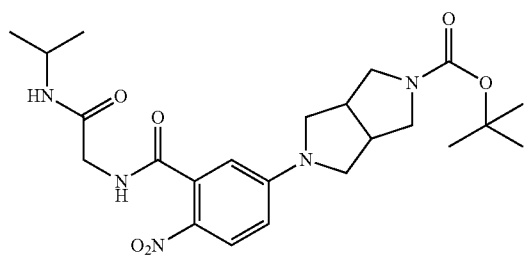

Intermediate 5C: tert-Butyl 5-(3-(methylcarbamoyl)-4-nitrophenyl)hexahydropyrrolo[3,4-c]pyrrole-2(1H)-carboxylate (from Intermediate 3A)

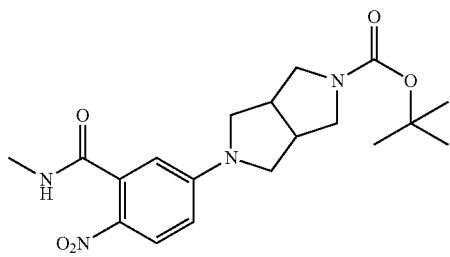 [SMILES: CNC(=O)c1cc(N2CC3CN(C(=O)OC(C)(C)C)CC3C2)ccc1[N+](=O)[O-]]

Intermediate 5D: (1S,4S)-tert-Butyl 5-(3-(methylcarbamoyl)-4-nitrophenyl)-2,5-diazabicyclo[2.2.1]heptane-2-carboxylate (from Intermediate 3A)

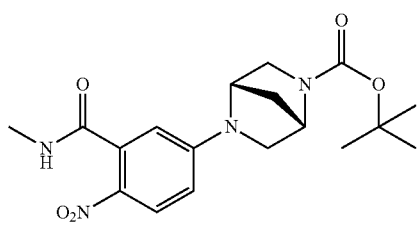 [SMILES: CNC(=O)c1cc(N2C[C@@H]3C[C@H]2CN3C(=O)OC(C)(C)C)ccc1[N+](=O)[O-]]

Procedure 6

Intermediate 6A: N-Methyl-2-nitro-5-(quinuclidin-3-ylamino)benzamide

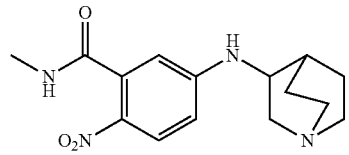 [SMILES: CNC(=O)c1cc(NC2CN3CCC2CC3)ccc1[N+](=O)[O-]]

To a mixture of quinuclidin-3-amine hydrochloride (1.06 g, 5.30 mmol) and polymer supported dimethylperhydro-1,3,2-diazaphosphorine (7.0 g, 15.4 mmol) in DMSO (50 mL) was added 5-fluoro-N-methyl-2-nitrobenzamide (Intermediate 3A) (1 g, 5.05 mmol) and reaction heated at 60° C. for 72 hours. The resin was removed by filtration and washed thoroughly with methanol and dichloromethane. The filtrate was purified using a 20 g SCX cartridge followed by trituration with dichloromethane/methanol/diethyl ether to afford N-methyl-2-nitro-5-(quinuclidin-3-ylamino)benzamide (0.41 g, 1.36 mmol).

MS (ESI) m/z 305.2 [M+H]+

Procedure 7

Intermediate 7A: 2-Amino-5-(1,4-diazabicyclo[3.2.2]nonan-4-yl)-N-(2-(isopropylamino)-2-oxoethyl)benzamide

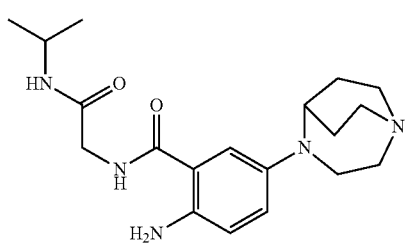 [SMILES: CC(C)NC(=O)CNC(=O)c1cc(N2CCN3CCC2CC3)ccc1N]

5-(1,4-diazabicyclo[3.2.2]nonan-4-yl)-N-(2-(isopropylamino)-2-oxoethyl)-2-nitrobenzamide (Intermediate 4A) (7.0 g, 18.0 mmol) was dissolved in methanol (120 mL) and palladium on carbon (0.7 g) added. The resulting solution was hydrogenated at room temperature under 4 bar pressure of hydrogen overnight. The reaction mixture was filtered through a celite pad, washed with methanol and dichloromethane, and concentrated to afford 2-amino-5-(1,4-diazabicyclo[3.2.2]nonan-4-yl)-N-(2-(isopropylamino)-2-oxoethyl)benzamide (6.4 g, 17.8 mmol).

MS (ESI) m/z 360.2 [M+H]+

Similarly Prepared were

Intermediate 7B: tert-Butyl 2-(2-amino-5-(1,4-diazabicyclo[3.2.2]nonan-4-yl)benzamido)acetate (from Intermediate 4B)

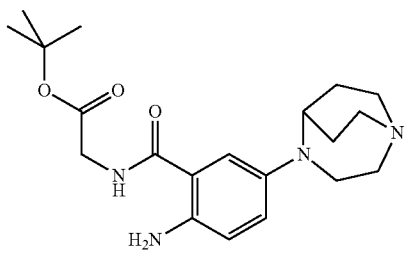 [SMILES: CC(C)(C)OC(=O)CNC(=O)c1cc(N2CCN3CCC2CC3)ccc1N]

Intermediate 7C: 2-Amino-N-(2-(isopropylamino)-2-oxoethyl)-5(8-methyl-8-azabicyclo[3.2.1]octan-3-ylamino)benzamide (from Intermediate 4C)

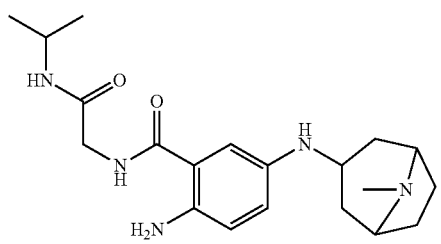 [SMILES: CC(C)NC(=O)CNC(=O)c1cc(NC2CC3CCC(C2)N3C)ccc1N]

Intermediate 7D: tert-Butyl 5-(4-amino-3-(2-(isopropylamino)-2-oxoethylcarbamoyl)phenyl)hexahydropyrrolo[3,4-c]pyrrole-2(1H)-carboxylate (from Intermediate 5B)

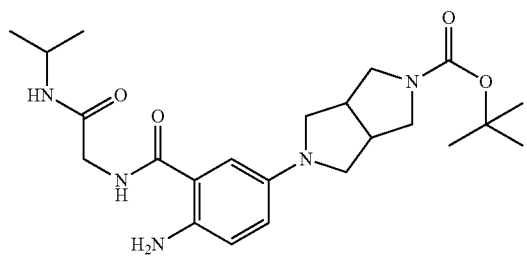 [SMILES: CC(C)NC(=O)CNC(=O)c1cc(N2CC3CN(C(=O)OC(C)(C)C)CC3C2)ccc1N]

Intermediate 7E: 2-Amino-5-((1S,4S)-2,5-diazabicyclo[2.2.1]heptan-2-yl)-N-(2-(isopropylamino)-2-oxoethyl)benzamide (from Intermediate 10A)

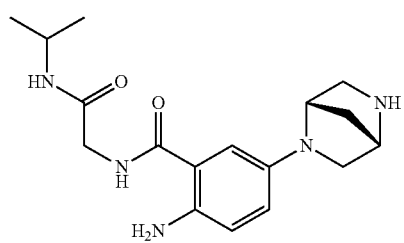 [SMILES: CC(C)NC(=O)CNC(=O)c1cc(N2C[C@@H]3C[C@H]2CN3)ccc1N]

Intermediate 7F: 2-Amino-5-(1,4-diazabicyclo[3.2.2]nonan-4-yl)-N-methylbenzamide (from Intermediate 4E)

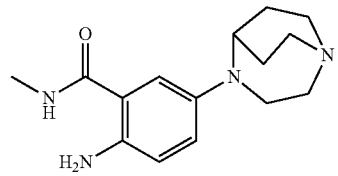 [SMILES: CNC(=O)c1cc(N2CCN3CCC2CC3)ccc1N]

Intermediate 7G: 2-Amino-5-(1,4-diazabicyclo[3.2.2]nonan-4-yl)-N-ethylbenzamide (from Intermediate 4F)

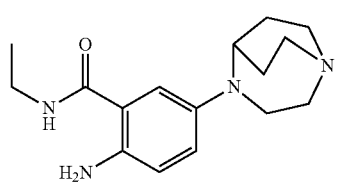 [SMILES: CCNC(=O)c1cc(N2CCN3CCC2CC3)ccc1N]

Intermediate 7H: 2-Amino-5-(1,4-diazabicyclo[3.2.2]nonan-4-yl)-N-propylbenzamide (from Intermediate 4G)

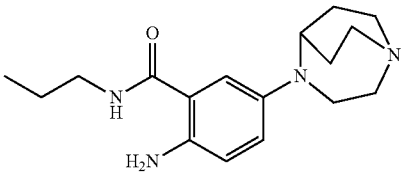 [SMILES: CCCNC(=O)c1cc(N2CCN3CCC2CC3)ccc1N]

Intermediate 7I: 2-Amino-5-(1,4-diazabicyclo[3.2.2]nonan-4-yl)-N-isobutylbenzamide (from Intermediate 4H)

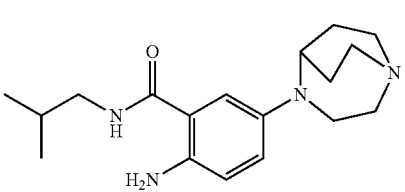

Intermediate 7J: 2-Amino-5-(1,4-diazabicyclo[3.2.2]
nonan-4-yl)-N-(cyclopropylmethyl)benzamide (from
Intermediate 4I)

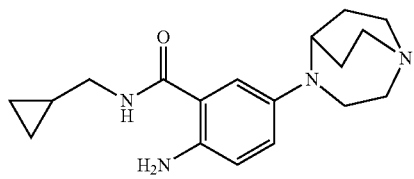 [SMILES: Nc1ccc(N2CCN3CCC2CC3)cc1C(=O)NCC1CC1]

Intermediate 7K: 2-Amino-5-(1,4-diazabicyclo
[3.2.2]nonan-4-yl)-N-isopropylbenzamide (from
Intermediate 4J)

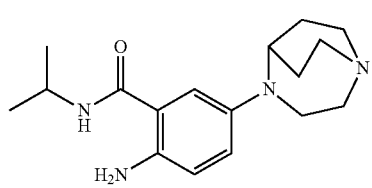

Intermediate 7L: 2-Amino-5-(1,4-diazabicyclo
[3.2.2]nonan-4-yl)-N-cyclopropylbenzamide (from
Intermediate 4K)

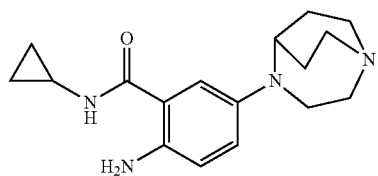 [SMILES: Nc1ccc(N2CCN3CCC2CC3)cc1C(=O)NC1CC1]

Intermediate 7M: 2-Amino-5-(1,4-diazabicyclo
[3.2.2]nonan-4-yl)-N-cyclobutylbenzamide (from
Intermediate 4L)

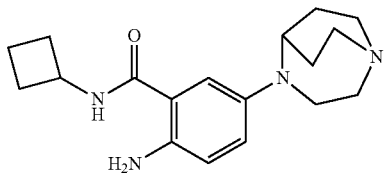

Intermediate 7N: 2-Amino-5-(1,4-diazabicyclo
[3.2.2]nonan-4-yl)-N-((tetrahydro-2H-pyran-4-yl)
methyl)benzamide (from Intermediate 4M)

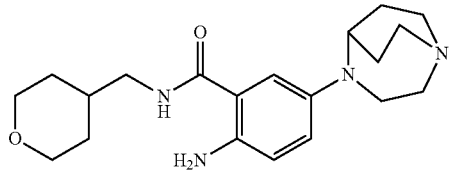 [SMILES: Nc1ccc(N2CCN3CCC2CC3)cc1C(=O)NCC1CCOCC1]

Intermediate 7O: 2-Amino-5-(1,4-diazabicyclo
[3.2.2]nonan-4-yl)-N-(3-hydroxy-3-methylbutyl)
benzamide (from Intermediate 4N)

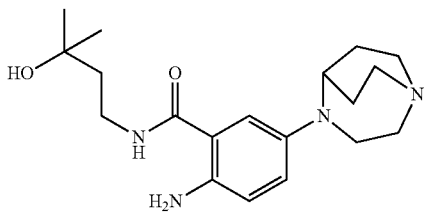 [SMILES: CC(C)(O)CCNC(=O)c1cc(N2CCN3CCC2CC3)ccc1N]

Intermediate 7P: 2-Amino-5-(1,4-diazabicyclo[3.2.2]
nonan-4-yl)-N-(3-hydroxypropyl)benzamide (from
Intermediate 4O)

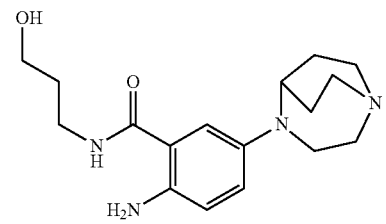

Intermediate 7Q: 2-Amino-5-(1,4-Diazabicyclo[3.2.2]
nonan-4-yl)-N-(tetrahydro-2H-thiopyran-4-yl 1,1-dioxide)
methyl)benzamide (from Intermediate 4P)

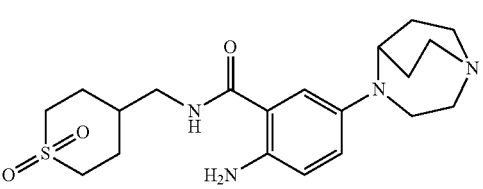

Procedure 8

Intermediate 8A: 2-Amino-N-methyl-5-(5-methyl-hexahydropyrrolo[3,4-c]pyrrole-2(1H)-yl)benzamide

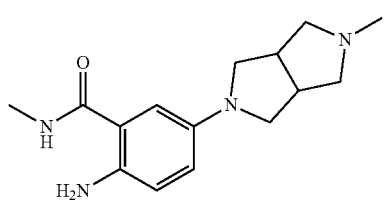

N-methyl-5-(5-methylhexahydropyrrolo[3,4-c]pyrrol-2(1H)-yl)-2-nitrobenzamide (Intermediate 13A) (900 mg, 2.96 mmol) was dissolved in ethanol (140 mL). The resulting solution was hydrogenated using the H-cube at 40° C. under 30 bar pressure of hydrogen, with a flow rate of 1 mL per minute through a 10% palladium on charcoal cartridge. The reaction mixture was concentrated to afford 2-amino-N-methyl-5-(5-methylhexahydropyrrolo[3,4-c]pyrrole-2(1H)-yl)benzamide, (824 mg, 3.01 mmol).

MS (ESI) m/z 275.2 [M+H]+

Similarly Prepared were

Intermediate 8B: 2-Amino-N-methyl-5-((1S,4S)-5-methyl-2,5-diazabicyclo[2.2.1]heptan-2-yl)benzamide (from Intermediate 13B)

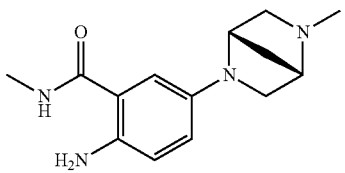

Intermediate 8C: 2-Amino-N-methyl-5-(quinuclidin-3-ylamino)benzamide (from Intermediate 6A)

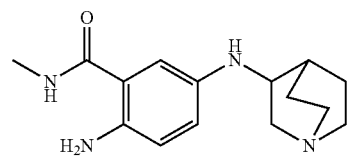 [SMILES: CNC(=O)c1cc(NC2CN3CCC2CC3)ccc1N]

Intermediate 8D: 2-Amino-5-(1,4-diazabicyclo[3.2.2]nonan-4-yl)benzamide (from Intermediate 4D)

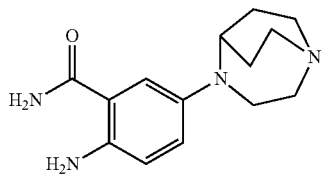 [SMILES: NC(=O)c1cc(N2CCN3CCC2CC3)ccc1N]

Intermediate 8E: 2-Amino-5-(1,4-diazabicyclo[3.2.2]nonan-4-yl)-N-((1-(hydroxymethyl)cyclobutyl)methyl)benzamide (from Intermediate 4Q)

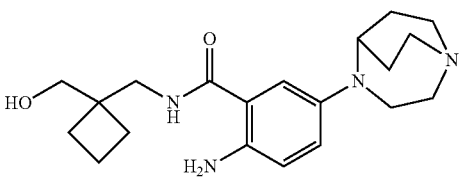

Intermediate 8F: 2-Amino-5-(1,4-Diazabicyclo[3.2.2]nonan-4-yl)-N-(3-hydroxy-2,2-dimethylpropyl)benzamide (from Intermediate 4R)

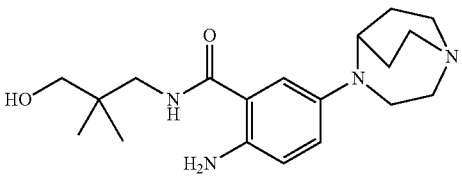 [SMILES: CC(C)(CO)CNC(=O)c1cc(N2CCN3CCC2CC3)ccc1N]

Intermediate 8G: 2-Amino-5-(1,4-Diazabicyclo[3.2.2]nonan-4-yl)-N-(2-methoxyethyl)benzamide (from Intermediate 4S)

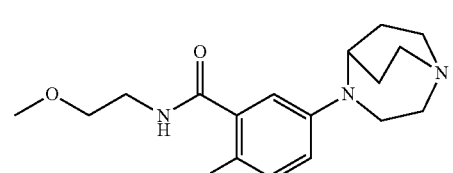

Intermediate 8H: 2-Amino-4-(1,4-diazabicyclo [3.2.2]nonan-4-yl)-N-methylbenzamide (from Intermediate 15A)

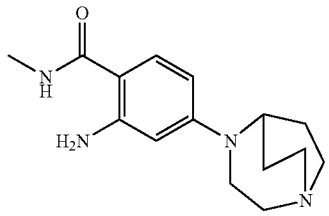 [SMILES: CNC(=O)c1ccc(N2CCN3CCC2CC3)cc1N]

Procedure 9

Intermediate 9A: 2-(2-Amino-5-(1,4-diazabicyclo [3.2.2]nonan-4-yl-benzamido)acetic acid

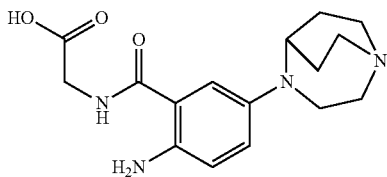 [SMILES: Nc1ccc(N2CCN3CCC2CC3)cc1C(=O)NCC(=O)O]

2,2,2-Trifluoroacetic acid (3.26 g, 28.0 mmol) was added to a solution of tert-butyl 2-(2-amino-5-(1,4-diazabicyclo [3.2.2]nonan-4-yl)benzamido)acetate (Intermediate 7B) (1.0 g, 2.67 mmol) in dichloromethane (20 mL) and methanol (2 mL). The resulting solution was stirred for 7 hours before leaving to stand over the weekend. The resultant crude material purified using a 5 g SCX cartridge to afford methyl 2-(2-amino-5-(1,4-diazabicyclo[3.2.2]nonan-4-yl)benzamido)acetate. This was dissolved in tetrahydrofuran (20 mL) and 1M lithium hydroxide solution (5.34 mL, 5.34 mmol) and water (2 mL) was added and the solution stirred overnight. The reaction mixture was then acidified and purified using a 5 g SCX cartridge to afford 2-(2-amino-5-(1,4-diazabicyclo [3.2.2]nonan-4-yl)benzamido)acetic acid (849 mg, 2.67 mmol).
MS (ESI) m/z 319.2 [M+H]+

Procedure 10

Intermediate 10A: 5-((1S,4S)-2,5-Diazabicyclo [2.2.1]heptan-2-yl)-N-(2-(isopropylamino)-2-oxoethyl)-2-nitrobenzamide

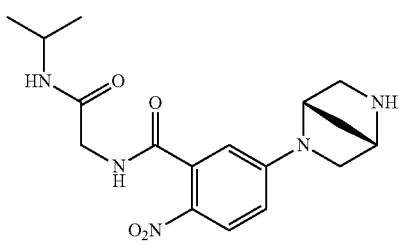 [SMILES: CC(C)NC(=O)CNC(=O)c1cc(N2C[C@@H]3C[C@H]2CN3)ccc1[N+](=O)[O-]]

2,2,2-Trifluoroacetic acid (4.6 g, 39.5 mmol) was added to a solution of (1S,4S)-tert-butyl 5-(3-(2-(isopropylamino)-2-oxoethylcarbamoyl)-4-nitrophenyl)-2,5-diazabicyclo[2.2.1] heptane-2-carboxylate (Intermediate 5A) (1.5 g, 3.25 mmol) in dichloromethane (15 mL). The resulting solution was stirred overnight. The resultant crude material was purified using a 20 g SCX cartridge to afford 5-((1S,4S)-2,5-diazabicyclo[2.2.1]heptan-2-yl)-N-(2-(isopropylamino)-2-oxoethyl)-2-nitrobenzamide (984 mg, 2.72 mmol).
MS (ESI) m/z 362.4 [M+H]+

Similarly Prepared were

Intermediate 10B: 5-(Hexahydropyrrolo[3,4-c]pyrrol-2(1H)-yl)-N-methyl-2-nitrobenzamide (from Intermediate 5C)

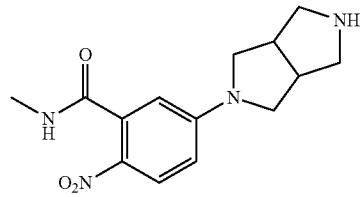 [SMILES: CNC(=O)c1cc(N2CC3CNCC3C2)ccc1[N+](=O)[O-]]

Intermediate 10C: 5-((1S,4S)-2,5-Diazabicyclo [2.2.1]heptan-2-yl)-N-methyl-2-nitrobenzamide (from Intermediate 5D)

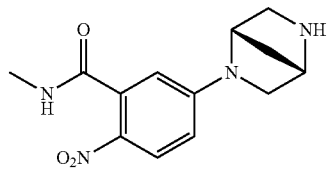

Procedure 11

Intermediate 11A: 2-(6-(1,4-Diazabicyclo[3.2.2] nonan-4-yl)-2-(3-chlorophenyl)-4-oxoquinazolin-3 (4H)-yl)acetic acid

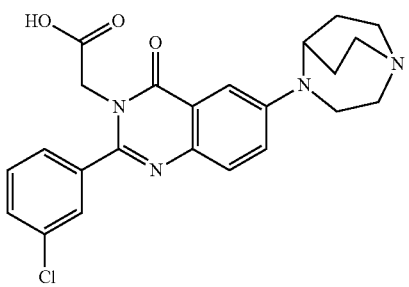 [SMILES: O=C(O)Cn1c(-c2cccc(Cl)c2)nc2ccc(N3CCN4CCC3CC4)cc2c1=O]

2-(2-Amino-5-(1,4-diazabicyclo[3.2.2]nonan-4-yl)benzamido)acetic acid (85.3 mg, 0.27 mmol) (Intermediate 9A) was dissolved in ethanol (3 mL). 3-Chlorobenzaldehyde (56.5 mg, 0.046 mL, 0.40 mmol) was added followed by 2 drops of acetic acid. The reaction mixture was refluxed at 85° C. overnight. The reaction mixture was diluted with methanol and purified directly using a 1 g SCX cartridge. The crude material was concentrated to dryness before re-dissolving in dichloromethane and manganese dioxide (18.8 mg, 0.32 mmol) added. The solution was then stirred overnight before filtering and concentrated under reduced pressure to give 2-(6-(1,4-diazabicyclo[3.2.2]nonan-4-yl)-2-(3-chlorophenyl)-4-oxoquinazolin-3(4H)-yl)acetic acid (54 mg, 0.12 mmol).

MS (ESI) m/z 439.0 [M+H]+

Procedure 12

Intermediate 12A: tert-Butyl 5-(3-(2-(isopropylamino)-2-oxoethyl)-4-oxo-2-phenyl-3,4-dihydroquiazolin-6-yl)hexahydropyrrolo[3,4-c]pyrrole-2(1H)-carboxylate

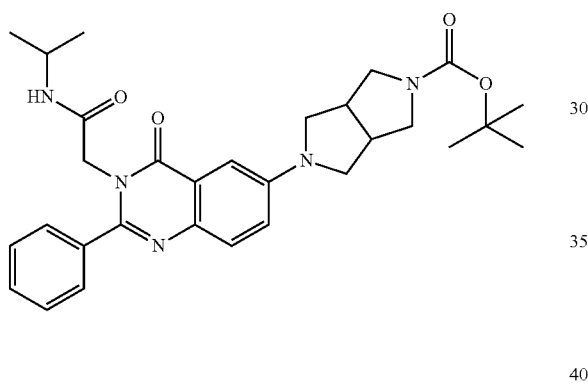

tert-Butyl 5-(4-amino-3-(2-(isopropylamino)-2-oxoethylcarbamoyl)phenyl)hexahydro pyrrolo[3,4-c]pyrrole-2(1H)-carboxylate (Intermediate 7D) (286 mg, 0.64 mmol) was dissolved in ethanol (2 mL) before addition of benzaldehyde (82 mg, 0.77 mmol) followed by 2 drops of acetic acid. The resulting solution was sealed in a Reactivial® and heated at 95° C. for 24 hours. Reaction mixture was then cooled to room temperature and diluted with methanol before loading directly onto a 1 g SCX cartridge. The crude material was purified by SCX, and the solvent removed under reduced pressure. The resultant product was re-dissolved in dichloromethane (2 mL) and manganese dioxide (66 mg, 0.75 mmol) added. The solution was stirred overnight. The reaction mixture was filtered and concentrated. The resultant crude material was purified using a 20 g SCX cartridge to afford tert-butyl 5-(3-(2-(isopropylamino)-2-oxoethyl)-4-oxo-2-phenyl-3,4-dihydroquiazolin-6-yl)hexahydropyrrolo[3,4-c]pyrrole-2(1H)-carboxylate (129 mg, 0.24 mmol), and 2-(6-(hexahydropyrrolo[3,4-c]pyrrol-2(1H)-yl)-4-oxo-2-phenylquinazolin-3(4H)-yl-N-isopropylacetamide (59 mg, 0.14 mmol).

MS (ESI) m/z 532 [M+H]+

Similarly Prepared were

Intermediate 12B: tert-Butyl 5-(3-(2-(isopropylamino)-2-oxoethyl)-4-oxo-3,4-dihydroquinazolin-6-yl)hexahydropyrrolo[3,4-c]pyrrole-2(1H)-carboxylate (from Intermediate 7D)

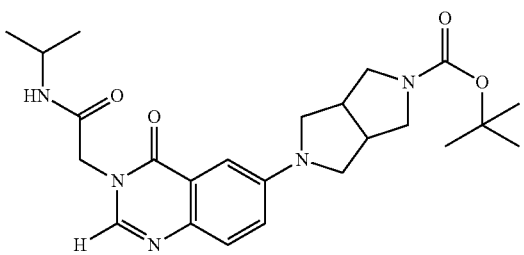 [SMILES: CC(C)NC(=O)Cn1cnc2ccc(N3CC4CN(C(=O)OC(C)(C)C)CC4C3)cc2c1=O]

Intermediate 12C: tert-Butyl 5-(2-cyclopropyl-3-(2-(isopropylamino)-2-oxoethyl)-4-oxo-3,4-dihydroquinazolin-6-yl)hexahydropyrrolo[3,4-c]pyrrole-2(1H)-carboxylate (from Intermediate 7D)

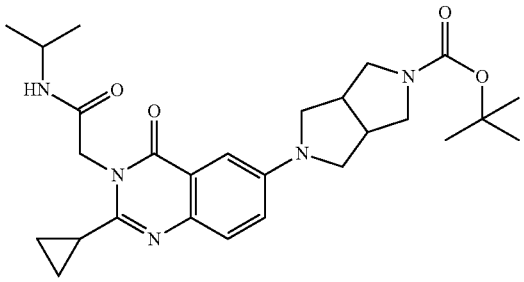 [SMILES: CC(C)NC(=O)Cn1c(C2CC2)nc2ccc(N3CC4CN(C(=O)OC(C)(C)C)CC4C3)cc2c1=O]

Intermediate 12D: 2-(6-((1S,4S)-2,5-Diazabicyclo[2.2.1]heptan-2-yl)-2-cyclopropyl-4-oxoquinazolin-3(4H)-yl)-N-isopropylacetamide (from Intermediate 7E)

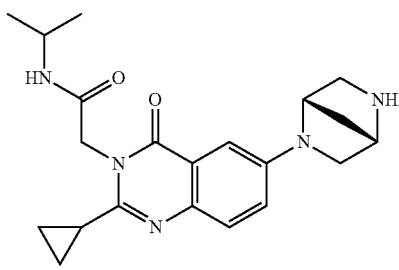 [SMILES: CC(C)NC(=O)Cn1c(C2CC2)nc2ccc(N3C[C@@H]4C[C@H]3CN4)cc2c1=O]

Procedure 13

Intermediate 13A: N-Methyl-5-(5-methylhexahydropyrrolo[3,4-c]pyrrol-2(1H)-yl)-2

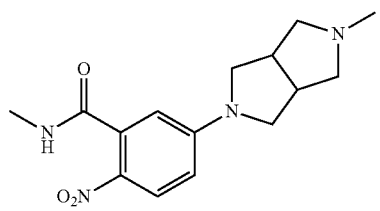

5-(hexahydropyrrolo[3,4-c]pyrrol-2(1H)-yl)-N-methyl-2-nitrobenzamide (1.78 g, 6.13 mmol) (Intermediate 10B) was dissolved in acetonitrile (45 mL) before addition of formaldehyde (0.6 g, 7.36 mmol) and MP-cyanoborohydride (3.6 g, 9.25 mmol) followed by 6 drops of acetic acid. The resulting mixture was split into 3 microwave vials and heated at 130° C. for 20 minutes. The reaction mixture was filtered and concentrated. The resultant crude material was purified by a 50 g silica column in 100% dichloromethane, 20% methanol in dichloromethane, 100% methanol (Biotage Snap cartridge). Fractions of the product were combined and reduced to dryness under reduced pressure to afford N-methyl-5-(5-methylhexahydropyrrolo[3,4-c]pyrrol-2(1H)-yl)-2-nitrobenzamide (900 mg, 2.96 mmol).
MS (ESI) m/z 305.0 [M+H]+

Similarly Prepared were

Intermediate 13B: N-Methyl-5-((1S,4S)-5-methyl-2,5-diazabicyclo[2.2.1]heptan-2-yl)-2-nitrobenzamide (from Intermediate 10C)

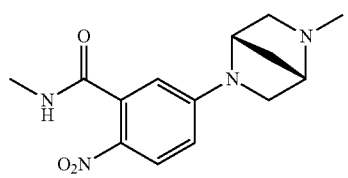

Procedure 14

Intermediate 14A: 2-(6-(1,4-Diazabicyclo[3.2.2]nonan-4-yl)-2-ethyl-4-oxoquinazolin-3(4H)-yl)acetic acid

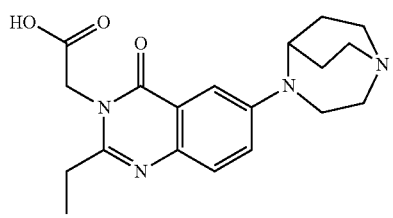 [SMILES: CCc1nc2ccc(N3CCN4CCC3CC4)cc2c(=O)n1CC(=O)O]

2-(2-Amino-5-(1,4-diazabicyclo[3.2.2]nonan-4-yl)benzamido)acetic acid (85.3 mg, 0.27 mmol) (Intermediate 9A) (100 mg, 0.36 mmol) was dissolved in triethoxypropane (1 mL), and heated in the microwave at 160° C. for 10 minutes. Reaction allowed to cool to room temperature and lithium hydroxide solution added (0.5 mL, 1M in methanol) and reaction stirred overnight. Organic layer purified using a 1 g SCX cartridge, followed by preparative-HPLC. Purified sample was free-based using 500 mg SCX cartridge to afford 2-(6-(1,4-diazabicyclo[3.2.2]nonan-4-yl)-2-ethyl-4-oxoquinazolin-3(4H)-yl)acetic acid (76 mg, 0.21 mmol).
MS (ESI) m/z 357.2 [M+H]+

Procedure 15

Intermediate 15A: 4-(1,4-Diazabicyclo[3.2.2]nonan-4-yl)-N-methyl-2-nitrobenzamide

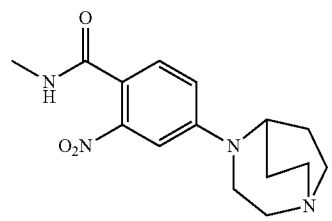 [SMILES: CNC(=O)c1ccc(N2CCN3CCC2CC3)cc1[N+](=O)[O-]]

To a solution of 4-fluoro-N-methyl-2-nitrobenzamide (Intermediate 3L) (0.65 g, 3.3 mmol) in dimethylsulfoxide (50 mL) was added 1,4-diazabicyclo[3.2.2]nonane (0.62 g, 4.9 mmol) and potassium carbonate (1.36 g, 9.8 mmol). The resulting suspension was heated at 90° C. for 4 days. The mixture was filtered and the filtrate purified using a 20 g SCX cartridge to afford 4-(1,4-diazabicyclo[3.2.2]nonan-4-yl)-N-methyl-2-nitrobenzamide (0.8 g, 2.7 mmol).
$^1$H NMR (400 MHz, CDCl$_3$): 7.35 (1H, d J=16.8 Hz), 7.1 (1H, d J=2.8 Hz), 6.85 (1H, dd J=8.8, 2.8 Hz) 5.68-5.76 (1H, bs), 4.03-4.09 (1H, bs), 3.58-3.61 (2H, m), 3.06-3.18 (4H, m), 2.95-3.03 (2H, m), 3.0 (3H, d J=4.8 Hz), 2.06-2.13 (2H, m), 1.71-1.81 (2H, m)

Procedure 16

Intermediate 16A: 5-Fluoro-N-methyl-2-nitrobenzenesulfonamide

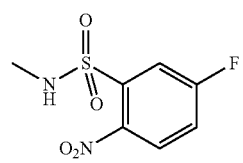

A solution of 5-fluoro-2-nitrobenzene-1-sulfonyl chloride (2.0 g, 8.35 mmol) in dichloromethane (50 mL) was cooled using an ice water bath. 2M methylamine in tetrahydrofuran (5.0 mL, 10.0 mmol) was added. The resulting solution was stirred for 2 hours. The reaction mixture was washed with 2N HCl solution (2×100 mL), brine (100 mL) and then dried over magnesium sulphate. The solution was filtered before concentrating under reduced pressure to afford 5-fluoro-N-methyl-2-nitrobenzenesulfonamide (1.79 g, 7.64 mmol).

¹H NMR; δ (ppm)(CHCl₃-d): 7.99-7.95 (1H, m), 7.87 (1H, dd, J=7.53, 2.5 Hz), 7.43-7.38 (1H, m), 5.33 (1H, bs), 2.83 (3H, s,).

Similarly Prepared were

Intermediate 16B:
5-Fluoro-2-nitrobenzenesulfonamide

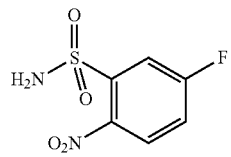

Procedure 17

Intermediate 17A: 5-(1,4-Diazabicyclo[3.2.2]nonan-4-yl)-N-methyl-2-nitrobenzenesulfonamide

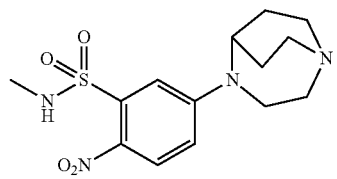 [SMILES: CNS(=O)(=O)c1cc(N2CCN3CCC2CC3)ccc1[N+](=O)[O-]]

To a solution of 5-fluoro-N-methyl-2-nitrobenzenesulfonamide (Intermediate 16A) (1.0 g, 4.27 mmol) in acetonitrile (10 mL) was added potassium carbonate (1.77 g, 12.81 mmol) followed by 1,4-diazabicyclo[3.2.2]nonane 2,2,2-trifluoroacetate (1.17 g, 4.27 mmol). The resulting suspension was heated to reflux at 96° C. overnight. The reaction mixture was diluted in water (50 mL) and split between two 20 g SCX cartridges. Purification by SCX and evaporation to dryness afforded 5-(1,4-diazabicyclo[3.2.2]nonan-4-yl)-N-methyl-2-nitrobenzenesulfonamide (1.17 g, 3.44 mmol).
MS (ESI) m/z 341.2 [M+H]+

Similarly Prepared were

Intermediate 17B: 5-(1,4-Diazabicyclo[3.2.2]nonan-4-yl)-2-nitrobenzenesulfonamide
(from Intermediate 16B)

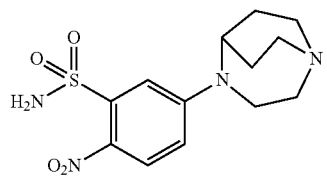 [SMILES: NS(=O)(=O)c1cc(N2CCN3CCC2CC3)ccc1[N+](=O)[O-]]

Procedure 18

Intermediate 18A: 2-Amino-5-(1,4-diazabicyclo[3.2.2]nonan-4-yl)-N-methylbenzenesulfonamide

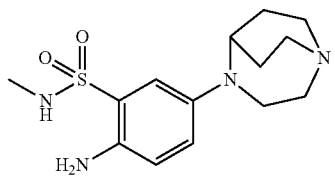

5-(1,4-diazabicyclo[3.2.2]nonan-4-yl)-N-methyl-2-nitrobenzenesulfonamide (Intermediate 17A) (1.0 g, 2.94 mmol) was dissolved in 2M ammonia in methanol (110 mL). The resulting solution was hydrogenated using the H-cube at 40° C. under 30 bar pressure of hydrogen, with a flow rate of 1 mL per minute through a 10% palladium on charcoal cartridge. The reaction mixture was purified by SCX and evaporated to afford 2-amino-5-(1,4-diazabicyclo[3.2.2]nonan-4-yl)-N-methylbenzenesulfonamide, (868 mg, 2.8 mmol). ¹H NMR; δ (ppm)(CHCl₃-d): 7.17 (1H, d, J=3.01 Hz), 6.88 (1H, dd, J=9.04, 3.01 Hz), 6.72 (1H, d, J=9.04 Hz), 4.82 (1H, bs), 4.31 (2H, bs), 3.88-3.87 (1H, m), 3.42-3.39 (2H, m), 3.13-2.97 (6H, m), 2.57 (3H, d, J=3.51 Hz), 2.11-2.04 (2H, m), 1.76-1.68 (2H, m).

Similarly Prepared were

Intermediate 18B: 2-Amino-5-(1,4-diazabicyclo[3.2.2]nonan-4-yl)benzenesulfonamide (from Intermediate 17B)

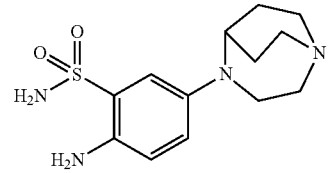 [SMILES: Nc1ccc(N2CCN3CCC2CC3)cc1S(N)(=O)=O]

Procedure 19

Intermediate 19A:
6-Bromo-3-methylquinazolin-4(3H)-one

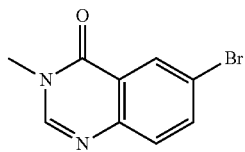

To a suspension of 6-bromoquinazolni-4(3H)-one (0.5 g, 2.22 mmol) in THF (12 mL) under nitrogen, was added sodium hydride (0.13 g, 3.33 mmol) and reaction stirred for 30 minutes. The reaction was then cooled using an ice bath and methyl 4-nitrobenzenesulfonate (0.48 g, 2.22 mmol) was added. Reaction allowed to warm to room temperature and stirred overnight. Diluted with water and extracted with ethylacetate. Organic layer washed with brine, dried (MgSO₄) and concentrated under reduced pressure. The resultant crude material was purified by a 25 g silica column in 0-10% methanol in DCM (Biotage Snap cartridge) followed by preparative-HPLC and 10 g SCX cartridge to afford 6-bromo-3-methylquinazolin-4(3H)-one (0.22 g, 0.90 mmol).

MS (ESI) m/z 240.0 [M+H]+

Similarly Prepared were

Intermediate 19B:
7-Bromo-2-methylisoquinolin-1(2H)-one

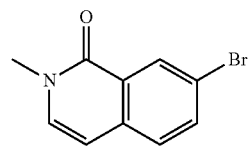

Procedure 20

Intermediate 20A: tert-Butyl 5-(3-methyl-4-oxo-3,4-dihydroquinazolin-6-yl)hexahydropyrrolo[3,4-c]pyrrole-2(1H)-carboxylate

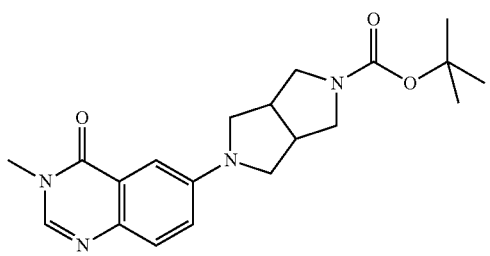 [SMILES: Cn1cnc2ccc(N3CC4CN(C(=O)OC(C)(C)C)CC4C3)cc2c1=O]

A mixture of 6-bromo-3-methylquinazolin-4(3H)-one (Intermediate 19A) (0.46 g, 1.92 mmol), tert-butyl hexahydropyrrolo[3,4-c]pyrrole-2(1H) carboxylate (0.49 g, 2.31 mmol), potassium phosphate, tribasic (1.33 g, 5.77 mmol), 2-dicyclohexylphosphino-2',6'-di-i-propoxy-1,1-biphenyl (26.9 mg, 0.06 mmol) and tris(dibenzyllideneacetone)dipalladium (0) (17.6 mg, 0.02 mmol) in dioxane (10 mL) was heated at 90° C. for 20 h. The mixture was diluted with water and the product extracted into dichloromethane. The organic layer was evaporated to dryness, re-dissolved in methanol and purified using a 5 g SCX column. The mixture was then further purified on silica (25 g SNAP column on SP4). Eluting with dichloromethane to 60/40 dichloromethane/(2M NH3 in methanol) to afford tert-butyl 5-(3-methyl-4-oxo-3,4-dihydroquinazolin-6-yl)hexahydropyrrolo[3,4-c]pyrrole-2(1H)-carboxylate (270 mg, 0.73 mmol).

MS (ESI) m/z 371.2 [M+H]+

Similarly Prepared were

Intermediate 20B: tert-Butyl 5-(2-methyl-1-oxo-1,2-dihydroisoquinolin-7-yl)hexahydropyrrolo[3,4-c]pyrrole-2(1H)-carboxylate (from Intermediate 19B)

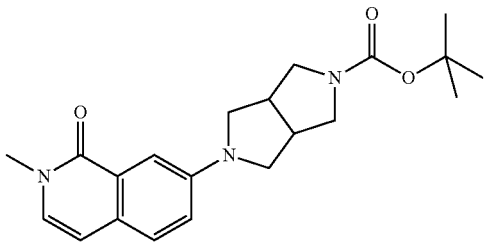 [SMILES: Cn1ccc2ccc(N3CC4CN(C(=O)OC(C)(C)C)CC4C3)cc2c1=O]

Procedure 21

Intermediate 21A: 6-(Hexahydropyrrolo[3,4-c]pyrrol-2(1H)-yl)-3-methylquinazolin-4(3H)-one

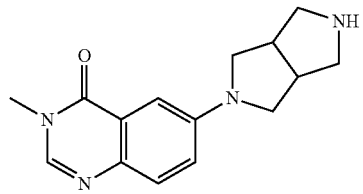 [SMILES: Cn1cnc2ccc(N3CC4CNCC4C3)cc2c1=O]

To a solution of tert-butyl 5-(3-methyl-4-oxo-3,4-dihydroquinazolin-6-yl)hexahydropyrrolo[3,4-c]pyrrole-2(1H)-carboxylate (Intermediate 20A) (80 mg, 0.22 mmol) in dichloromethane (2 mL) was added trifluoroacetic acid (0.5 mL) and the reaction allowed to stand overnight. The reaction was diluted with methanol and passed through a scx cartridge (500 mg) to afford 6-(hexahydropyrrolo[3,4-c]pyrrol-2(1H)-yl)-3-methylquinazolin-4(3H)-one (58 mg, 0.21 mmol).

MS (ESI) m/z 271.2 [M+H]+

Procedure 22

Intermediate 22A: 5-Bromo-N,2-dimethylbenzamide

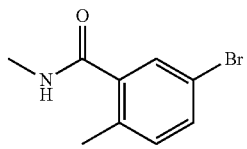

To a solution of 5-bromo-2-methylbenzoic acid (2.325 mmol, 0.5 g) in dichloromethane (25 mL) under nitrogen was added N,N-diisopropylethylamine (0.75 g, 5.8 mmol). Reaction then cooled in an ice bath to 2° C. and the yellow solution treated with 2M methylamine in tetrahydrofuran (3.49 mL, 6.98 mmol) over 5 minutes, followed by 1-propanephosphonic acid cyclic anhydride as a 50% wt solution in ethyl acetate (2.08 mL, 3.49 mmol) added dropwise. The ice bath was then removed and stirring continued overnight. The mixture was purified on silica (15 g column on Isolera 4) eluting with 0-5% methanol in dichloromethane to afford 5-Bromo-N,2-dimethylbenzamide (0.5 g, 2.2 mmol).

MS (ESI) m/z 228, 230 [M+H]+

Procedure 23

Intermediate 23A:
7-Bromo-3-(3-chlorophenyl)isoquinolin-1(2H)-one

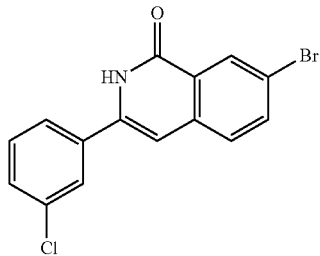 [SMILES: O=c1[nH]c(-c2cccc(Cl)c2)cc2ccc(Br)cc12]

To a solution of 2M lithium diisopropylamide (19.73 mL, 39.5 mmol) in tetrahydrofuran (30 mL) at −78° C. was added dropwise a solution of 5-bromo-N,2-dimethylbenzamide (Intermediate 22A) (3.0 g, 13.15 mmol) in THF (14 mL) followed by a solution of 3-chlorobenzonitrile (1.809 g, 13.15 mmol) in THF (14 mL) and the mixture was stirred at −78° C. for 2.5 hours. Reaction allowed to warm to room temperature and saturated NH$_4$Cl (aq) was added. The THF was removed under reduced pressure and the resulting mixture extracted into ethyl acetate and washed with brine (precipitate was observed in both layers). Organics were evaporated to dryness, washed with methanol and dried in a vacuum oven to afford 7-bromo-3-(3-chlorophenyl)isoquinolin-1(2H)-one (0.9 g, 2.69 mmol).

MS (ESI) m/z 333.8, 336.8 [M+H]+

Procedure 24

Intermediate 24A: 7-Bromo-3-(3-chlorophenyl)-2-methylisoquinolin-1(2H)-one

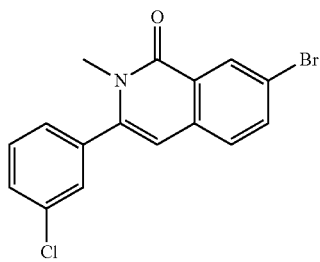 [SMILES: Cn1c(-c2cccc(Cl)c2)cc2ccc(Br)cc2c1=O]

7-Bromo-3-(3-chlorophenyl)isoquinolin-1(2H)-one (Intermediate 23A) (0.1 g, 0.299 mmol) was dissolved in THF (4 mL), under an atmosphere of nitrogen. Sodium hydride (0.018 g, 0.448 mmol) was added and reaction stirred for 30 minutes. The reaction was then cooled using an ice bath and methyl 4-nitrobenzenesulfonate (0.065 g, 0.299 mmol) was added. The reaction was allowed to warm to room temperature and left to stir overnight. Water was added to the reaction mixture and extracted with EtOAC (×2). The organics were combined and washed with brine, dried (MgSO$_4$) filtered and concentrated under reduced pressure. The mixture was purified on silica (25 g column on Isolera 4) eluting with 0-10% methanol in dichloromethane to afford 7-bromo-3-(3-chlorophenyl)-2-methylisoquinolin-1(2H)-one (51 mg, 0.15 mmol).

$^1$H NMR; δ (ppm)(CHCl$_3$-d): 8.59 (1H, d, J=2.0 Hz), 7.74-7.71 (1H, dd, J=8.4, 2.0 Hz), 7.46-7.30 (5H, m), 6.40 (1H, s), 3.42 (3H, s).

Procedure 25

Intermediate 25A: 2-Chloro-5-nitroisonicotinic acid

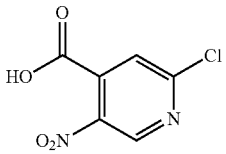 [SMILES: O=C(O)c1cc(Cl)ncc1[N+](=O)[O-]]

2-chloro-4-methyl-5-nitropyridine (1.0 g, 5.8 mmol) was cooled using an ice water bath. Sodium dichromate dihydrate (3.45 g, 11.6 mmol) dissolved in sulphuric acid (50 mL) was added dropwise, ensuring reaction temperature does not exceed 15° C. After complete addition, reaction allowed to warm to room temperature and stirred overnight. Quenched with ice, extracted into ethylacetate and concentrated under reduced pressure to afford 2-chloro-5-nitroisonicotinic acid (1.3 g, 6.4 mmol).

Procedure 26

Intermediate 26A: Methyl 2-chloro-5-nitroisonicotinate

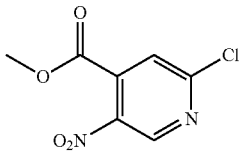

To a solution of 2-chloro-5-nitroisonicotinic acid (Intermediate 25A) (0.64 g, 3.17 mmol) in DMF (15 mL) under nitrogen was added sodium carbonate (1.0 g, 9.51 mmol). Reaction cooled in an ice bath and methyliodide (1.35 g, 9.51 mmol) was added dropwise. After complete addition, reaction allowed to warm to room temperature and stirred overnight under nitrogen. The reaction mixture was filtered and concentrated. The resultant crude material was purified by a 20 g silica column eluting with 40% ethylacetate in hexane to afford methyl 2-chloro-5-nitroisonicotinate (0.62 g, 2.86 mmol).

Procedure 27

Intermediate 27A: Methyl 2-(1,4-diazabicyclo[3.2.2]nonan-4-yl)-5-nitroisonicotinate

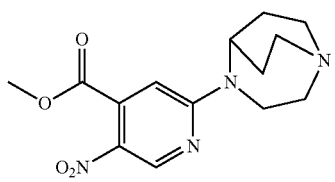 [SMILES: COC(=O)c1cc(N2CCN3CCC2CC3)ncc1[N+](=O)[O-]]

To a solution of methyl 2-chloro-5-nitroisonicotinate (Intermediate 26A) (0.1 g, 0.46 mmol) in methanol (3 mL) under nitrogen was added 1,4-diazabicyclo[3.2.2]nonane (0.18 g, 0.55 mmol) and triethylamine (7 mg, 0.69 mmol), reaction then stirred overnight. The reaction mixture was concentrated and purified by a 10 g silica column eluting with 40% ethylacetate in hexane to afford methyl 2-(1,4-diazabicyclo[3.2.2]nonan-4-yl)-5-nitroisonicotinate.

Similarly Prepared were

Intermediate 27B: Methyl 5-((1S,4S)-5-methyl-2,5-diazabicyclo[2.2.1]heptan-2-yl)-2-nitrobenzoate (from methyl 5-bromo-2-nitrobenzoate)

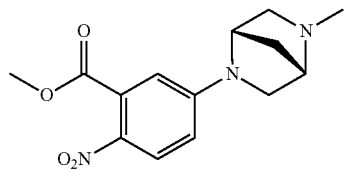

Procedure 28

Intermediate 28A: 2-(1,4-Diazabicyclo[3.2.2]nonan-4-yl)-N-methyl-5-nitroisonicotinamide

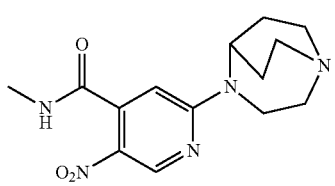 [SMILES: CNC(=O)c1cc(N2CCN3CCC2CC3)ncc1[N+](=O)[O-]]

Methyl 2-(1,4-diazabicyclo[3.2.2]nonan-4-yl)5-nitroisonicotinate (Intermediate 27A) (0.1 g, 0.46 mmol) and 2M methylamine in methanol (5 mL) were sealed in a tube and heated at 90° C. overnight. The reaction mixture was concentrated and purified by a 10 g silica column eluting with 0-10% methanol in DCM to afford 2-(1,4-diazabicyclo[3.2.2]nonan-4-yl)-N-methyl-5-nitroisonicotinamide (96 mg, 0.31 mmol).

Similarly Prepared were

Intermediate 28B: 2-(1,4-Diazabicyclo[3.2.2]nonan-4-yl)-5-nitroisonicotinamide (from Intermediate 27A)

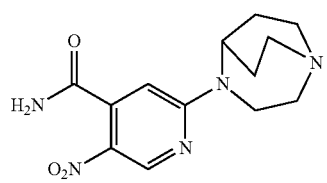

Procedure 29

Intermediate 29A: 2-(1,4-Diazabicyclo[3.2.2]nonan-4-yl)-5-nitroisonicotinic acid

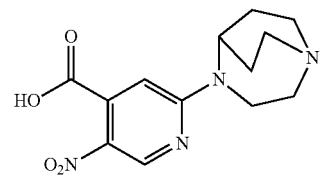 [SMILES: O=C(O)c1cc(N2CCN3CCC2CC3)ncc1[N+](=O)[O-]]

To a solution of methyl 2-(1,4-diazabicyclo[3.2.2]nonan-4-yl)5-nitroisonicotinate (Intermediate 27A) (6.0 g, 19.6 mmol) in tetrahydrofuran (15 mL) under nitrogen was added lithium hydroxide (2.47 g, 58.8 mmol), methanol (10 mL) and water (15 mL), reaction then stirred overnight. The reaction mixture was concentrated and purified by a 50 g silica column eluting with 10-40% methanol in DCM to afford 2-(1,4-diazabicyclo[3.2.2]nonan-4-yl)-5-nitroisonicotinic acid (3.2 g, 10.9 mmol).

Procedure 30

Intermediate 30A: 2-(1,4-Diazabicyclo[3.2.2]nonan-4-yl)-N-(3-hydroxy-2,2-dimethylpropyl)-5-nitroisonicotinamide

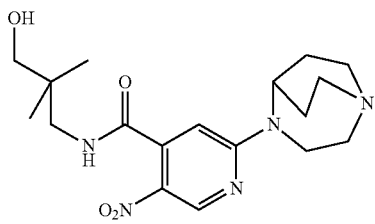 [SMILES: CC(C)(CO)CNC(=O)c1cc(N2CCN3CCC2CC3)ncc1[N+](=O)[O-]]

To a solution of 2-(1,4-diazabicyclo[3.2.2]nonan-4-yl)-5-nitroisonicotinic acid (Intermediate 29A) (2.0 g, 6.8 mmol) in DMF (25 mL) was added 3-amino-2,2-dimethylpropan-1-ol (0.85 g, 8.2 mmol), triethylamine (1 g, 10.3 mmol) and HATU (3.16, 10.3 mmol) under nitrogen, reaction then stirred overnight. The reaction mixture was concentrated and purified by HPLC to afford 2-(1,4-diazabicyclo[3.2.2]nonan-4-yl)-N-(3-hydroxy-2,2-dimethylpropyl)-5-nitroisonicotinamide.

Procedure 31

Intermediate 31A: 5-Amino-2-(1,4-diazabicyclo[3.2.2]nonan-4-yl)-N-methylisonicotinamide

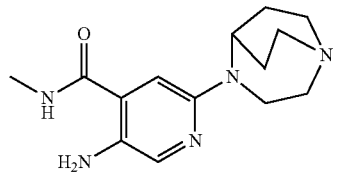

To a solution of 2-(1,4-diazabicyclo[3.2.2]nonan-4-yl)-N-methyl-5-nitroisonicotinamide (Intermediate 28A) (50 mg, 0.16 mmol) in methanol (0.3 mL) under nitrogen was added palladium on carbon (25 mg). Reaction subjected to a hydrogen atmosphere and stirred overnight. The reaction mixture was filtered and concentrated to afford 5-amino-2-(1,4-diazabicyclo[3.2.2]nonan-4-yl)-N-methylisonicotinamide.

Similarly Prepared were

Intermediate 31B: 5-Amino-2-(1,4-diazabicyclo[3.2.2]nonan-4-yl)isonicotinamide (from Intermediate 28B)

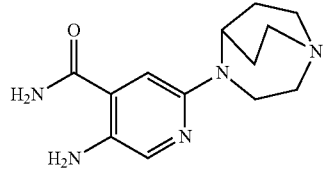

Intermediate 31C: 5-Amino-2-(1,4-diazabicyclo[3.2.2]nonan-4-yl)-N-(3-hydroxy-2,2-dimethylpropyl)isonicotinamide (from Intermediate 30A)

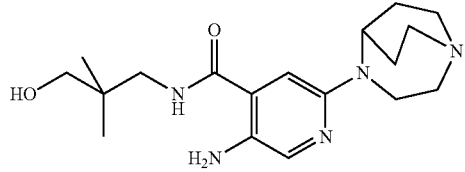 [SMILES: CC(C)(CO)CNC(=O)c1cc(N2CCN3CCC2CC3)ncc1N]

Intermediate 31D: 2-Amino-5-((1S,4S)-5-methyl-2,5-diazabicyclo[2.2.1]heptan-2-yl)benzamide (from Intermediate 27B)

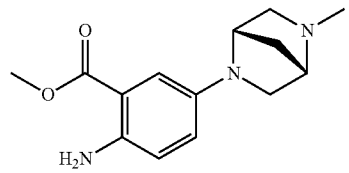

Procedure 32

Intermediate 32A: 2-Amino-5-hydroxy-N-methylbenzamide

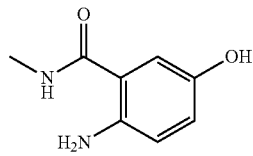

A solution of 6-hydroxy-1H-benzo[d][1,3]oxazine-2,4-dione (500 mg, 2.79 mmol) in ethanol (20 mL) was cooled to 0° C. and methylamine solution (33% in ethanol, 2.92 mL, 27.9 mmol) added and the reaction stirred for 3 days. The solvent was removed under reduced pressure and the product purified by silica chromatography, eluent 5% methanol in dichloromethane to yield 2-amino-5-hydroxy-N-methylbenzamide (280 mg, 1.68 mmol).

Similarly Prepared was

Intermediate 32B: 2-Amino-5-hydroxy-N-ethylbenzamide

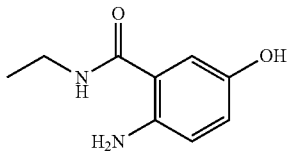

Procedure 33

Intermediate 33A: 2-(3-Chlorophenyl)-6-hydroxy-3-methylquinazolin-4(3H)-one

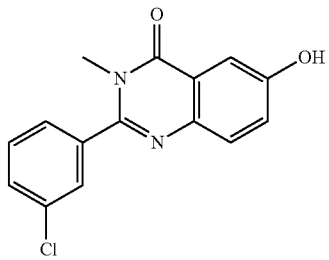 [SMILES: Cn1c(-c2cccc(Cl)c2)nc2ccc(O)cc2c1=O]

To a solution of 2-amino-5-hydroxy-N-methylbenzamide (Intermediate 32A) (280 mg, 1.68 mmol) and 3-chlorobenzaldehyde (0.23 mL, 2.02 mmol) in ethanol (10 mL) was added a catalytic amount of acetic acid (0.07 mL) and the mixture heated under reflux for 23 h. The reaction was cooled before manganese (iv) oxide (225 mg, 1.68 mmol) was added and the reaction heated under reflux until complete by lc/ms. On cooling the reaction was filtered and the filtrate evaporated to dryness to afford 2-(3-chlorophenyl)-6-hydroxy-3-methylquinazolin-4(3H)-one (450 mg, 1.57 mmol).

MS (ESI) m/z 287 [M+H]+

Similarly Prepared were

Intermediate 33B: 3-Methyl-6-hydroxyquinazolin-4(3H)-one (from Intermediate 32A)

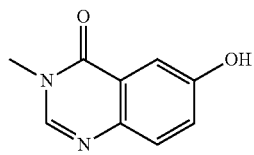

Intermediate 33C: 3-Ethyl-6-hydroxy-2-phenylquinazolin-4(3H)-one (from Intermediate 32B)

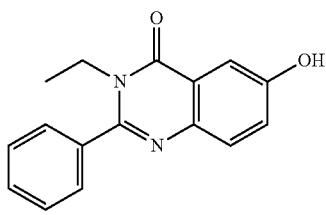 [SMILES: CCn1c(-c2ccccc2)nc2ccc(O)cc2c1=O]

SYNTHESIS OF EXAMPLES ACCORDING TO THE INVENTION

Example 1A 6-(1,4-Diazabicyclo[3.2.2]nonan-4-yl)-quinazolin-4(3H)-one

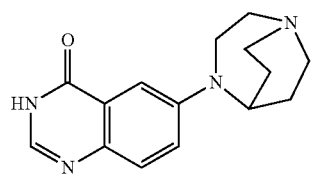 [SMILES: O=c1[nH]cnc2ccc(N3CCN4CCC3CC4)cc12]

A mixture of 6-bromoquinazolin-4(3H)-one (0.50 g, 2.22 mmol), 1,4-diazabicyclo[3.2.2]nonane hydrochloride (0.44 g, 2.22 mmol), triethylamine (0.45 g, 4.44 mmol), potassium tert-butoxide (0.25 g, 2.22 mmol), dicyclohexyl(2',4',6'-triisopropylbiphenyl-2-yl)phosphine (1.06 g, 2.22 mmol) and tris(dibenzyllideneacetone)dipalladium (0) (0.41 g, 0.44 mmol) in Tetrahydrofuran (15 mL) was heated in the microwave at 120° C. for 30 mins. The solvent was evaporated off and to the residue was added methanol and the mixture acidified with acetic acid then loaded on to a 5 g SCX column. The mixture was purified on silica (25 g SNAP column on SP4) eluting with dichloromethane to 60/40 dichloromethane/(2M ammonia in methanol) to afford 6-(1,4-diazabicyclo[3.2.2]nonan-4-yl)quinazolin-4(3H)-one (18.5 mg, 0.07 mmol).

MS (ESI) m/z 271.2 [M+H]+

Similarly Prepared were

Example 1B 7-(1,4-Diazabicyclo[3.2.2]nonan-4-yl)2-methylisoquinolin-1(2H)-one (from Intermediate 19B)

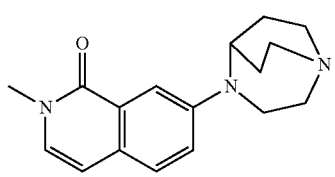 [SMILES: Cn1ccc2ccc(N3CCN4CCC3CC4)cc2c1=O]

MS (ESI) m/z 284 [M+H]+

Example 1C (R)-6-(1,4-Diazabicyclo[3.2.1]octan-4-yl)-3-methylquinazolin-4(3H)-one (from Intermediate 19A)

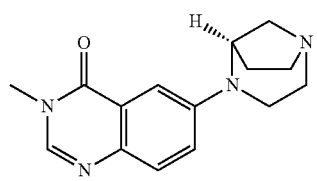 [SMILES: Cn1cnc2ccc(N3CCN4CC[C@@H]3C4)cc2c1=O]

MS (ESI) m/z 271.2 [M+H]+

Example 1D (S)-6-(1,4-Diazabicyclo[3.2.1]octan-4-yl)-3-methylquinazolin-4(3H)-one (from Intermediate 19A)

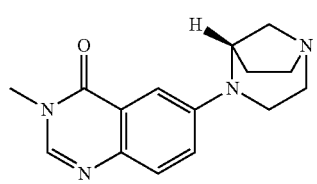 [SMILES: Cn1cnc2ccc(N3CCN4CC[C@H]3C4)cc2c1=O]

MS (ESI) m/z 271.2 [M+H]+

Example 2A 2-(6-(1,4-Diazabicyclo[3.2.2]nonan-4-yl)-2-(3-chloro-5-fluorophenyl)-4-oxoquinazolin-3(4H)-yl)-N-isopropylacetamide

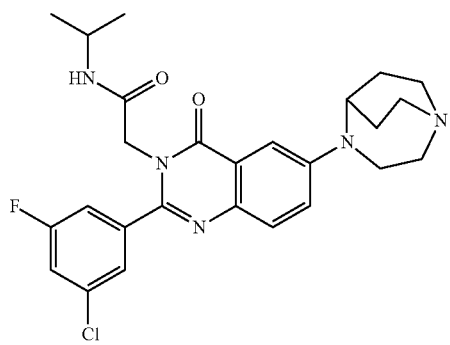 [SMILES: CC(C)NC(=O)Cn1c(-c2cc(F)cc(Cl)c2)nc2ccc(N3CCN4CCC3CC4)cc2c1=O]

2-Amino-5-(1,4-diazabicyclo[3.2.2]nonan-4-yl)-N-(2-(isopropylamino)-2-oxoethyl)benzamide (Intermediate 7A) (70 mg, 0.20 mmol) was dissolved in ethanol (2 mL) before addition of 3-chloro-5-fluorobenzaldehyde (46.3 mg, 0.29 mmol) followed by 2 drops of acetic acid. The resulting solution was sealed in a Reactivial® and heated at 95° C. for 24 hours. Reaction mixture was then cooled to room temperature and diluted with methanol before loading directly onto a 1 g SCX cartridge. The crude material was purified by SCX and concentrated under reduced pressure. The resultant product was re-dissolved in dichloromethane (2 mL), manganese dioxide (33.8 mg, 0.39 mmol) was added and reaction stirred overnight. The sample was then washed with water (5 mL) and extracted into dichloromethane. The organics were separated using a hydrophobic frit. The solvent was removed under reduced pressure and then re-dissolved in methanol (1 mL) and purified by preparative-HPLC. Purified sample was free-based using 500 mg SCX cartridge to afford 2-(6-(1,4-Diazabicyclo[3.2.2]nonan-4-yl)-2-(3-chloro-5-fluorophenyl)-4-oxoquinazolin-3(4H)-yl)-N-isopropylacetamide (9.0 mg, 0.018 mmol) 9% yield.

MS (ESI) m/z 498.0 [M+H]+

Similarly Prepared were

Example 2B 2-(6-(1,4-Diazabicyclo[3.2.2]nonan-4-yl)-4-oxo-2-p-tolylquinazolin-3(4H)-yl)-N-isopropylacetamide (from Intermediate 7A)

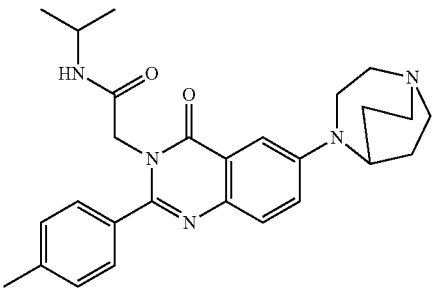 [SMILES: Cc1ccc(-c2nc3ccc(N4CCN5CCC4CC5)cc3c(=O)n2CC(=O)NC(C)C)cc1]

MS (ESI) m/z 460.2 [M+H]+

Example 2C 2-(6-(1,4-Diazabicyclo[3.2.2]nonan-4-yl)-4-oxo-2-phenylquinazolin-3(4H)-yl)-N-isopropylacetamide (from Intermediate 7A)

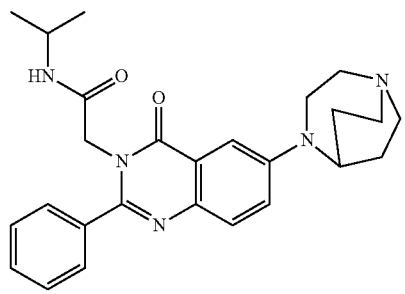 [SMILES: CC(C)NC(=O)Cn1c(-c2ccccc2)nc2ccc(N3CCN4CCC3CC4)cc2c1=O]

MS (ESI) m/z 446.2 [M+H]+

Example 2D 2-(6-(1,4-Diazabicyclo[3.2.2]nonan-4-yl)-2-(2-fluorophenyl)-4-oxoquinazolin-3(4H)-yl)-N-isopropylacetamide (from Intermediate 7A)

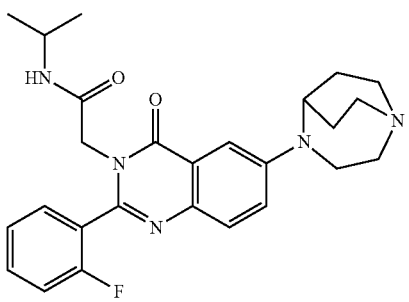 [SMILES: CC(C)NC(=O)Cn1c(-c2ccccc2F)nc2ccc(N3CCN4CCC3CC4)cc2c1=O]

MS (ESI) m/z 464.2 [M+H]+

Example 2E 2-(6-(1,4-Diazabicyclo[3.2.2]nonan-4-yl)-2-(4-fluorophenyl)-4-oxoquinazolin-3(4H)-yl)-N-isopropylacetamide (from Intermediate 7A)

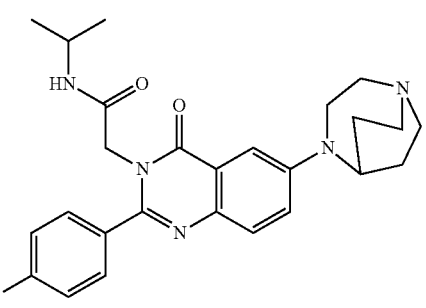

MS (ESI) m/z 464.2 [M+H]+

Example 2F 2-(6-(1,4-Diazabicyclo[3.2.2]nonan-4-yl)-4-oxo-2-m-tolylquinazolin-3(4H)-yl)-N-isopropylacetamide (from Intermediate 7A)

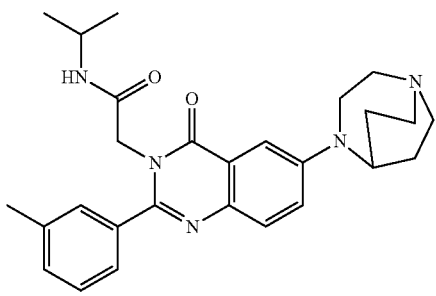 [SMILES: Cc1cccc(-c2nc3ccc(N4CCN5CCC4CC5)cc3c(=O)n2CC(=O)NC(C)C)c1]

MS (ESI) m/z 460.2 [M+H]+

Example 2G 2-(6-(1,4-Diazabicyclo[3.2.2]nonan-4-yl)-2-(3-cyanophenyl)-4-oxoquinazolin-3(4H)-yl)-N-isopropylacetamide (from Intermediate 7A)

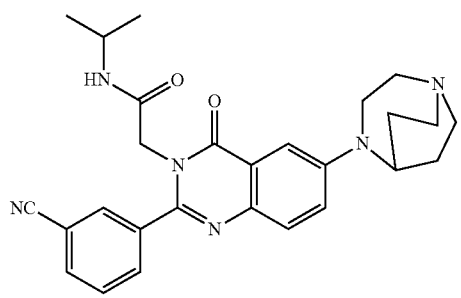 [SMILES: CC(C)NC(=O)Cn1c(-c2cccc(C#N)c2)nc2ccc(N3CCN4CCC3CC4)cc2c1=O]

MS (ESI) m/z 471.2 [M+H]+

Example 2H 2-(6-(1,4-Diazabicyclo[3.2.2]nonan-4-yl)-4-oxo-2-(3-(trifluoromethyl)phenyl)quinazolin-3(4H)-yl)-N-isopropylacetamide (from Intermediate 7A)

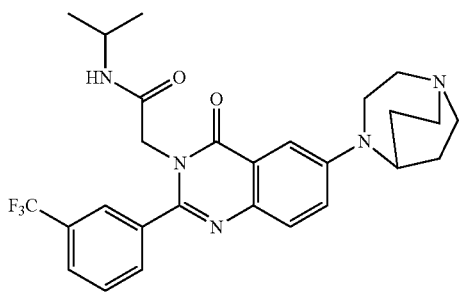 [SMILES: CC(C)NC(=O)Cn1c(-c2cccc(C(F)(F)F)c2)nc2ccc(N3CCN4CCC3CC4)cc2c1=O]

MS (ESI) m/z 514.2 [M+H]+

Example 2I 2-(6-(1,4-Diazabicyclo[3.2.2]nonan-4-yl)-4-oxo-2-(3-(trifluoromethoxy)phenyl)quinazolin-3(4H)-yl)-N-isopropylacetamide (from Intermediate 7A)

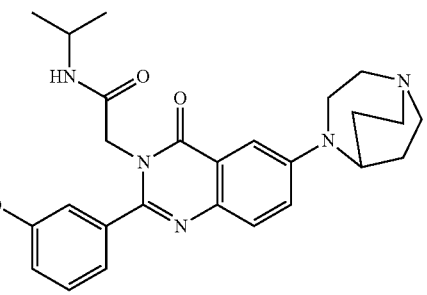

MS (ESI) m/z 530.2 [M+H]+

Example 2J 2-(6-(1,4-Diazabicyclo[3.2.2]nonan-4-yl)-2-(3-ethoxyphenyl)-4-oxoquinazolin-3(4H)-yl)-N-isopropylacetamide (from Intermediate 7A)

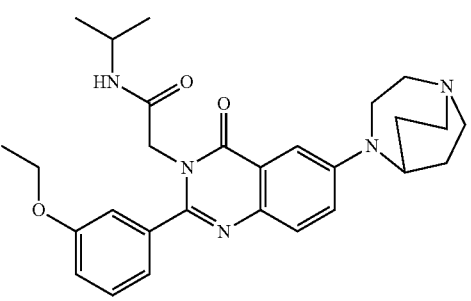 [SMILES: CCOc1cccc(-c2nc3ccc(N4CCN5CCC4CC5)cc3c(=O)n2CC(=O)NC(C)C)c1]

MS (ESI) m/z 490.2 [M+H]+

Example 2K 2-(6-(1,4-Diazabicyclo[3.2.2]nonan-4-yl)-2-(3-fluorophenyl)-4-oxoquinazolin-3(4H)-yl)-N-isopropylacetamide (from Intermediate 7A)

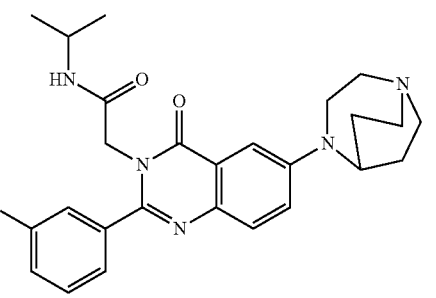

MS (ESI) m/z 464.2 [M+H]+

Example 2L 2-(6-(1,4-Diazabicyclo[3.2.2]nonan-4-yl)-2-(3,5-difluorophenyl)-4-oxoquinazolin-3(4H)-yl)-N-isopropylacetamide (from Intermediate 7A)

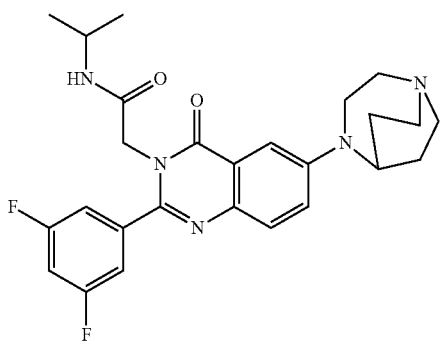 [SMILES: CC(C)NC(=O)Cn1c(-c2cc(F)cc(F)c2)nc2ccc(N3CCN4CCC3CC4)cc2c1=O]

MS (ESI) m/z 482.2 [M+H]+

Example 2M 2-(6-(1,4-Diazabicyclo[3.2.2]nonan-4-yl)-2-(2,5-difluorophenyl)-4-oxoquinazolin-3(4H)-yl)-N-isopropylacetamide (from Intermediate 7A)

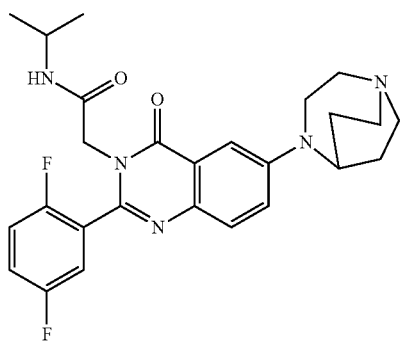 [SMILES: CC(C)NC(=O)Cn1c(-c2cc(F)ccc2F)nc2ccc(N3CCN4CCC3CC4)cc2c1=O]

MS (ESI) m/z 482.2 [M+H]+

Example 2N 2-(6-(1,4-Diazabicyclo[3.2.2]nonan-4-yl)-2-(2,3-difluorophenyl)-4-oxoquinazolin-3(4H)-yl)-N-isopropylacetamide (from Intermediate 7A)

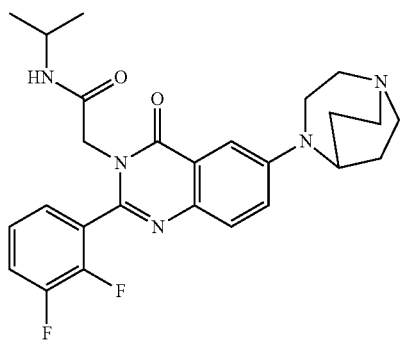 [SMILES: CC(C)NC(=O)Cn1c(-c2cccc(F)c2F)nc2ccc(N3CCN4CCC3CC4)cc2c1=O]

MS (ESI) m/z 482.2 [M+H]+

Example 2O 2-(6-(1,4-Diazabicyclo[3.2.2]nonan-4-yl)-2-(3-chloro-2-fluorophenyl)-4-oxoquinazolin-3(4H)-yl)-N-isopropylacetamide (from Intermediate 7A)

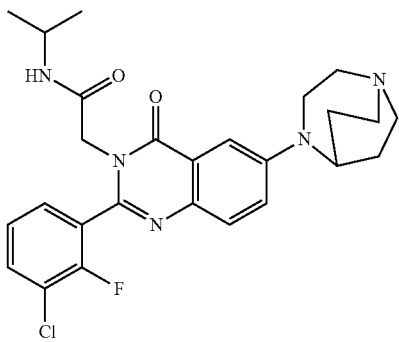 [SMILES: CC(C)NC(=O)Cn1c(-c2cccc(Cl)c2F)nc2ccc(N3CCN4CCC3CC4)cc2c1=O]

MS (ESI) m/z 498.2 [M+H]+

Example 2P 2-(6-(1,4-Diazabicyclo[3.2.2]nonan-4-yl)-2-(3-chloro-2-chlorophenyl)-4-oxoquinazolin-3(4H)-yl)-N-isopropylacetamide (from Intermediate 7A)

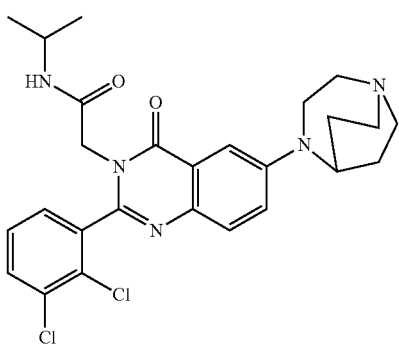 [SMILES: CC(C)NC(=O)Cn1c(-c2cccc(Cl)c2Cl)nc2ccc(N3CCN4CCC3CC4)cc2c1=O]

MS (ESI) m/z 514 [M+H]+

Example 2Q 2-(6-(1,4-Diazabicyclo[3.2.2]nonan-4-yl)-2-(3,4-difluorophenyl)-4-oxoquinazolin-3(4H)-yl)-N-isopropylacetamide (from Intermediate 7A)

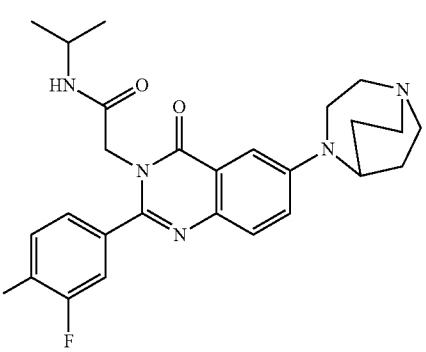

MS (ESI) m/z 482.2 [M+H]+

Example 2R 2-(6-(1,4-Diazabicyclo[3.2.2]nonan-4-yl)-2-(5-chloro-2-fluorophenyl)-4-oxoquinazolin-3(4H)-yl)-N-isopropylacetamide (from Intermediate 7A)

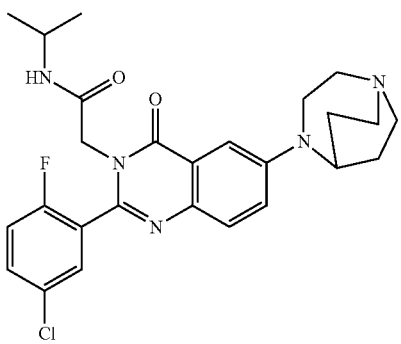 [SMILES: CC(C)NC(=O)Cn1c(-c2cc(Cl)ccc2F)nc2ccc(N3CCN4CCC3CC4)cc2c1=O]

MS (ESI) m/z 498 [M+H]+

Example 2S 2-(6-(1,4-Diazabicyclo[3.2.2]nonan-4-yl)-4-oxoquinazolin-3(4H)-yl)-N-isopropylacetamide (from Intermediate 7A)

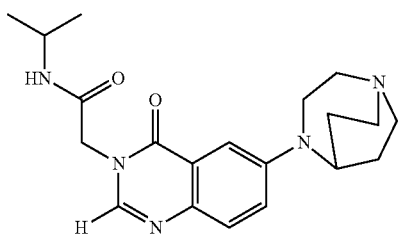 [SMILES: CC(C)NC(=O)Cn1cnc2ccc(N3CCN4CCC3CC4)cc2c1=O]

MS (ESI) m/z 370.2 [M+H]+

Example 2T 2-(6-(1,4-Diazabicyclo[3.2.2]nonan-4-yl)-2-methyl-4-oxoquinazolin-3(4H)-yl)-N-isopropylacetamide (from Intermediate 7A)

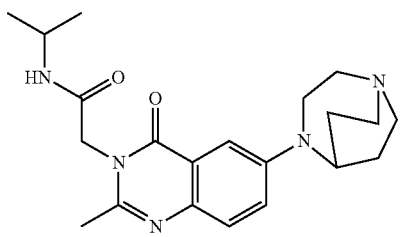 [SMILES: Cc1nc2ccc(N3CCN4CCC3CC4)cc2c(=O)n1CC(=O)NC(C)C]

MS (ESI) m/z 385.2 [M+H]+

Example 2U 2-(6-(1,4-Diazabicyclo[3.2.2]nonan-4-yl)-2-isopropyl-4-oxoquinazolin-3(4H)-yl)-N-isopropylacetamide (from Intermediate 7A)

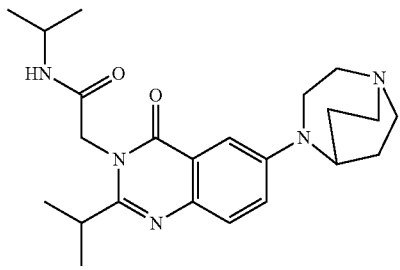 [SMILES: CC(C)NC(=O)Cn1c(C(C)C)nc2ccc(N3CCN4CCC3CC4)cc2c1=O]

MS (ESI) m/z 412.2 [M+H]+

Example 2V 2-(6-(1,4-Diazabicyclo[3.2.2]nonan-4-yl)-2-cyclopropyl-4-oxoquinazolin-3(4H)-yl)-N-isopropylacetamide (from Intermediate 7A)

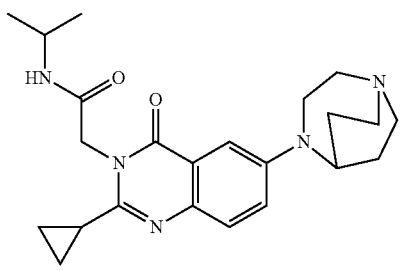 [SMILES: CC(C)NC(=O)Cn1c(C2CC2)nc2ccc(N3CCN4CCC3CC4)cc2c1=O]

MS (ESI) m/z 410.2 [M+H]+

Example 2W 2-(6-(1,4-Diazabicyclo[3.2.2]nonan-4-yl)-2-cyclopentyl-4-oxoquinazolin-3(4H)-yl)-N-isopropylacetamide (from Intermediate 7A)

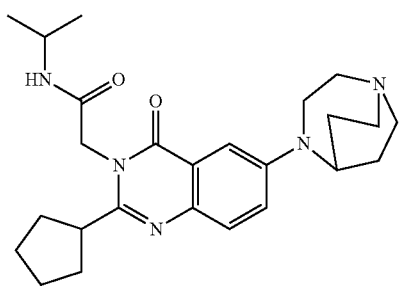 [SMILES: CC(C)NC(=O)Cn1c(C2CCCC2)nc2ccc(N3CCN4CCC3CC4)cc2c1=O]

MS (ESI) m/z 438.2 [M+H]+

Example 2X 2-(6-(1,4-Diazabicyclo[3.2.2]nonan-4-yl)-4-oxo-2-(3,3,3-trifluoropropyl)quinazolin-3(4H)-yl)-N-isopropylacetamide (from Intermediate 7A)

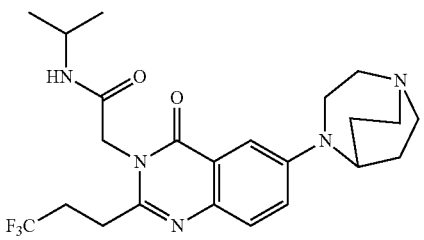 [SMILES: CC(C)NC(=O)Cn1c(CCC(F)(F)F)nc2ccc(N3CCN4CCC3CC4)cc2c1=O]

MS (ESI) m/z 467.2 [M+H]+

Example 2Y 2-(6-(1,4-Diazabicyclo[3.2.2]nonan-4-yl)-2-sec-butyl-4-oxoquinazolin-3(4H)-yl)-N-isopropylacetamide (from Intermediate 7A)

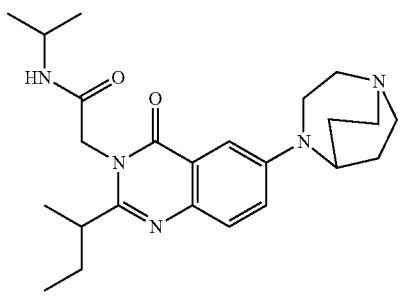 [SMILES: CCC(C)c1nc2ccc(N3CCN4CCC3CC4)cc2c(=O)n1CC(=O)NC(C)C]

MS (ESI) m/z 427.2 [M+H]+

Example 2Z 2-(6-(1,4-Diazabicyclo[3.2.2]nonan-4-yl)-2-isobutyl-4-oxoquinazolin-3(4H)-yl)-N-isopropylacetamide (from Intermediate 7A)

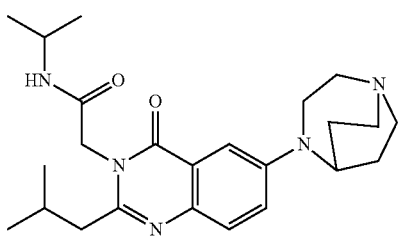 [SMILES: CC(C)Cc1nc2ccc(N3CCN4CCC3CC4)cc2c(=O)n1CC(=O)NC(C)C]

MS (ESI) m/z 426.2 [M+H]+

Example 2AA 2-(6-(1,4-Diazabicyclo[3.2.2]nonan-4-yl)-2-ethyl-4-oxoquinazolin-3(4H)-yl)-N-isopropylacetamide (from Intermediate 7A)

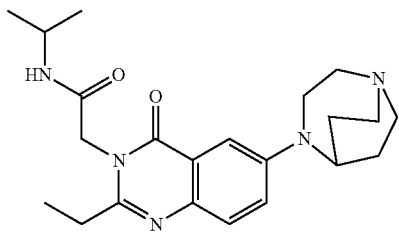 [SMILES: CCc1nc2ccc(N3CCN4CCC3CC4)cc2c(=O)n1CC(=O)NC(C)C]

MS (ESI) m/z 398.2 [M+H]+

Example 2AB 2-(6-(1,4-Diazabicyclo[3.2.2]nonan-4-yl)-2-tert-butyl-4-oxoquinazolin-3(4H)-yl)-N-isopropylacetamide (from Intermediate 7A)

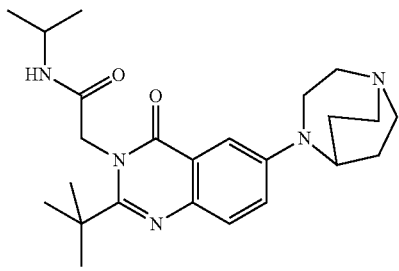 [SMILES: CC(C)NC(=O)Cn1c(C(C)(C)C)nc2ccc(N3CCN4CCC3CC4)cc2c1=O]

MS (ESI) m/z 426.2 [M+H]+

Example 2AC 2-(6-(1,4-Diazabicyclo[3.2.2]nonan-4-yl)-2-cyclohexyl-4-oxoquinazolin-3(4H)-yl)-N-isopropylacetamide (from Intermediate 7A)

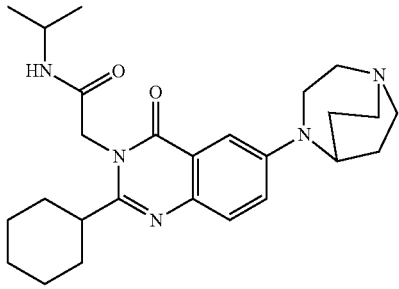 [SMILES: CC(C)NC(=O)Cn1c(C2CCCCC2)nc2ccc(N3CCN4CCC3CC4)cc2c1=O]

MS (ESI) m/z 453.2 [M+H]+

Example 2AD 2-(2-(3-Chlorophenyl)-6-(8-methyl-8-azabicyclo[3.2.1]octan-3-ylamino)-4-oxoquinazolin-3(4H)-yl)-N-isopropylacetamide (from Intermediate 7C)

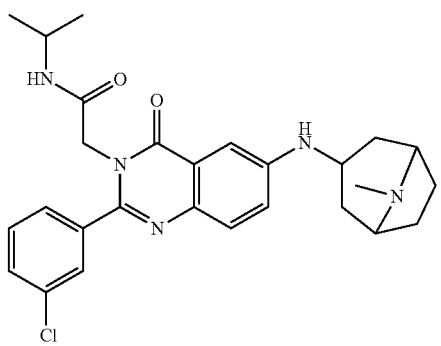 [SMILES: CC(C)NC(=O)Cn1c(-c2cccc(Cl)c2)nc2ccc(NC3CC4CCC(C3)N4C)cc2c1=O]

MS (ESI) m/z 494.2 [M+H]+

Example 2AE 2-(2-Fluorophenyl)-3-methyl-6-(5-methylhexahydro-pyrrolo[3,4-c]pyrrole-2(1H)-yl)quinazolin-4(3H)-one (from Intermediate 8A)

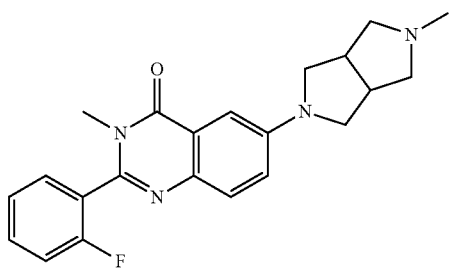 [SMILES: CN1CC2CN(c3ccc4nc(-c5ccccc5F)n(C)c(=O)c4c3)CC2C1]

MS (ESI) m/z 380.2 [M+H]+

Example 2AF 2-(3-Chlorophenyl)-3-methyl-6-(5-methylhexahydropyrrolo[3,4-c]pyrrol-2(1H)-yl)quinazolin-4(3H)-one (from Intermediate 8A)

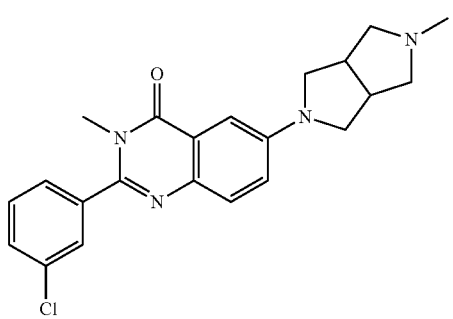 [SMILES: CN1CC2CN(c3ccc4nc(-c5cccc(Cl)c5)n(C)c(=O)c4c3)CC2C1]

MS (ESI) m/z 395 [M+H]+

Example 2AG 3-(3-Methyl-6-(5-methylhexahydropyrrolo[3,4-c]pyrrol-2(1H)-yl)-4-oxo-3,4-dihydroquinazolin-2-yl)benzonitrile (from Intermediate 8A)

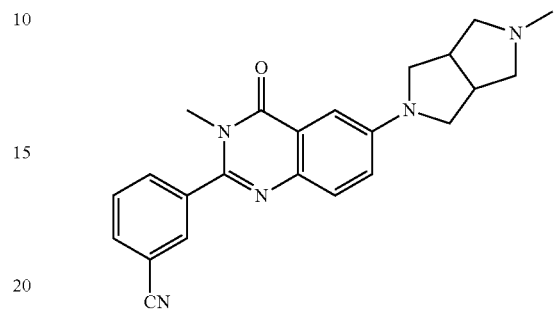

MS (ESI) m/z 386.2 [M+H]+

Example 2AH

2-Cyclopropyl-3-methyl-6-(5-methylhexahydropyrrolo[3,4-c]pyrrol-2(1H)-yl)quinazolin-4(3H)-one (from Intermediate 8A)

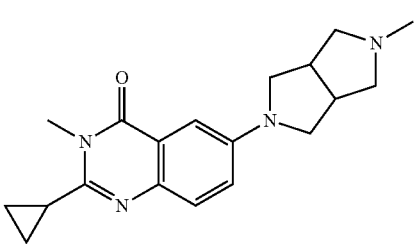 [SMILES: CN1CC2CN(c3ccc4nc(C5CC5)n(C)c(=O)c4c3)CC2C1]

MS (ESI) m/z 325.2 [M+H]+

Example 2AI 2-(2-Fluorophenyl-3-methyl-6-((1S,4S)-5-methyl-2,5-diazabicyclo[2.2.1]heptan-2-yl)quinazolin-4(3H)-one (from Intermediate 8B)

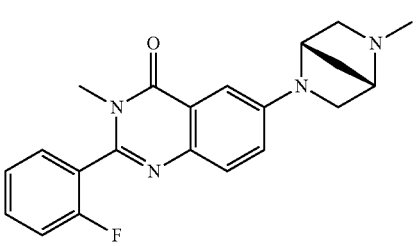 [SMILES: CN1C[C@@H]2C[C@H]1CN2c1ccc2nc(-c3ccccc3F)n(C)c(=O)c2c1]

MS (ESI) m/z 366.0 [M+H]+

Example 2AJ 2-(3-Chlorophenyl)-6-(1,4-diazabicyclo[3.2.2]nonan-4-yl)-quinazolin-4(3H)-one (from Intermediate 8D)

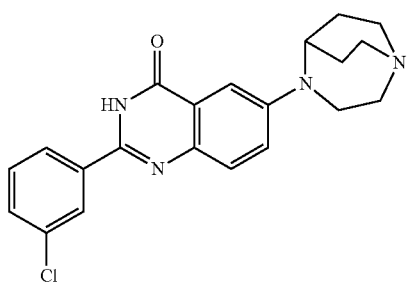 [SMILES: O=c1[nH]c(-c2cccc(Cl)c2)nc2ccc(N3CCN4CCC3CC4)cc12]

MS (ESI) m/z 381.5 [M+H]+

Example 2AK 6-(1,4-Diazabicyclo[3.2.2]nonan-4-yl)-2-(3-chlorophenyl)-3-(2-methoxyethyl)quinazolin-4(3H)-one (from Intermediate 8G)

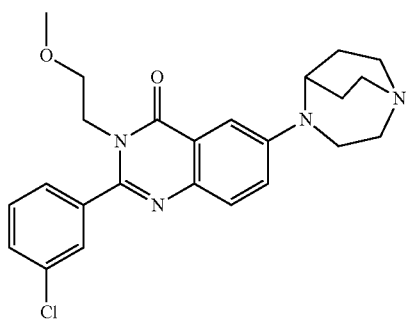 [SMILES: COCCn1c(-c2cccc(Cl)c2)nc2ccc(N3CCN4CCC3CC4)cc2c1=O]

MS (ESI) m/z 439.0 [M+H]+

Example 2AL 6-(1,4-Diazabicyclo[3.2.2]nonan-4-yl)-2-(3-chlorophenyl)-3-methylquinazolin-4(3H)-one (from Intermediate 7F)

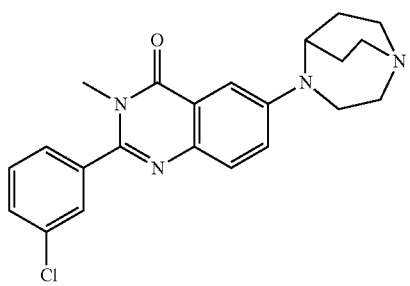 [SMILES: Cn1c(-c2cccc(Cl)c2)nc2ccc(N3CCN4CCC3CC4)cc2c1=O]

MS (ESI) m/z 395.0 [M+H]+

Example 2AM 6-(1,4-Diazabicyclo[3.2.2]nonan-4-yl)-2-(3-chlorophenyl)-3-ethylquinazolin-4(3H)-one (from Intermediate 7G)

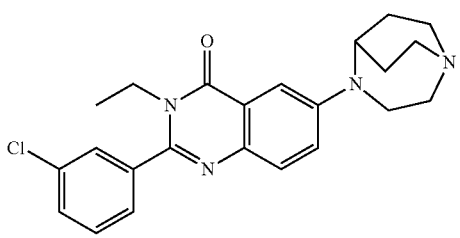 [SMILES: CCn1c(-c2cccc(Cl)c2)nc2ccc(N3CCN4CCC3CC4)cc2c1=O]

MS (ESI) m/z 409.2 [M+H]+

Example 2AN 6-(1,4-Diazabicyclo[3.2.2]nonan-4-yl)-2-(3-chlorophenyl)-3-propylquinazolin-4(3H)-one (from Intermediate 7H)

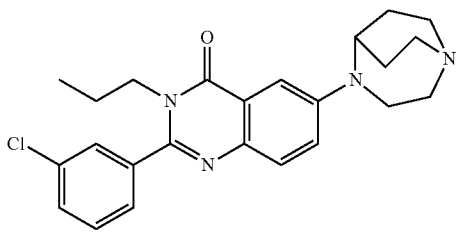 [SMILES: CCCn1c(-c2cccc(Cl)c2)nc2ccc(N3CCN4CCC3CC4)cc2c1=O]

MS (ESI) m/z 423.2 [M+H]+

Example 2AO 6-(1,4-Diazabicyclo[3.2.2]nonan-4-yl)-2-ethyl-3-propylquinazolin-4(3H)-one (from Intermediate 7H)

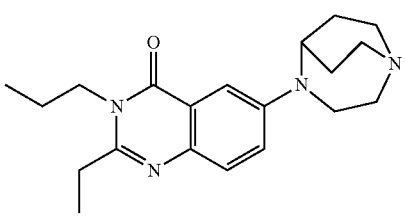 [SMILES: CCCn1c(CC)nc2ccc(N3CCN4CCC3CC4)cc2c1=O]

MS (ESI) m/z 341.2 [M+H]+

87

Example 2AP 6-(1,4-Diazabicyclo[3.2.2]nonan-4-yl)-2-(3-chlorophenyl)-3-isobutylquinazolin-4(3H)-one (from Intermediate 7I)

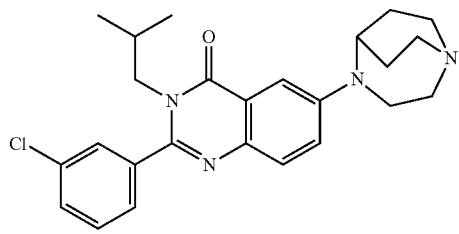 [SMILES: CC(C)Cn1c(-c2cccc(Cl)c2)nc2ccc(N3CCN4CCC3CC4)cc2c1=O]

MS (ESI) m/z 437.2 [M+H]+

Example 2AQ 6-(1,4-Diazabicyclo[3.2.2]nonan-4-yl)-2-(3-chlorophenyl)-3-(3-hydroxy-3-methylbutyl)-quinazolin-4(3H)-one (from Intermediate 7O)

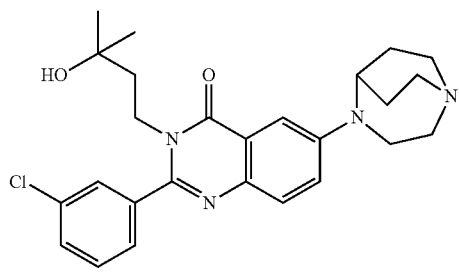 [SMILES: CC(C)(O)CCn1c(-c2cccc(Cl)c2)nc2ccc(N3CCN4CCC3CC4)cc2c1=O]

MS (ESI) m/z 467.2 [M+H]+

Example 2AR 6-(1,4-Diazabicyclo[3.2.2]nonan-4-yl)-2-(3-chlorophenyl)-3-((tetrahydro-2H-pyran-4-yl)methyl)-quinazolin-4(3H)-one (from Intermediate 7N)

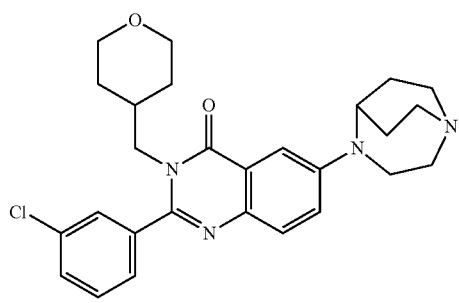 [SMILES: O=c1c2cc(N3CCN4CCC3CC4)ccc2nc(-c2cccc(Cl)c2)n1CC1CCOCC1]

MS (ESI) m/z 479.2 [M+H]+

88

Example 2AS 6-(1,4-Diazabicyclo[3.2.2]nonan-4-yl)-2-(3-chlorophenyl)-3-(propan-3-ol)-quinazolin-4(3H)-one (from Intermediate 7P)

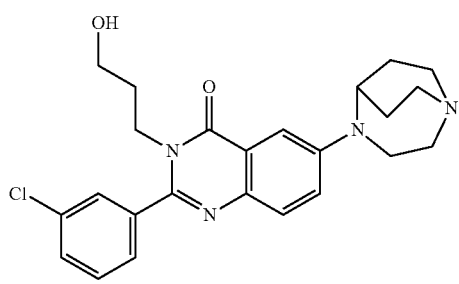 [SMILES: O=c1c2cc(N3CCN4CCC3CC4)ccc2nc(-c2cccc(Cl)c2)n1CCCO]

MS (ESI) m/z 439.0 [M+H]+

Example 2AT 6-(1,4-Diazabicyclo[3.2.2]nonan-4-yl)-2-ethyl-3-((tetrahydro-2H-pyran-4-yl)methyl)-quinazolin-4(3H)-one (from Intermediate 7N)

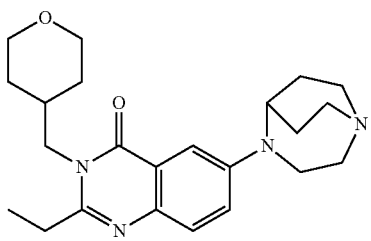 [SMILES: CCc1nc2ccc(N3CCN4CCC3CC4)cc2c(=O)n1CC1CCOCC1]

MS (ESI) m/z 397.2 [M+H]+

Example 2AU 6-(1,4-Diazabicyclo[3.2.2]nonan-4-yl)-2-(3-chlorophenyl)-3-(cyclopropylmethyl)-quinazolin-4(3H)-one (from Intermediate 7J)

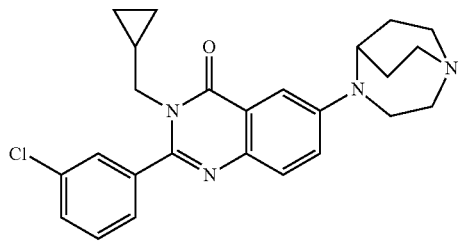 [SMILES: O=c1c2cc(N3CCN4CCC3CC4)ccc2nc(-c2cccc(Cl)c2)n1CC1CC1]

MS (ESI) m/z 435.2 [M+H]+

Example 2AV 6-(1,4-Diazabicyclo[3.2.2]nonan-4-yl)-2-ethyl-3-(cyclopropylmethyl)-quinazolin-4(3H)-one (from Intermediate 7J)

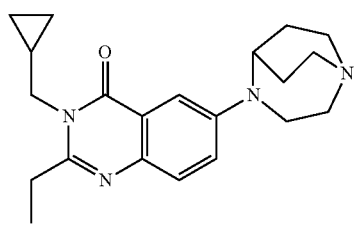 [SMILES: CCc1nc2ccc(N3CCN4CCC3CC4)cc2c(=O)n1CC1CC1]

MS (ESI) m/z 353.2 [M+H]+

Example 2AW 6-(1,4-Diazabicyclo[3.2.2]nonan-4-yl)-2-cyclopropyl-3-(cyclopropylmethyl)-quinazolin-4(3H)-one (from Intermediate 7J)

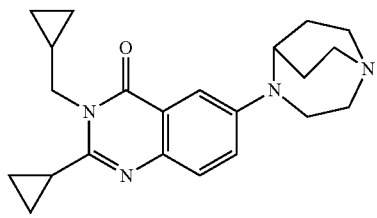 [SMILES: O=c1c2cc(N3CCN4CCC3CC4)ccc2nc(C2CC2)n1CC1CC1]

MS (ESI) m/z 365.2 [M+H]+

Example 2AX 6-(1,4-Diazabicyclo[3.2.2]nonan-4-yl)-2-(3-chloro-4-fluorophenyl)-3-(cyclopropylmethyl)-quinazolin-4(3H)-one (from Intermediate 7J)

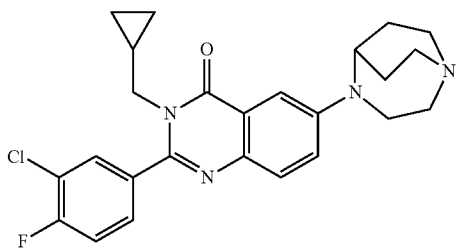 [SMILES: O=c1c2cc(N3CCN4CCC3CC4)ccc2nc(-c2ccc(F)c(Cl)c2)n1CC1CC1]

MS (ESI) m/z 453.2 [M+H]+

Example 2AY 6-(1,4-Diazabicyclo[3.2.2]nonan-4-yl)-2-(3-chlorophenyl)-3-isopropylquinazolin-4(3H)-one (from Intermediate 7K)

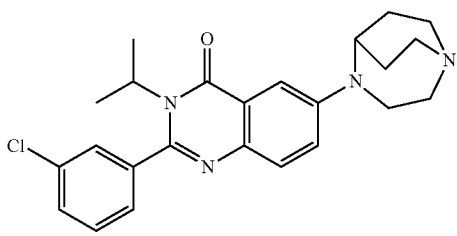 [SMILES: CC(C)n1c(-c2cccc(Cl)c2)nc2ccc(N3CCN4CCC3CC4)cc2c1=O]

MS (ESI) m/z 423.2 [M+H]+

Example 2AZ 6-(1,4-Diazabicyclo[3.2.2]nonan-4-yl)-2-cyclopropyl-3-isopropylquinazolin-4(3H)-one (from Intermediate 7K)

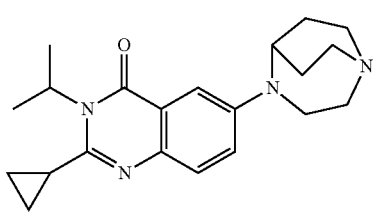 [SMILES: CC(C)n1c(C2CC2)nc2ccc(N3CCN4CCC3CC4)cc2c1=O]

MS (ESI) m/z 353.2 [M+H]+

Example 2AAA 6-(1,4-Diazabicyclo[3.2.2]nonan-4-yl)-2-(3-chlorophenyl)-3-((tetrahydro-2H-thiopyran-4-yl-1,1-dioxide)methyl)-quinazolin-4(3H)-one (from Intermediate 7Q)

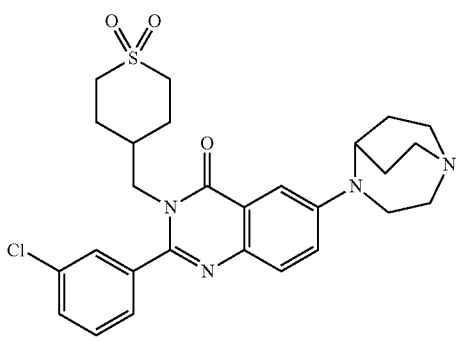 [SMILES: O=c1c2cc(N3CCN4CCC3CC4)ccc2nc(-c2cccc(Cl)c2)n1CC1CCS(=O)(=O)CC1]

MS (ESI) m/z 527.0 [M+H]+

Example 2AAB 6-(1,4-Diazabicyclo[3.2.2]nonan-4-yl)-2-(3-chlorophenyl)-3-((1-(hydroxymethyl)cyclobutyl)methyl)-quinazolin-4(3H)-one (from Intermediate 8E)

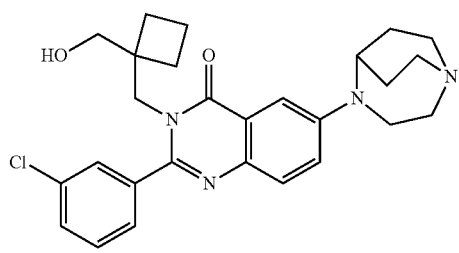 [SMILES: O=c1c2cc(N3CCN4CCC3CC4)ccc2nc(-c2cccc(Cl)c2)n1CC1(CO)CCC1]

MS (ESI) m/z 479.2 [M+H]+

Example 2AAC 6-(1,4-Diazabicyclo[3.2.2]nonan-4-yl)-2-cyclopropyl-3-methylquinazolin-4(3H)-one (from Intermediate 7F)

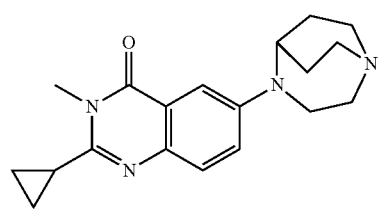 [SMILES: Cn1c(C2CC2)nc2ccc(N3CCN4CCC3CC4)cc2c1=O]

MS (ESI) m/z 325.2 [M+H]+

Example 2AAD 6-(1,4-Diazabicyclo[3.2.2]nonan-4-yl)-2-ethyl-3-methylquinazolin-4(3H)-one (from Intermediate 7F)

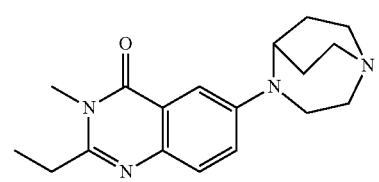 [SMILES: CCc1nc2ccc(N3CCN4CCC3CC4)cc2c(=O)n1C]

MS (ESI) m/z 313.2 [M+H]+

Example 2AAE 6-(1,4-Diazabicyclo[3.2.2]nonan-4-yl)-2-(2-fluorophenyl)-3-methylquinazolin-4(3H)-one (from Intermediate 7F)

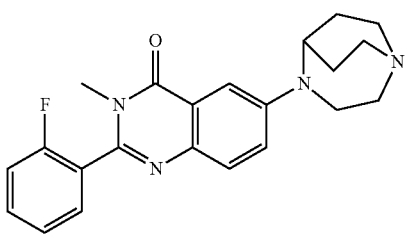 [SMILES: Cn1c(-c2ccccc2F)nc2ccc(N3CCN4CCC3CC4)cc2c1=O]

MS (ESI) m/z 379.2 [M+H]+

Example 2AAF 6-(1,4-Diazabicyclo[3.2.2]nonan-4-yl)-2-(3-fluorophenyl)-3-methylquinazolin-4(3H)-one (from Intermediate 7F)

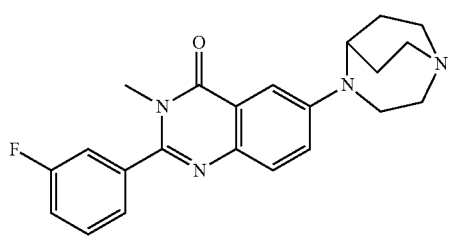 [SMILES: Cn1c(-c2cccc(F)c2)nc2ccc(N3CCN4CCC3CC4)cc2c1=O]

MS (ESI) m/z 379.2 [M+H]+

Example 2AAG 6-(1,4-Diazabicyclo[3.2.2]nonan-4-yl)-2-(4-fluorophenyl)-3-methylquinazolin-4(3H)-one (from Intermediate 7F)

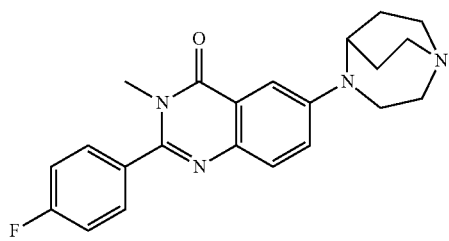 [SMILES: Cn1c(-c2ccc(F)cc2)nc2ccc(N3CCN4CCC3CC4)cc2c1=O]

MS (ESI) m/z 379.2 [M+H]+

Example 2AAH 6-(1,4-Diazabicyclo[3.2.2]nonan-4-yl)-2-(3-chloro-2-fluorophenyl)-3-methylquinazolin-4(3H)-one (from Intermediate 7F)

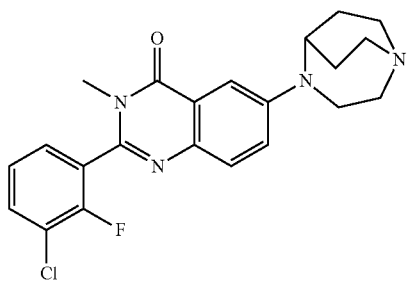 [SMILES: Cn1c(-c2cccc(Cl)c2F)nc2ccc(N3CCN4CCC3CC4)cc2c1=O]

MS (ESI) m/z 413.7 [M+H]+

Example 2AAI 6-(1,4-Diazabicyclo[3.2.2]nonan-4-yl)-2-(2,3-difluorophenyl)-3-methylquinazolin-4(3H)-one (from Intermediate 7F)

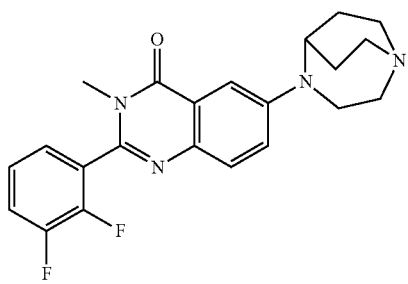

MS (ESI) m/z 397.2 [M+H]+

Example 2AAJ 6-(1,4-Diazabicyclo[3.2.2]nonan-4-yl)-2-(5-chloro-2-fluorophenyl)-3-methylquinazolin-4(3H)-one (from Intermediate 7F)

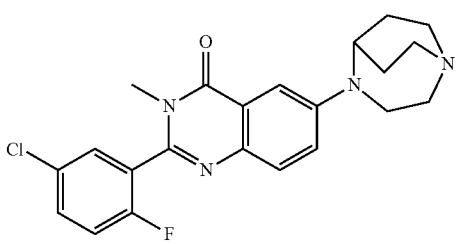 [SMILES: Cn1c(-c2cc(Cl)ccc2F)nc2ccc(N3CCN4CCC3CC4)cc2c1=O]

MS (ESI) m/z 413.7 [M+H]+

Example 2AAK 6-(1,4-Diazabicyclo[3.2.2]nonan-4-yl)-2-(2,5-difluorophenyl)-3-methylquinazolin-4(3H)-one (from Intermediate 7F)

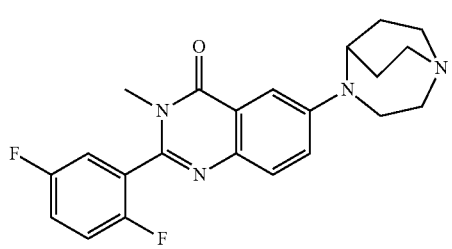 [SMILES: Cn1c(-c2cc(F)ccc2F)nc2ccc(N3CCN4CCC3CC4)cc2c1=O]

MS (ESI) m/z 397.2 [M+H]+

Example 2AAL 6-(1,4-Diazabicyclo[3.2.2]nonan-4-yl)-3-methyl-2-m-tolylquinazolin-4(3H)-one (from Intermediate 7F)

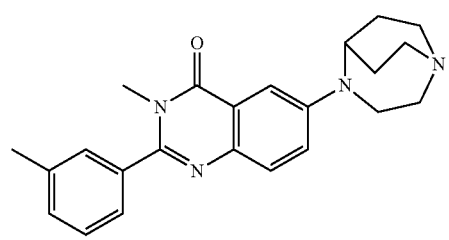

MS (ESI) m/z 375.5 [M+H]+

Example 2AAM 3-(6-(1,4-Diazabicyclo[3.2.2]nonan-4-yl)-3-methyl-4-oxo-3,4-dihydroquinazolin-2-yl)benzonitrile (from Intermediate 7F)

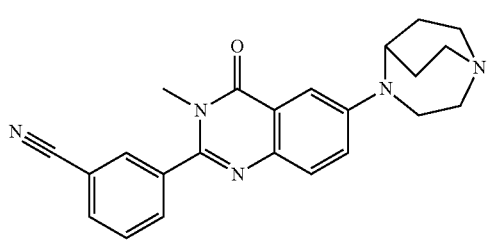 [SMILES: Cn1c(-c2cccc(C#N)c2)nc2ccc(N3CCN4CCC3CC4)cc2c1=O]

MS (ESI) m/z 386.2 [M+H]+

Example 2AAN 6-(1,4-Diazabicyclo[3.2.2]nonan-4-yl)-2-(2-fluorophenyl)quinazolin-4(3H)-one
(from Intermediate 8D)

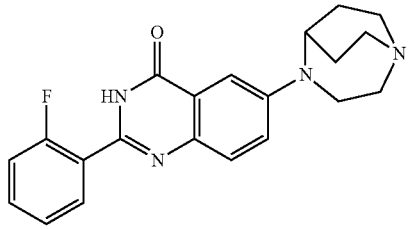 [SMILES: O=c1[nH]c(-c2ccccc2F)nc2ccc(N3CCN4CCC3CC4)cc12]

MS (ESI) m/z 365.0 [M+H]+

Example 2AAO 6-(1,4-Diazabicyclo[3.2.2]nonan-4-yl)-2-(3-fluorophenyl)quinazolin-4(3H)-one
(from Intermediate 8D)

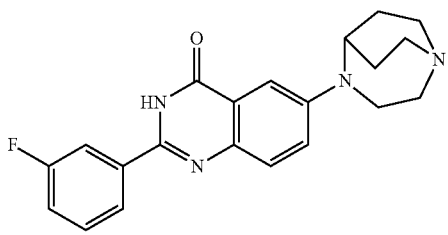 [SMILES: O=c1[nH]c(-c2cccc(F)c2)nc2ccc(N3CCN4CCC3CC4)cc12]

MS (ESI) m/z 365.2 [M+H]+

Example 2AAP 6-(1,4-Diazabicyclo[3.2.2]nonan-4-yl)-2-(3-chloro-2-fluorophenyl)quinazolin-4(3H)-one (from Intermediate 8D)

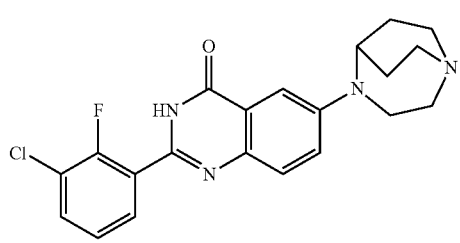 [SMILES: O=c1[nH]c(-c2cccc(Cl)c2F)nc2ccc(N3CCN4CCC3CC4)cc12]

MS (ESI) m/z 399.0 [M+H]+

Example 2AAQ 6-(1,4-Diazabicyclo[3.2.2]nonan-4-yl)-2-(2,3-difluorophenyl)quinazolin-4(3H)-one
(from Intermediate 8D)

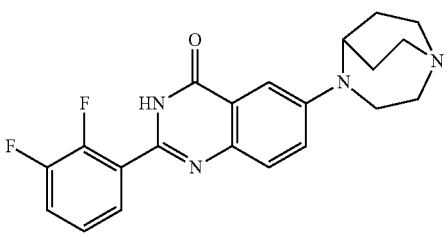

MS (ESI) m/z 383.2 [M+H]+

Example 2AAR 6-(1,4-Diazabicyclo[3.2.2]nonan-4-yl)-2-m-tolylquinazolin-4(3H)-one (from Intermediate 8D)

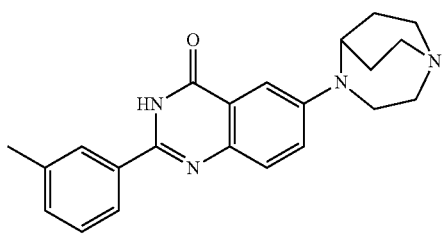 [SMILES: Cc1cccc(-c2nc3ccc(N4CCN5CCC4CC5)cc3c(=O)[nH]2)c1]

MS (ESI) m/z 361.2 [M+H]+

Example 2AAS 6-(1,4-Diazabicyclo[3.2.2]nonan-4-yl)-2-(2-fluorophenyl)-3-((1-(hydroxymethyl)cyclobutyl)methyl)quinazolin-4(3H)-one (from Intermediate 8E)

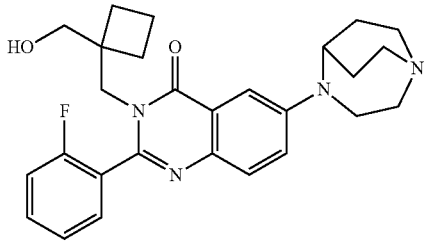 [SMILES: O=c1c2cc(N3CCN4CCC3CC4)ccc2nc(-c2ccccc2F)n1CC1(CO)CCC1]

MS (ESI) m/z 463.2 [M+H]+

Example 2AAT 6-(1,4-Diazabicyclo[3.2.2]nonan-4-yl)-2-cyclopropyl-3-((1-(hydroxymethyl)cyclobutyl)methyl)quinazolin-4(3H)-one (from Intermediate 8E)

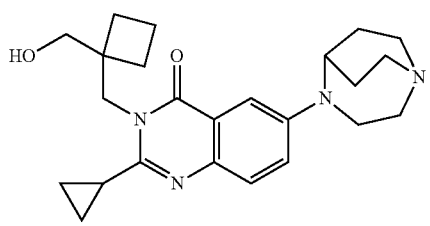 [SMILES: O=c1c2cc(N3CCN4CCC3CC4)ccc2nc(C2CC2)n1CC1(CO)CCC1]

MS (ESI) m/z 409.2 [M+H]+

Example 2AAU 6-(1,4-Diazabicyclo[3.2.2]nonan-4-yl)-2-phenyl-3-((1-(hydroxymethyl)cyclobutyl)methyl)quinazolin-4(3H)-one (from Intermediate 8E)

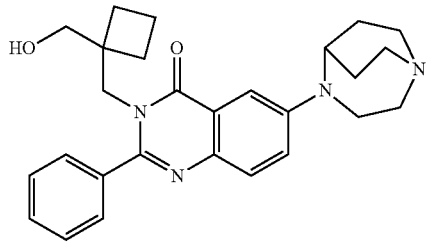 [SMILES: O=c1c2cc(N3CCN4CCC3CC4)ccc2nc(-c2ccccc2)n1CC1(CO)CCC1]

MS (ESI) m/z 445.2 [M+H]+

Example 2AAV 6-(1,4-Diazabicyclo[3.2.2]nonan-4-yl)-3-((1-(hydroxymethyl)cyclobutyl)methyl)-2-m-tolylquinazolin-4(3H)-one (from Intermediate 8E)

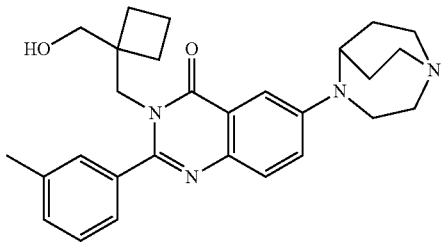 [SMILES: Cc1cccc(-c2nc3ccc(N4CCN5CCC4CC5)cc3c(=O)n2CC2(CO)CCC2)c1]

MS (ESI) m/z 459.2 [M+H]+

Example 2AAW 6-(1,4-Diazabicyclo[3.2.2]nonan-4-yl)-2-(3-fluorophenyl)-3-((1-(hydroxymethyl)cyclobutyl)methyl)quinazolin-4(3H)-one (from Intermediate 8E)

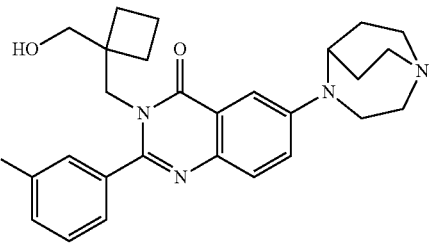

MS (ESI) m/z 463.2 [M+H]+

Example 2AAX 3-(6-(1,4-Diazabicyclo[3.2.2]nonan-4-yl)-3-((1-(hydroxymethyl)cyclobutyl)methyl)-4-oxo-3,4-dihydroquinazolin-2-yl)benzonitrile (from Intermediate 8E)

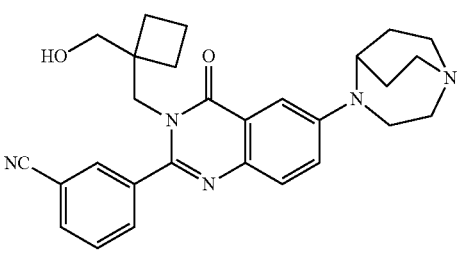 [SMILES: N#Cc1cccc(-c2nc3ccc(N4CCN5CCC4CC5)cc3c(=O)n2CC2(CO)CCC2)c1]

MS (ESI) m/z 470.2 [M+H]+

Example 2AAY 2-(6-((1S,4S)-2,5-Diazabicyclo[2.2.1]heptan-2-yl)-4-oxo-2-phenylquinazolin-3(4H)-yl)-N-isopropylacetamide (from Intermediate 7E)

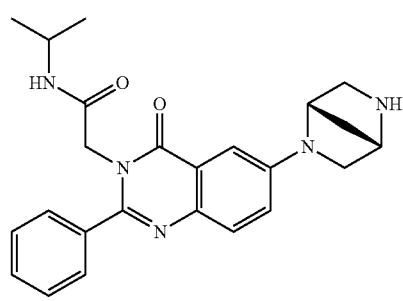 [SMILES: CC(C)NC(=O)Cn1c(-c2ccccc2)nc2ccc(N3C[C@@H]4C[C@H]3CN4)cc2c1=O]

MS (ESI) m/z 418.2 [M+H]+

Example 2AAZ 2-(2-Fluorophenyl)-3-methyl-6-(quinuclidin-3-ylamino)quinazolin-4(3H)-one
(from Intermediate 8C)

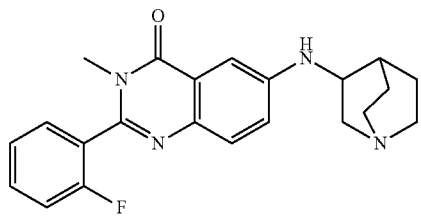 [SMILES: Cn1c(-c2ccccc2F)nc2ccc(NC3CN4CCC3CC4)cc2c1=O]

MS (ESI) m/z 379.2 [M+H]+

Example 2AAAA 6-(1,4-Diazabicyclo[3.2.2]nonan-4-yl)-3-methyl-2-(6-methylpyridin-2-yl)quinazolin-4(3H)-one (from Intermediate 7F)

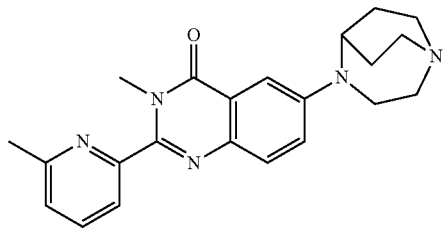 [SMILES: Cc1cccc(-c2nc3ccc(N4CCN5CCC4CC5)cc3c(=O)n2C)n1]

MS (ESI) m/z 376.2 [M+H]+

Example 2AAAB 6-(1,4-Diazabicyclo[3.2.2]nonan-4-yl)-2-(4-fluorophenyl)-3-(3-hydroxy-2,2-dimethylpropyl)quinazolin-4(3H)-one (from Intermediate 8F)

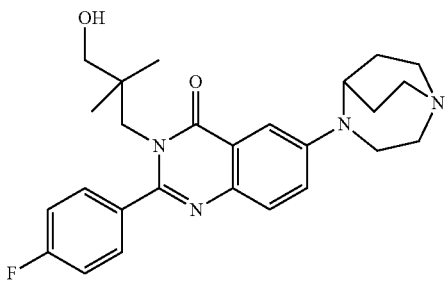 [SMILES: CC(C)(CO)Cn1c(-c2ccc(F)cc2)nc2ccc(N3CCN4CCC3CC4)cc2c1=O]

MS (ESI) m/z 451.2 [M+H]+

Example 2AAAC 6-(1,4-Diazabicyclo[3.2.2]nonan-4-yl)-2-cyclopropyl-3-(3-hydroxy-2,2-dimethylpropyl)quinazolin-4(3H)-one (from Intermediate 8F)

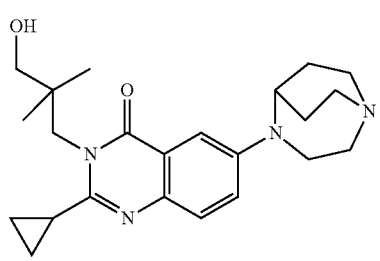 [SMILES: CC(C)(CO)Cn1c(C2CC2)nc2ccc(N3CCN4CCC3CC4)cc2c1=O]

MS (ESI) m/z 397.2 [M+H]+

Example 2AAAD 6-(1,4-Diazabicyclo[3.2.2]nonan-4-yl)-3-(2-methoxyethyl)-2-(6-methylpyridin-2-yl)quinazolin-4(3H)-one (from Intermediate 8G)

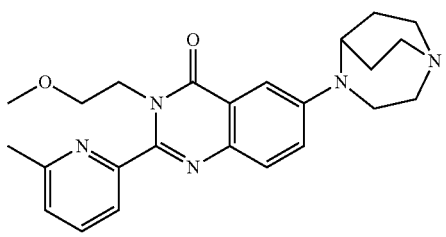 [SMILES: COCCn1c(-c2cccc(C)n2)nc2ccc(N3CCN4CCC3CC4)cc2c1=O]

MS (ESI) m/z 420.2 [M+H]+

Example 2AAAE 6-(1,4-Diazabicyclo[3.2.2]nonan-4-yl)-2-cyclopropyl-3-(2-methoxyethyl)quinazolin-4(3H)-one (from Intermediate 8G)

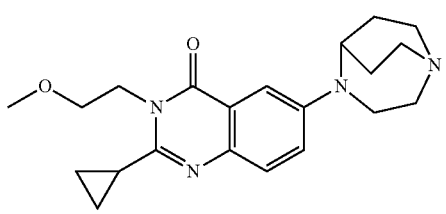 [SMILES: COCCn1c(C2CC2)nc2ccc(N3CCN4CCC3CC4)cc2c1=O]

MS (ESI) m/z 369.2 [M+H]+

Example 2AAAF 6-(1,4-Diazabicyclo[3.2.2]nonan-4-yl)-2-(2-fluorophenyl)-3-(2-methoxyethyl)quinazolin-4(3H)-one (from Intermediate 8G)

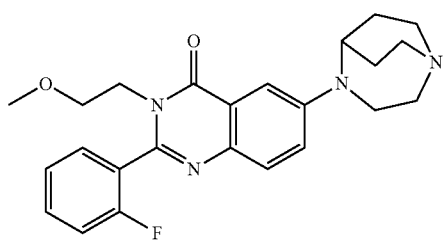 [SMILES: COCCn1c(-c2ccccc2F)nc2ccc(N3CCN4CCC3CC4)cc2c1=O]

MS (ESI) m/z 423.2 [M+H]+

Example 2AAAG 6-(1,4-Diazabicyclo[3.2.2]nonan-4-yl)-3-(2-methoxyethyl)-2-(3-cyanophenyl)quinazolin-4(3H)-one (from Intermediate 8G)

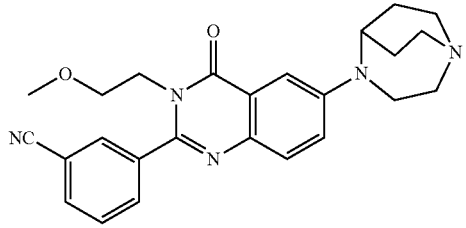 [SMILES: COCCn1c(-c2cccc(C#N)c2)nc2ccc(N3CCN4CCC3CC4)cc2c1=O]

MS (ESI) m/z 430.2 [M+H]+

Example 2AAAH 6-(1,4-Diazabicyclo[3.2.2]nonan-4-yl)-3-(2-methoxyethyl)-2-m-tolylquinazolin-4(3H)-one (from Intermediate 8G)

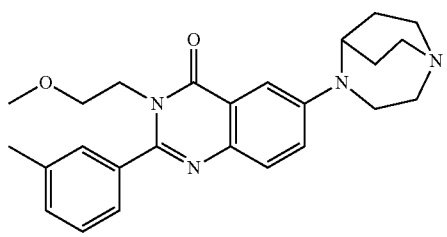 [SMILES: COCCn1c(-c2cccc(C)c2)nc2ccc(N3CCN4CCC3CC4)cc2c1=O]

MS (ESI) m/z 419.2 [M+H]+

Example 2AAAI

2-Cyclopropyl-3-methyl-6-((1S,4S)-5-methyl-2,5-diazabicyclo[2.2.1]heptan-2-yl)quinazolin-4(3H)-one (from Intermediate 8B)

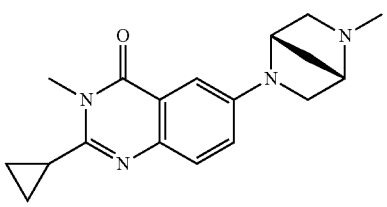 [SMILES: CN1C[C@@H]2C[C@H]1CN2c1ccc2nc(C3CC3)n(C)c(=O)c2c1]

MS (ESI) m/z 311.2 [M+H]+

Example 2AAAJ 2-(3-Fluorophenyl)-3-methyl-6-((1S,4S)-5-methyl-2,5-diazabicyclo[2.2.1]heptan-2-yl)quinazolin-4(3H)-one (from Intermediate 8B)

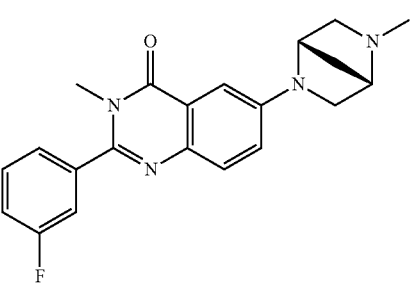 [SMILES: CN1C[C@@H]2C[C@H]1CN2c1ccc2nc(-c3cccc(F)c3)n(C)c(=O)c2c1]

MS (ESI) m/z 365.2 [M+H]+

Example 2AAAK 2-(3-Chlorophenyl)-3-methyl-6-((1S,4S)-5-methyl-2,5-diazabicyclo[2.2.1]heptan-2-yl)quinazolin-4(3H)-one (from Intermediate 8B)

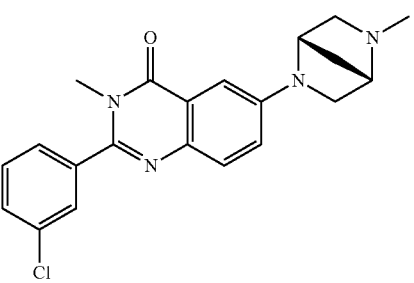 [SMILES: CN1C[C@@H]2C[C@H]1CN2c1ccc2nc(-c3cccc(Cl)c3)n(C)c(=O)c2c1]

MS (ESI) m/z 381.2 [M+H]+

Example 2AAAL 2-(3-Cyanophenyl)-3-methyl-6-((1S,4S)-5-methyl-2,5-diazabicyclo[2.2.1]heptan-2-yl)quinazolin-4(3H)-one (from Intermediate 8B)

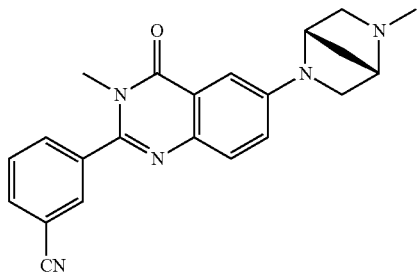 [SMILES: CN1C[C@@H]2C[C@H]1CN2c1ccc2nc(-c3cccc(C#N)c3)n(C)c(=O)c2c1]

MS (ESI) m/z 372.2 [M+H]+

Example 2AAAM 2-(4-Fluorophenyl)-3-methyl-6-((1S,4S)-5-methyl-2,5-diazabicyclo[2.2.1]heptan-2-yl)quinazolin-4(3H)-one (from Intermediate 8B)

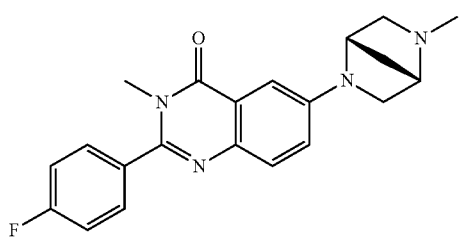 [SMILES: CN1C[C@@H]2C[C@H]1CN2c1ccc2nc(-c3ccc(F)cc3)n(C)c(=O)c2c1]

MS (ESI) m/z 365.2 [M+H]+

Example 2AAAN 2-(3-Chloro-2-fluorophenyl)-3-methyl-6-((1S,4S)-5-methyl-2,5-diazabicyclo[2.2.1]heptan-2-yl)quinazolin-4(3H)-one (from Intermediate 8B)

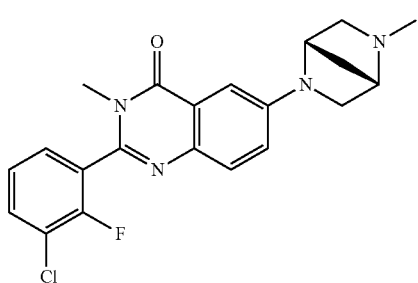 [SMILES: CN1C[C@@H]2C[C@H]1CN2c1ccc2nc(-c3cccc(Cl)c3F)n(C)c(=O)c2c1]

MS (ESI) m/z 399.0 [M+H]+

Example 2AAAO 2-(2,3-Difluorophenyl)-3-methyl-6-((1S,4S)-5-methyl-2,5-diazabicyclo[2.2.1]heptan-2-yl)quinazolin-4(3H)-one (from Intermediate 8B)

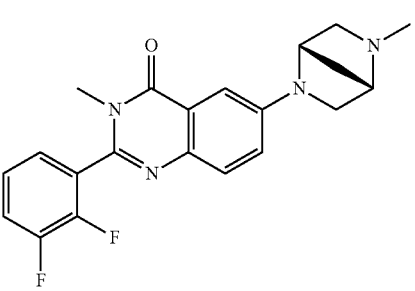 [SMILES: CN1C[C@@H]2C[C@H]1CN2c1ccc2nc(-c3cccc(F)c3F)n(C)c(=O)c2c1]

MS (ESI) m/z 383.0 [M+H]+

Example 2AAAP 2-(5-Chloro-2-fluorophenyl)-3-methyl-6-((1S,4S)-5-methyl-2,5-diazabicyclo[2.2.1]heptan-2-yl)quinazolin-4(3H)-one (from Intermediate 8B)

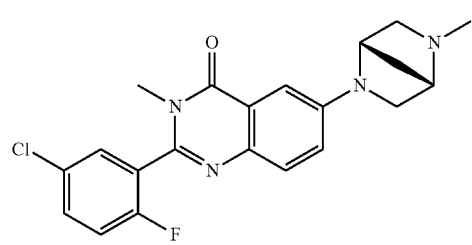 [SMILES: CN1C[C@@H]2C[C@H]1CN2c1ccc2nc(-c3cc(Cl)ccc3F)n(C)c(=O)c2c1]

MS (ESI) m/z 399.0 [M+H]+

Example 2AAAQ 2-(2,5-Difluorophenyl)-3-methyl-6-((1S,4S)-5-methyl-2,5-diazabicyclo[2.2.1]heptan-2-yl)quinazolin-4(3H)-one (from Intermediate 8B)

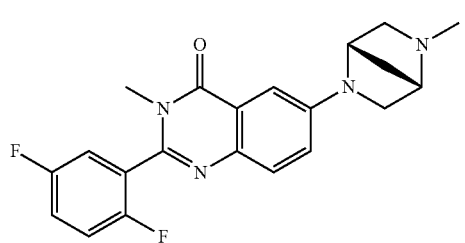 [SMILES: CN1C[C@@H]2C[C@H]1CN2c1ccc2nc(-c3cc(F)ccc3F)n(C)c(=O)c2c1]

MS (ESI) m/z 383.0 [M+H]+

Example 2AAAR

3-Methyl-6-((1S,4S)-5-methyl-2,5-diazabicyclo[2.2.1]heptan-2-yl)-2-m-tolylquinazolin-4(3H)-one (from Intermediate 8B)

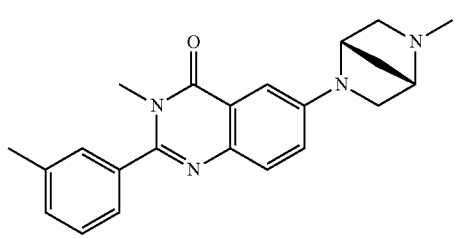

MS (ESI) m/z 361.2 [M+H]+

Example 2AAAS 6-(1,4-Diazabicyclo[3.2.2]nonan-4-yl)-3-((1-(hydroxymethyl)cyclobutyl)methyl)-2-(6-methylpyridin-2-yl)quinazolin-4(3H)-one (from Intermediate 8E)

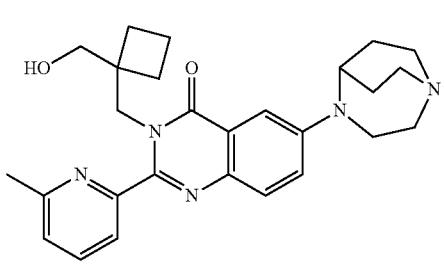 [SMILES: Cc1cccc(-c2nc3ccc(N4CCN5CCC4CC5)cc3c(=O)n2CC2(CO)CCC2)n1]

MS (ESI) m/z 460.2 [M+H]+

Example 2AAAT 6-(1,4-Diazabicyclo[3.2.2]nonan-4-yl)-3-cyclopropyl-2-(2-fluorophenyl)quinazolin-4(3H)-one (from Intermediate 7L)

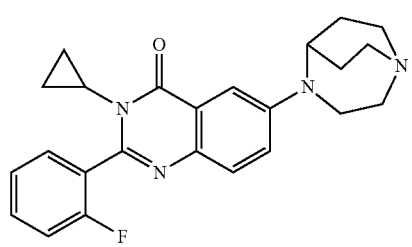 [SMILES: O=c1c2cc(N3CCN4CCC3CC4)ccc2nc(-c2ccccc2F)n1C1CC1]

MS (ESI) m/z 405.2 [M+H]+

Example 2AAAU 6-(1,4-Diazabicyclo[3.2.2]nonan-4-yl)-3-cyclobutyl-2-(2-fluorophenyl)quinazolin-4(3H)-one (from Intermediate 7M)

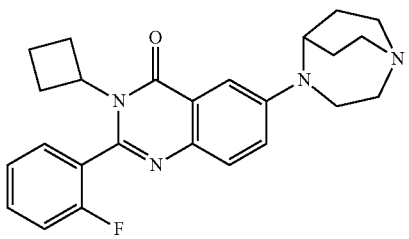 [SMILES: O=c1c2cc(N3CCN4CCC3CC4)ccc2nc(-c2ccccc2F)n1C1CCC1]

MS (ESI) m/z 419.2 [M+H]+

Example 2AAAV 6-(1,4-Diazabicyclo[3.2.2]nonan-4-yl)-3-cyclobutyl-2-(3-chlorophenyl)quinazolin-4(3H)-one (from Intermediate 7M)

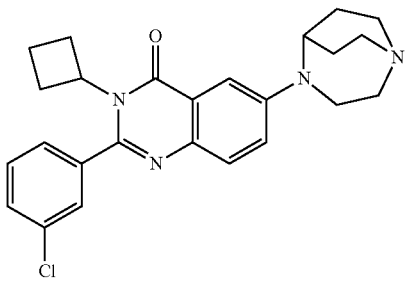 [SMILES: O=c1c2cc(N3CCN4CCC3CC4)ccc2nc(-c2cccc(Cl)c2)n1C1CCC1]

MS (ESI) m/z 435.2 [M+H]+

Example 2AAAW 6-(1,4-Diazabicyclo[3.2.2]nonan-4-yl)-3-cyclobutyl-2-phenylquinazolin-4(3H)-one (from Intermediate 7M)

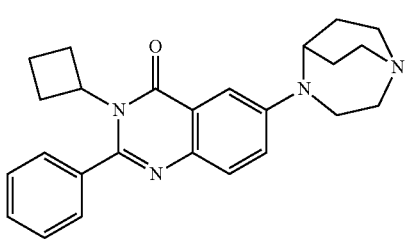 [SMILES: O=c1c2cc(N3CCN4CCC3CC4)ccc2nc(-c2ccccc2)n1C1CCC1]

MS (ESI) m/z 401.2 [M+H]+

Example 2AAAX 6-(1,4-Diazabicyclo[3.2.2]nonan-4-yl)-3-cyclobutyl-2-(3-methylphenyl)quinazolin-4(3H)-one (from Intermediate 7M)

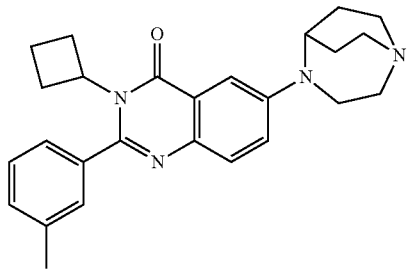 [SMILES: Cc1cccc(-c2nc3ccc(N4CCN5CCC4CC5)cc3c(=O)n2C2CCC2)c1]

MS (ESI) m/z 415.2 [M+H]+

Example 2AAAY 6-(1,4-Diazabicyclo[3.2.2]nonan-4-yl)-3-cyclobutyl-2-(3-cyanophenyl)quinazolin-4(3H)-one (from Intermediate 7M)

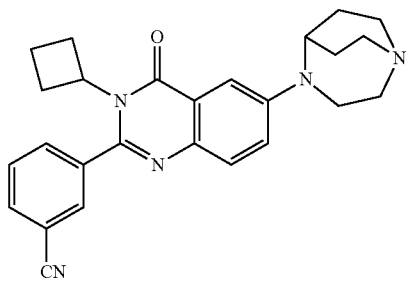 [SMILES: N#Cc1cccc(-c2nc3ccc(N4CCN5CCC4CC5)cc3c(=O)n2C2CCC2)c1]

MS (ESI) m/z 426.2 [M+H]+

Example 2AAAZ 6-(1,4-Diazabicyclo[3.2.2]nonan-4-yl)-3-cyclobutyl-2-(6-methylpyridin-2-yl)quinazolin-4(3H)-one (from Intermediate 7M)

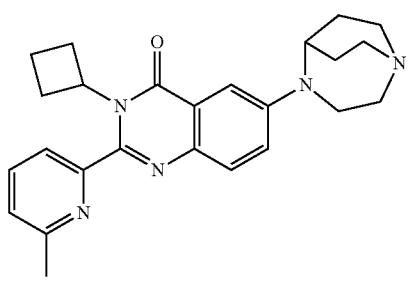 [SMILES: Cc1cccc(-c2nc3ccc(N4CCN5CCC4CC5)cc3c(=O)n2C2CCC2)n1]

MS (ESI) m/z 416.2 [M+H]+

Example 2AAAAA 6-(1,4-Diazabicyclo[3.2.2]nonan-4-yl)-3-cyclobutyl-2-(1-methyl-1H-pyrazol-4-yl)quinazolin-4(3H)-one (from Intermediate 7M)

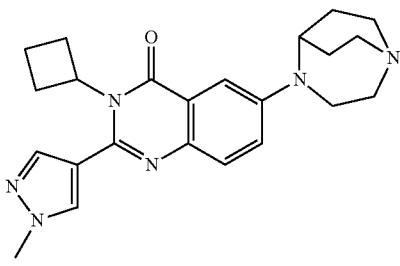 [SMILES: Cn1cc(-c2nc3ccc(N4CCN5CCC4CC5)cc3c(=O)n2C2CCC2)cn1]

MS (ESI) m/z 405.2 [M+H]+

Example 2 AAAAB 6-(1,4-Diazabicyclo[3.2.2]nonan-4-yl)-3-cyclobutyl-2-(6-methylpyridin-2-yl)quinazolin-4(3H)-one (from Intermediate 7M)

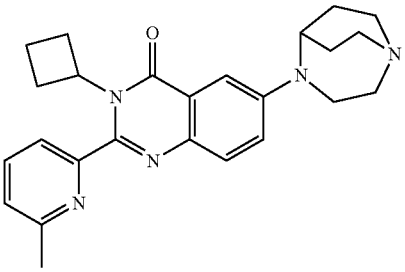 [SMILES: Cc1cccc(-c2nc3ccc(N4CCN5CCC4CC5)cc3c(=O)n2C2CCC2)n1]

MS (ESI) m/z 416.2 [M+H]+

Example 2AAAAC 3-(6-(1,4-Diazabicyclo[3.2.2]nonan-4-yl)-3-cyclobutyl-4-oxo-3,4-dihydroquinazolin-2-yl)benzonitrile (from Intermediate 7M)

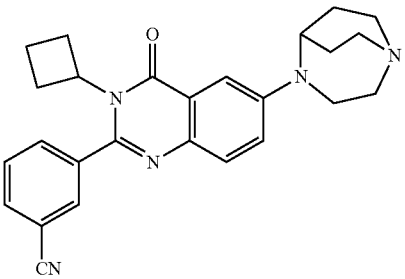 [SMILES: N#Cc1cccc(-c2nc3ccc(N4CCN5CCC4CC5)cc3c(=O)n2C2CCC2)c1]

MS (ESI) m/z 426.2 [M+H]+

Example 2AAAAD 7-(1,4-Diazabicyclo[3.2.2]nonan-4-yl)-2-(3-chlorophenyl)-3-methylquinazolin-4(3H)-one (from Intermediate 8H)

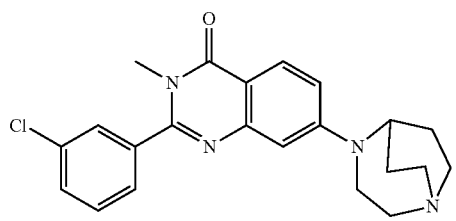 [SMILES: Cn1c(-c2cccc(Cl)c2)nc2cc(N3CCN4CCC3CC4)ccc2c1=O]

MS (ESI) m/z 395.2 [M+H]+

Example 2AAAAE 7-(1,4-Diazabicyclo[3.2.2]nonan-4-yl)-2-(3-fluorophenyl)-3-methylquinazolin-4(3H)-one (from Intermediate 8H)

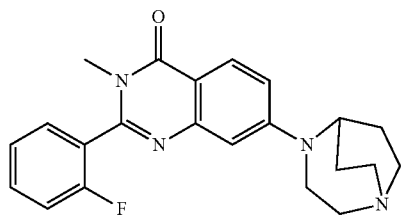 [SMILES: Cn1c(-c2ccccc2F)nc2cc(N3CCN4CCC3CC4)ccc2c1=O]

MS (ESI) m/z 379.2 [M+H]+

Example 2AAAAF 6-(1,4-Diazabicyclo[3.2.2]nonan-4-yl)-2-(2-fluorophenyl)-3-(2-hydroxyethyl)quinazolin-4(3H)-one (from Intermediate 7P)

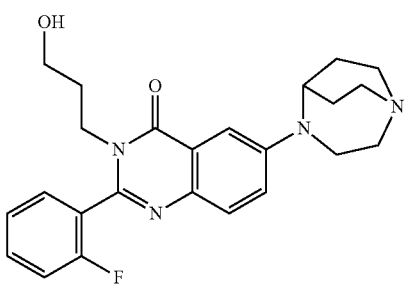 [SMILES: O=c1c2cc(N3CCN4CCC3CC4)ccc2nc(-c2ccccc2F)n1CCCO]

MS (ESI) m/z 409.2 [M+H]+

Example 2AAAAG 6-(1,4-Diazabicyclo[3.2.2]nonan-4-yl)-2-cyclopropyl-3-(2-hydroxyethyl)quinazolin-4(3H)-one (from Intermediate 7P)

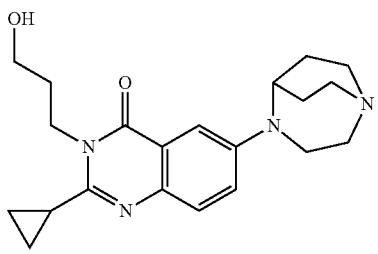 [SMILES: O=c1c2cc(N3CCN4CCC3CC4)ccc2nc(C2CC2)n1CCCO]

MS (ESI) m/z 355.2 [M+H]+

Example 2AAAAH 6-(1,4-Diazabicyclo[3.2.2]nonan-4-yl)-3-methyl-2-(thiazol-5-yl) quinazolin-4(3H)-one (from Intermediate 7F)

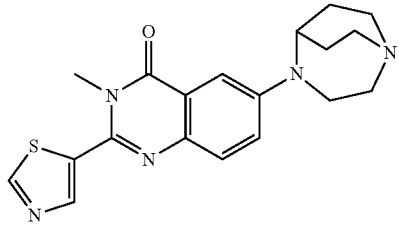 [SMILES: Cn1c(-c2cncs2)nc2ccc(N3CCN4CCC3CC4)cc2c1=O]

MS (ESI) m/z 368.2 [M+H]+

Example 2AAAAI 6-(1,4-Diazabicyclo[3.2.2]nonan-4-yl)-3-methyl-2-(2-methylthiazol-5-yl)quinazolin-4(3H)-one (from Intermediate 7F)

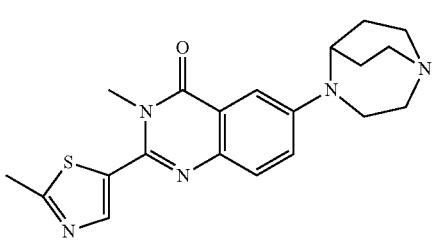 [SMILES: Cc1ncc(-c2nc3ccc(N4CCN5CCC4CC5)cc3c(=O)n2C)s1]

MS (ESI) m/z 382.2 [M+H]+

Example 2AAAAJ 6-(1,4-Diazabicyclo[3.2.2]nonan-4-yl)-3-methyl-2-(4-methylpyridin-2-yl)quinazolin-4(3H)-one (from Intermediate 7F)

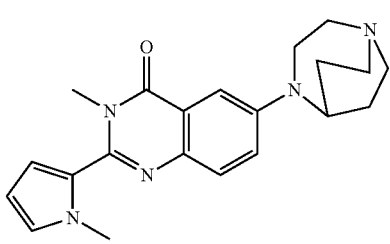 [SMILES: Cn1cccc1-c1nc2ccc(N3CCN4CCC3CC4)cc2c(=O)n1C]

MS (ESI) m/z 364.2 [M+H]+

Example 2AAAAK 6-(1,4-Diazabicyclo[3.2.2]nonan-4-yl)-3-methyl-2-(thiazol-2-yl)quinazolin-4(3H)-one (from Intermediate 7F)

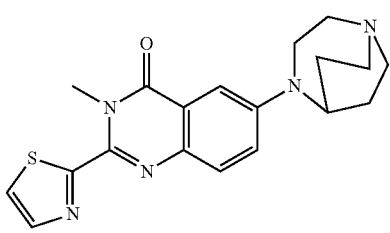 [SMILES: Cn1c(-c2nccs2)nc2ccc(N3CCN4CCC3CC4)cc2c1=O]

MS (ESI) m/z 368.0 [M+H]+

Example 2AAAAL 6-(1,4-Diazabicyclo[3.2.2]nonan-4-yl)-3-methyl-2-(pyridin-4-yl)quinazolin-4(3H)-one (from Intermediate 7F)

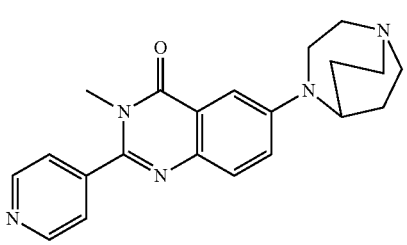 [SMILES: Cn1c(-c2ccncc2)nc2ccc(N3CCN4CCC3CC4)cc2c1=O]

MS (ESI) m/z 362.2 [M+H]+

Example 2AAAAM 6-(1,4-Diazabicyclo[3.2.2]nonan-4-yl)-3-methyl-2-(4-methylpyridin-2-yl)quinazolin-4(3H)-one (from Intermediate 7F)

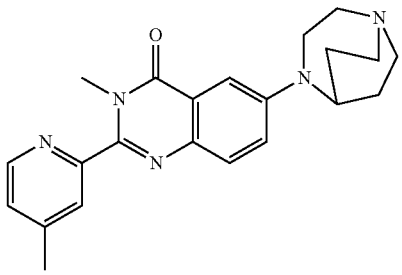 [SMILES: Cc1ccnc(-c2nc3ccc(N4CCN5CCC4CC5)cc3c(=O)n2C)c1]

MS (ESI) m/z 376.2 [M+H]+

Example 2AAAAN 6-(1,4-Diazabicyclo[3.2.2]nonan-4-yl)-3-methyl-2-(5-methylpyridin-3-yl)quinazolin-4(3H)-one (from Intermediate 7F)

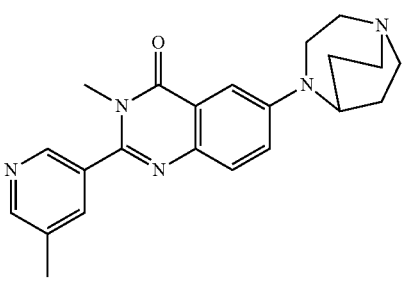 [SMILES: Cc1cncc(-c2nc3ccc(N4CCN5CCC4CC5)cc3c(=O)n2C)c1]

MS (ESI) m/z 376.2 [M+H]+

Example 2AAAAO 2-(Benzo[d]oxazol-2-yl)-6-(1,4-diazabicyclo[3.2.2]nonan-4-yl)-3-methylquinazolin-4(3H)-one (from Intermediate 7F)

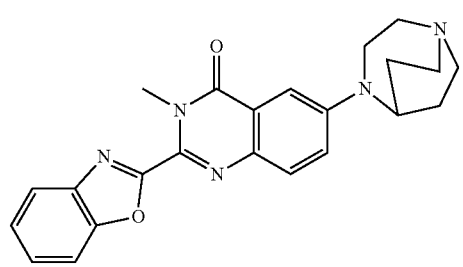 [SMILES: Cn1c(-c2nc3ccccc3o2)nc2ccc(N3CCN4CCC3CC4)cc2c1=O]

MS (ESI) m/z 402.2 [M+H]+

Example 2AAAAP 6-(1,4-Diazabicyclo[3.2.2]nonan-4-yl)-3-methyl-2-(5-methylfuran-2-yl)quinazolin-4(3H)-one (from Intermediate 7F)

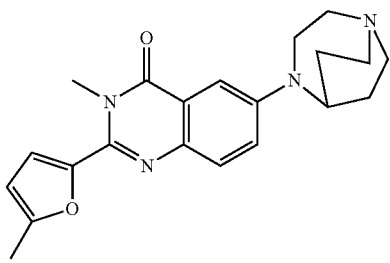 [SMILES: Cc1ccc(-c2nc3ccc(N4CCN5CCC4CC5)cc3c(=O)n2C)o1]

MS (ESI) m/z 365.2 [M+H]+

Example 2AAAAQ 6-(1,4-Diazabicyclo[3.2.2]nonan-4-yl)-2-cyclopropyl-3-(2-hydroxyethyl)quinazolin-4(3H)-one (from Intermediate 8F)

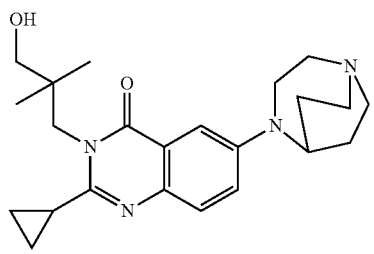 [SMILES: CC(C)(CO)Cn1c(C2CC2)nc2ccc(N3CCN4CCC3CC4)cc2c1=O]

MS (ESI) m/z 397.2 [M+H]+

Example 2AAAAR 6-(1,4-Diazabicyclo[3.2.2]nonan-4-yl)-2-(2-fluorophenyl)-3-(2-hydroxyethyl)quinazolin-4(3H)-one (from Intermediate 8F)

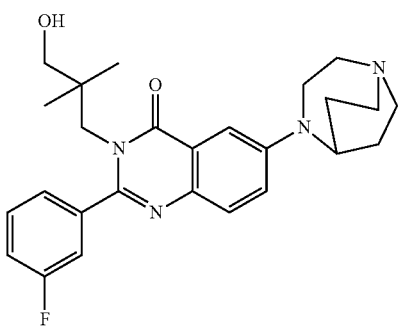 [SMILES: CC(C)(CO)Cn1c(-c2cccc(F)c2)nc2ccc(N3CCN4CCC3CC4)cc2c1=O]

MS (ESI) m/z 451.2 [M+H]+

Example 2AAAAS 6-(1,4-Diazabicyclo[3.2.2]nonan-4-yl)-2-(3-chlorophenyl)-3-(3-hydroxy-2,2-dimethylpropyl)quinazolin-4(3H)-one (from Intermediate 8F)

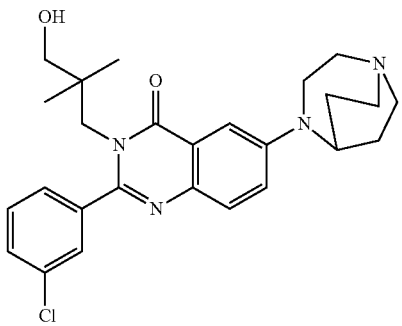 [SMILES: CC(C)(CO)Cn1c(-c2cccc(Cl)c2)nc2ccc(N3CCN4CCC3CC4)cc2c1=O]

MS (ESI) m/z 467.2 [M+H]+

Example 2AAAAT 3-(6-(1,4-Diazabicyclo[3.2.2]nonan-4-yl)-3-(3-hydroxy-2,2-dimethylpropyl)-4-oxo-3,4-dihydroquinazolin-2-yl)benzonitrile (from Intermediate 8F)

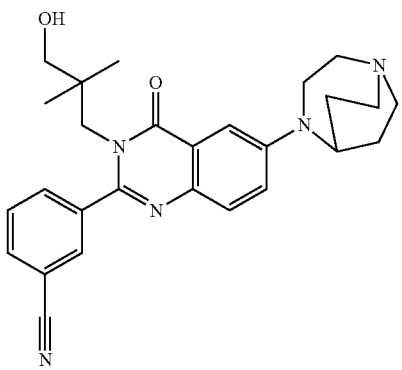 [SMILES: CC(C)(CO)Cn1c(-c2cccc(C#N)c2)nc2ccc(N3CCN4CCC3CC4)cc2c1=O]

MS (ESI) m/z 458.2 [M+H]+

Example 2AAAAU 6-(1,4-Diazabicyclo[3.2.2]nonan-4-yl)-2-(4-fluorophenyl)-3-(3-hydroxy-2,2-dimethylpropyl)quinazolin-4(3H)-one (from Intermediate 8F)

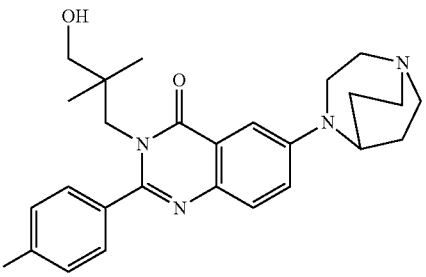

MS (ESI) m/z 451.2 [M+H]+

Example 2AAAAV 6-(1,4-Diazabicyclo[3.2.2]nonan-4-yl)-2-(3-chloro-2-fluorophenyl)-3-(3-hydroxy-2,2-dimethylpropyl)quinazolin-4(3H)-one (from Intermediate 8F)

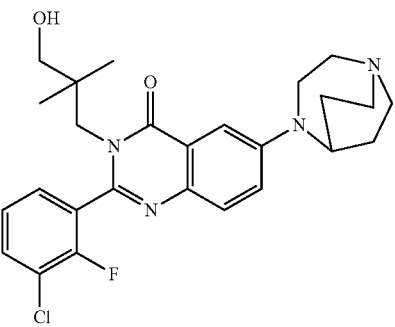

MS (ESI) m/z 485.2 [M+H]+

Example 2AAAAW 6-(1,4-Diazabicyclo[3.2.2]nonan-4-yl)-2-(2,3-difluorophenyl)-3-(3-hydroxy-2,2-dimethylpropyl)quinazolin-4(3H)-one (from Intermediate 8F)

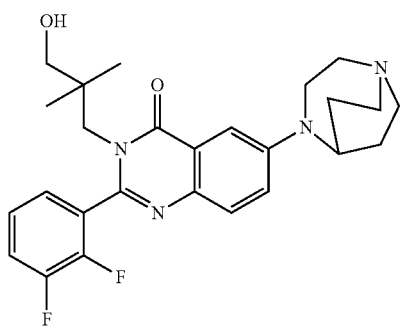 [SMILES: CC(C)(CO)Cn1c(-c2cccc(F)c2F)nc2ccc(N3CCN4CCC3CC4)cc2c1=O]

MS (ESI) m/z 469.2 [M+H]+

Example 2AAAAX 6-(1,4-Diazabicyclo[3.2.2]nonan-4-yl)-2-(5-chloro-2-fluorophenyl)-3-(3-hydroxy-2,2-dimethylpropyl)quinazolin-4(3H)-one (from Intermediate 8F)

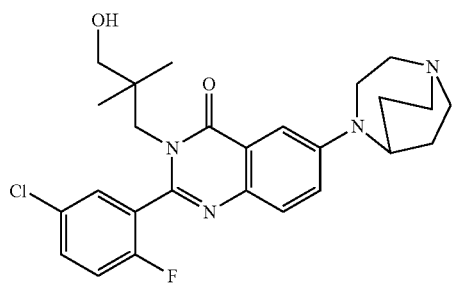 [SMILES: CC(C)(CO)Cn1c(-c2cc(Cl)ccc2F)nc2ccc(N3CCN4CCC3CC4)cc2c1=O]

MS (ESI) m/z 485.2 [M+H]+

Example 2AAAAY 6-(1,4-Diazabicyclo[3.2.2]nonan-4-yl)-2-(2,5-difluorophenyl)-3-(3-hydroxy-2,2-dimethylpropyl)quinazolin-4(3H)-one (from Intermediate 8F)

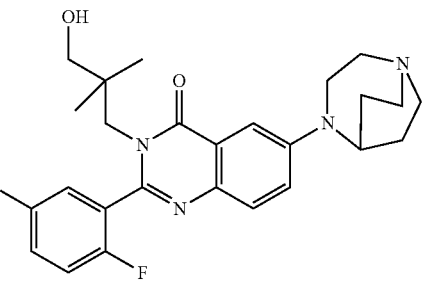

MS (ESI) m/z 469.2 [M+H]+

Example 2AAAAZ 6-(1,4-Diazabicyclo[3.2.2]nonan-4-yl)-3-(3-hydroxy-2,2-dimethylpropyl)-2-m-tolylquinazolin-4(3H)-one (from Intermediate 8F)

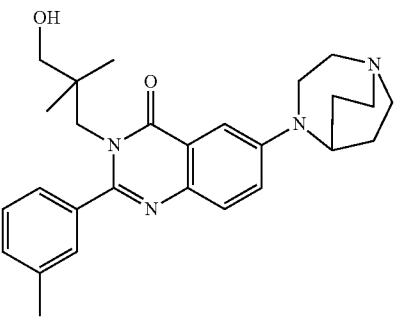 [SMILES: Cc1cccc(-c2nc3ccc(N4CCN5CCC4CC5)cc3c(=O)n2CC(C)(C)CO)c1]

MS (ESI) m/z 447.2 [M+H]+

Example 2AAAAAA 6-(1,4-Diazabicyclo[3.2.2]nonan-4-yl)-2-(2-fluorophenyl)-3-(3-hydroxy-2,2-dimethylpropyl)quinazolin-4(3H)-one (from Intermediate 8F)

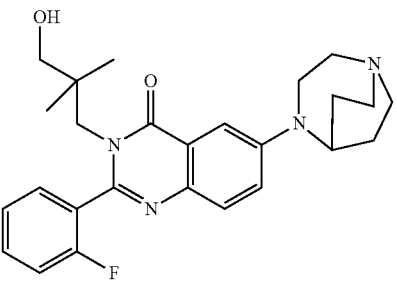 [SMILES: CC(C)(CO)Cn1c(-c2ccccc2F)nc2ccc(N3CCN4CCC3CC4)cc2c1=O]

MS (ESI) m/z 451.2 [M+H]+

Example 2AAAAAB 6-(1,4-Diazabicyclo[3.2.2]nonan-4-yl)-3-cyclopropyl-2-m-tolylquinazolin-4(3H)-one (from Intermediate 7L)

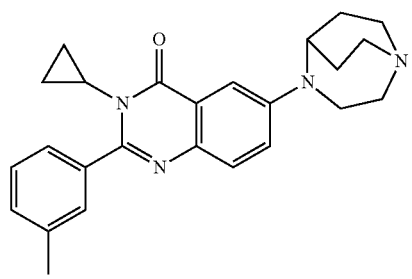 [SMILES: Cc1cccc(-c2nc3ccc(N4CCN5CCC4CC5)cc3c(=O)n2C2CC2)c1]

MS (ESI) m/z 401.2 [M+H]+

Example 2AAAAAC

2-Cyclopropyl-3-methyl-6-((1S,4S)-5-methyl-2,5-diazabicyclo[2.2.1]heptan-2-yl)quinazolin-4(3H)-one (from Intermediate 8B)

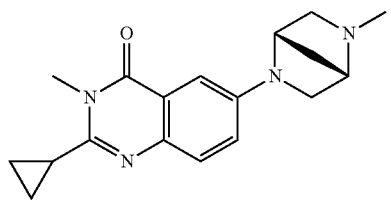 [SMILES: CN1C[C@@H]2C[C@H]1CN2c1ccc2nc(C3CC3)n(C)c(=O)c2c1]

MS (ESI) m/z 311.2 [M+H]+

Example 2AAAAAD 2-(4-Fluorophenyl)-3-methyl-6-((1S,4S)-5-methyl-2,5-diazabicyclo[2.2.1]heptan-2-yl)quinazolin-4(3H)-one (from Intermediate 8B)

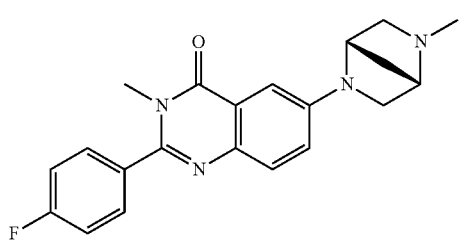 [SMILES: CN1C[C@@H]2C[C@H]1CN2c1ccc2nc(-c3ccc(F)cc3)n(C)c(=O)c2c1]

MS (ESI) m/z 365.2 [M+H]+

Example 2AAAAAE 2-(5-Chloro-2-fluorophenyl)-3-methyl-6-((1S,4S)-5-methyl-2,5-diazabicyclo[2.2.1]heptan-2-yl)quinazolin-4(3H)-one (from Intermediate 8B)

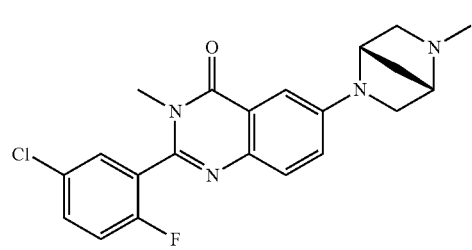 [SMILES: CN1C[C@@H]2C[C@H]1CN2c1ccc2nc(-c3cc(Cl)ccc3F)n(C)c(=O)c2c1]

MS (ESI) m/z 399.0 [M+H]+

Example 2AAAAAF 2-(2,5-Difluorophenyl)-3-methyl-6-((1S,4S)-5-methyl-2,5-diazabicyclo[2.2.1]heptan-2-yl)quinazolin-4(3H)-one (from Intermediate 8B)

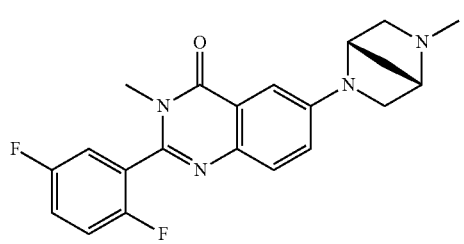 [SMILES: CN1C[C@@H]2C[C@H]1CN2c1ccc2nc(-c3cc(F)ccc3F)n(C)c(=O)c2c1]

MS (ESI) m/z 383.0 [M+H]+

Example 2AAAAAG 3-(7-(1,4-Diazabicyclo[3.2.2]nonan-4-yl)-3-methyl-4-oxo-3,4-dihydroquinazolin-2-yl)benzonitrile (from Intermediate 8H)

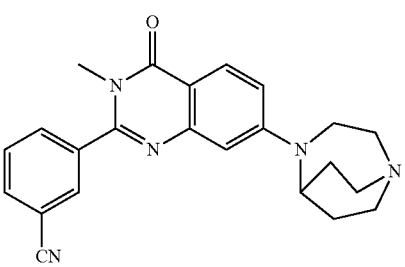 [SMILES: Cn1c(-c2cccc(C#N)c2)nc2cc(N3CCN4CCC3CC4)ccc2c1=O]

MS (ESI) m/z 386.2 [M+H]+

Example 2AAAAAH

4-[3-(3-Chloro-phenyl)-2-methyl-1,1-dioxo-1,2-dihydro-1λ (6)-benzo[1,2,4]thiadiazin-7-yl]-1,4-diaza-bicyclo[3.2.2]nonane (from Intermediate 18A)

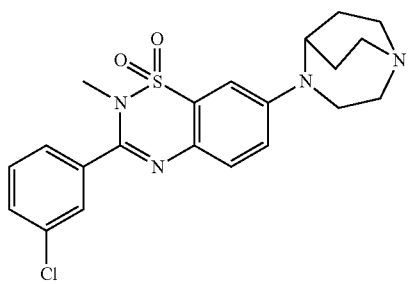 [SMILES: CN1C(c2cccc(Cl)c2)=Nc2ccc(N3CCN4CCC3CC4)cc2S1(=O)=O]

MS (ESI) m/z 431.0 [M+H]+

Example 2AAAAAI

4-[3-(2-Fluoro-phenyl)-2-methyl-1,1-dioxo-1,2-dihydro-1λ (6)-benzo[1,2,4]thiadiazin-7-yl]-1,4-diaza-bicyclo[3.2.2]nonane (from Intermediate 18A)

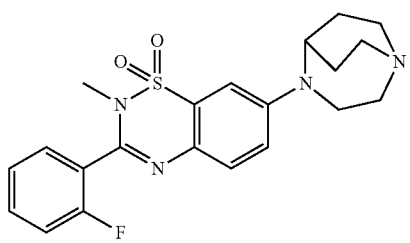 [SMILES: CN1C(c2ccccc2F)=Nc2ccc(N3CCN4CCC3CC4)cc2S1(=O)=O]

MS (ESI) m/z 415.0 [M+H]+

Example 2AAAAAJ

4-[3-(6-Methyl-pyridin-2-yl)-2-methyl-1,1-dioxo-1,2-dihydro-1λ (6)-benzo[1,2,4]thiadiazin-7-yl]-1,4-diaza-bicyclo[3.2.2]nonane (from Intermediate 18A)

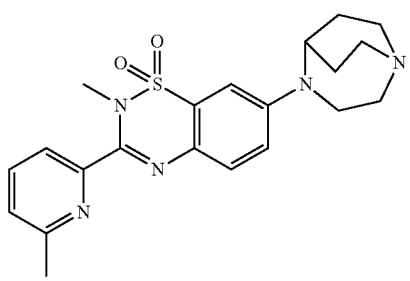 [SMILES: Cc1cccc(C2=Nc3ccc(N4CCN5CCC4CC5)cc3S(=O)(=O)N2C)n1]

MS (ESI) m/z 412.2 [M+H]+

Example 2AAAAAK 4-(2-Methyl-3-thiazol-2-yl-1,1-dioxo-1,2-dihydro-1λ (6)-benzo[1,2,4]thiadiazin-7-yl)-1,4-diaza-bicyclo[3.2.2]nonane (from Intermediate 18A)

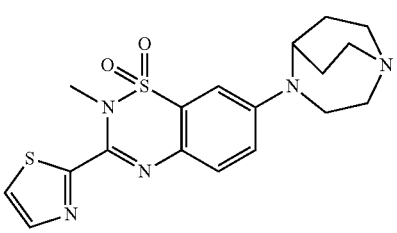 [SMILES: CN1C(c2nccs2)=Nc2ccc(N3CCN4CCC3CC4)cc2S1(=O)=O]

MS (ESI) m/z 404.0 [M+H]+

Example 2AAAAAL

4-[2-Methyl-3-(5-methyl-furan-2-yl)-2-methyl-1,1-dioxo-1,2-dihydro-1λ (6)-benzo[1,2,4]thiadiazin-7-yl]-1,4-diaza-bicyclo[3.2.2]nonane (from Intermediate 18A)

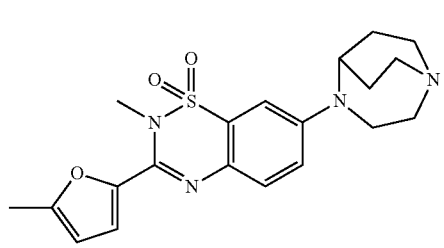 [SMILES: Cc1ccc(C2=Nc3ccc(N4CCN5CCC4CC5)cc3S(=O)(=O)N2C)o1]

MS (ESI) m/z 401.2 [M+H]+

Example 2AAAAAM 4-(3-Cyclopropyl-2-methyl-1,1-dioxo-1,2-dihydro-1λ (6)-benzo[1,2,4]thiadiazin-7-yl)-1,4-diaza-bicyclo[3.2.2]nonane (from Intermediate 18A)

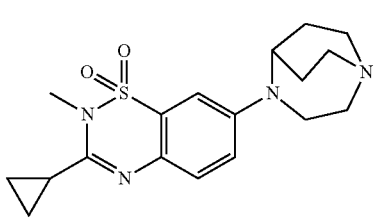 [SMILES: CN1C(C2CC2)=Nc2ccc(N3CCN4CCC3CC4)cc2S1(=O)=O]

MS (ESI) m/z 361.4 [M+H]+

Example 2AAAAAN

4-[3-(2-Fluoro-phenyl)-1,1-dioxo-1,2-dihydro-1λ (6)-benzo[1,2,4]thiadiazin-7-yl]-1,4-diaza-bicyclo[3.2.2]nonane (from Intermediate 18B)

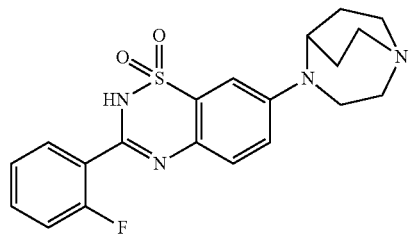 [SMILES: O=S1(=O)NC(c2ccccc2F)=Nc2ccc(N3CCN4CCC3CC4)cc21]

MS (ESI) m/z 401.4 [M+H]+

Example 2AAAAAO

4-[3-(3-Chloro-phenyl)-1,1-dioxo-1,2-dihydro-1λ (6)-benzo[1,2,4]thiadiazin-7-yl]-1,4-diaza-bicyclo[3.2.2]nonane (from Intermediate 18B)

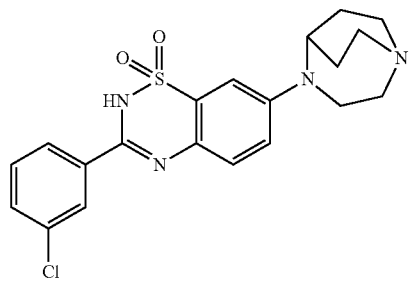 [SMILES: O=S1(=O)NC(c2cccc(Cl)c2)=Nc2ccc(N3CCN4CCC3CC4)cc21]

MS (ESI) m/z 417.4 [M+H]+

Example 2AAAAAP

4-[3-(5-Methyl-furan-2-yl)-1,1-dioxo-1,2-dihydro-1λ (6)-benzo[1,2,4]thiadiazin-7-yl]-1,4-diaza-bicyclo[3.2.2]nonane (from Intermediate 18B)

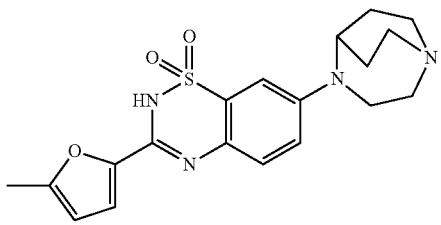 [SMILES: Cc1ccc(C2=Nc3ccc(N4CCN5CCC4CC5)cc3S(=O)(=O)N2)o1]

MS (ESI) m/z 387.5 [M+H]+

Example 2AAAAAQ 4-(1,1-Dioxo-3-thiazol-2-yl-1,2-dihydro-1λ (6)-benzo[1,2,4]thiadiazin-7-yl)-1,4-diaza-bicyclo[3.2.2]nonane (from Intermediate 18B)

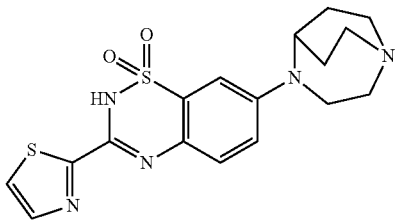 [SMILES: O=S1(=O)NC(c2nccs2)=Nc2ccc(N3CCN4CCC3CC4)cc21]

MS (ESI) m/z 390.4 [M+H]+

Example 2AAAAAR

4-[3-(5-Methyl-thiazol-2-yl)-1,1-dioxo-1,2-dihydro-1λ (6)-benzo[1,2,4]thiadiazin-7-yl]-1,4-diaza-bicyclo[3.2.2]nonane (from Intermediate 18B)

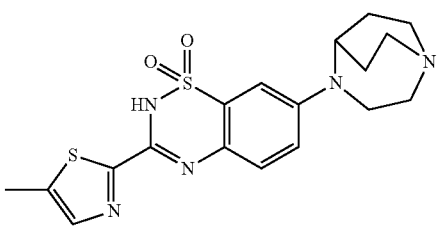 [SMILES: Cc1cnc(C2=Nc3ccc(N4CCN5CCC4CC5)cc3S(=O)(=O)N2)s1]

MS (ESI) m/z 404.5 [M+H]+

Example 2AAAAAS 6-(1,4-Diazabicyclo[3.2.2]nonan-4-yl)-2-(3-chlorophenyl)-3-methylpyrido[3,4-d]pyrimidin-4(3H)-one (from Intermediate 31A)

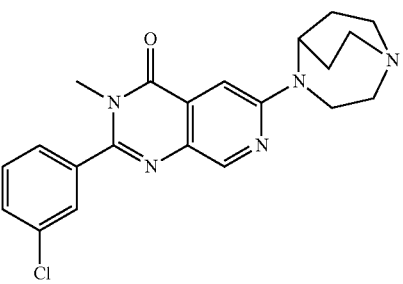 [SMILES: Cn1c(-c2cccc(Cl)c2)nc2cnc(N3CCN4CCC3CC4)cc2c1=O]

MS (ESI) m/z 396.2 [M+H]+

Example 2AAAAAT 6-(1,4-Diazabicyclo[3.2.2]nonan-4-yl)-2-cyclopropyl-3-methylpyrido[3,4-d]pyrimidin-4(3H)-one (from Intermediate 31A)

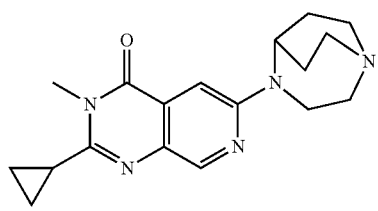 [SMILES: Cn1c(C2CC2)nc2cnc(N3CCN4CCC3CC4)cc2c1=O]

MS (ESI) m/z 326.2 [M+H]+

Example 2AAAAAU 6-(1,4-Diazabicyclo[3.2.2]nonan-4-yl)-2-(3-chlorophenyl)pyrido[3,4-d]pyrimidin-4(3H)-one (from Intermediate 31B)

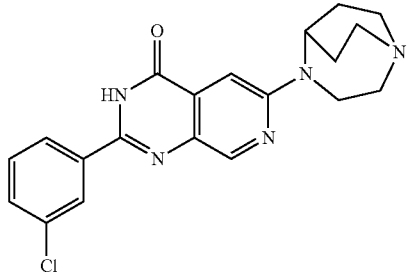 [SMILES: O=c1[nH]c(-c2cccc(Cl)c2)nc2cnc(N3CCN4CCC3CC4)cc12]

MS (ESI) m/z 381.9 [M+H]+

Example 2AAAAAV 6-(1,4-Diazabicyclo[3.2.2]nonan-4-yl)-2-cyclopropylpyrido[3,4-d]pyrimidin-4(3H)-one (from Intermediate 31B)

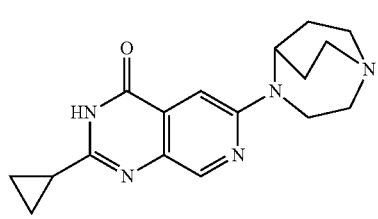 [SMILES: O=c1[nH]c(C2CC2)nc2cnc(N3CCN4CCC3CC4)cc12]

MS (ESI) m/z 312.2 [M+H]+

Example 2AAAAAW 6-(1,4-Diazabicyclo[3.2.2]nonan-4-yl)-2-cyclopropyl-3-(3-hydroxy-2,2-dimethylpropyl)pyrido[3,4-d]pyrimidin-4(3H)-one (from Intermediate 31C)

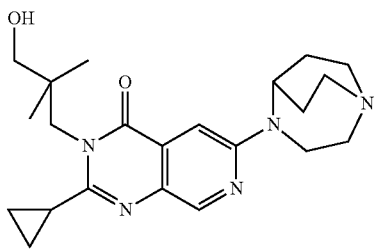 [SMILES: CC(C)(CO)Cn1c(C2CC2)nc2cnc(N3CCN4CCC3CC4)cc2c1=O]

MS (ESI) m/z 398.2 [M+H]+

Example 2AAAAAX 7-(1,4-Diazabicyclo[3.2.2]nonan-4-yl)-2-cyclopropyl-3-dimethylquinazolin-4(3H)-one (from Intermediate 8H)

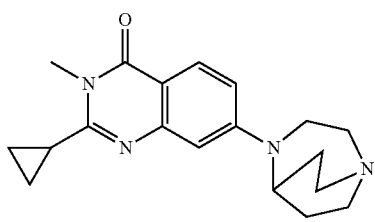 [SMILES: Cn1c(C2CC2)nc2cc(N3CCN4CCC3CC4)ccc2c1=O]

MS (ESI) m/z 325.2 [M+H]+

Example 3A

3-Methyl-6-(5-methylhexahydropyrrolo[3,4-c]pyrrole-2(1H)-yl)quinazolin-4(3H)-one

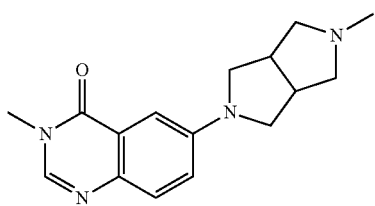

2-Amino-N-methyl-5-(5-methylhexahydropyrrolo[3,4-c]pyrrole-2(1H)-yl)benzamide (Intermediate 8A) (100 mg, 0.36 mmol) was dissolved in triethoxymethane (1 mL) and sealed in a microwave vial. Heated at 160° C. for 10 minutes. Reaction allowed to cool to room temperature and lithium hydroxide solution added (0.5 mL, 1M in methanol) and reaction stirred overnight. Organic layer loaded onto a 1 g SCX cartridge. The crude material was purified by SCX, and the solvent removed under reduced pressure. The crude material was then re-dissolved in methanol (1 mL) and purified by preparative-HPLC. Purified sample was free-based using 500 mg SCX cartridge to afford 3-methyl-6-(5-methylhexahydropyrrolo[3,4-c]pyrrole-2(1H)-yl)quinazolin-4(3H)-one (56 mg, 0.2 mmol).

MS (ESI) m/z 285.2 [M+H]+

Similarly Prepared were

Example 3B

3-Methyl-6-(5-methylhexahydropyrrolo[3,4-c]pyrrol-2(1H)-yl)-2-phenylquinazolin-4(3H)-one (from Intermediate 8A)

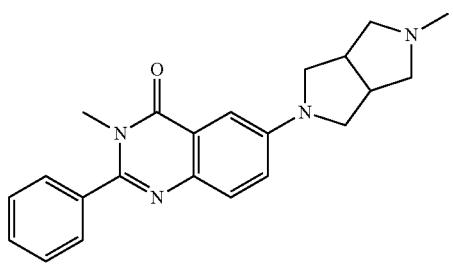 [SMILES: CN1CC2CN(c3ccc4nc(-c5ccccc5)n(C)c(=O)c4c3)CC2C1]

MS (ESI) m/z 361.2 [M+H]+

Example 3C 2,3-Dimethyl-6-(5-methylhexahydropyrrolo[3,4-c]pyrrol-2(1H)-yl)quinazolin-4 (3H)-one (from Intermediate 8A)

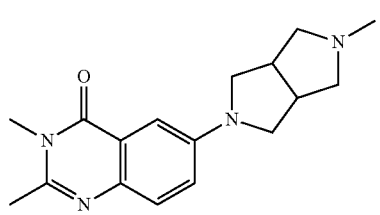

MS (ESI) m/z 299.2 [M+H]+

Example 3D

2-Ethyl-3-methyl-6-(5-methylhexahydropyrrolo[3,4-c]pyrrol-2(1H)-yl)quinazolin-4(3H)-one (from Intermediate 8A)

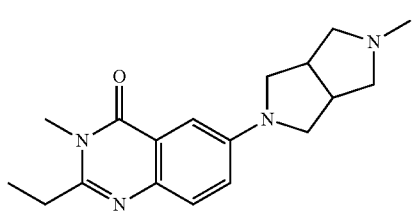 [SMILES: CCc1nc2ccc(N3CC4CN(C)CC4C3)cc2c(=O)n1C]

MS (ESI) m/z 313.2 [M+H]+

Example 3E: 3-Methyl-6-((1S,4S)-5-methyl-2,5-diazabicyclo[2.2.1]heptan-2-yl)quinazolin-4(3H)-one (from Intermediate 8B)

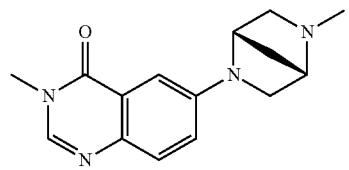

MS (ESI) m/z 271.0 [M+H]+

Example 3F

3-Methyl-6-((1S,4S)-5-methyl-2,5-diazabicyclo[2.2.1]heptan-2-yl)-2-phenylquinazolin-4(3H)-one (from Intermediate 8B)

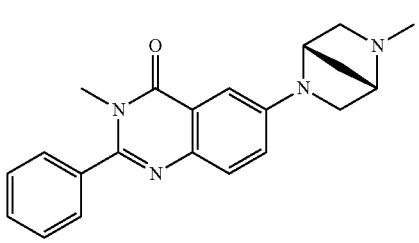 [SMILES: CN1C[C@@H]2C[C@H]1CN2c1ccc2nc(-c3ccccc3)n(C)c(=O)c2c1]

MS (ESI) m/z 347.2 [M+H]+

Example 3G 2,3-Dimethyl-6-((1S,4S)-5-methyl-2,5-diazabicyclo[2.2.1]heptan-2-yl)quinazolin-4(3H)-one (from Intermediate 8B)

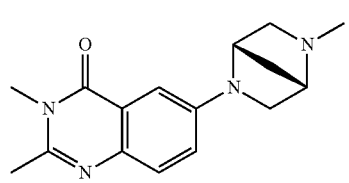

MS (ESI) m/z 285.2 [M+H]+

Example 3H

2-Ethyl-3-methyl-6-((1S,4S)-5-methyl-2,5-diazabicyclo[2.2.1]heptan-2-yl)quinazolin-4(3H)-one (from Intermediate 8B)

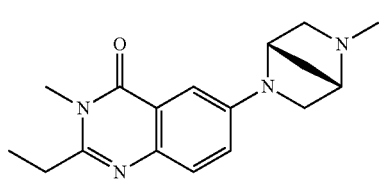 [SMILES: CCc1nc2ccc(N3C[C@@H]4C[C@H]3CN4C)cc2c(=O)n1C]

MS (ESI) m/z 299.2 [M+H]+

Example 3I 6-(1,4-Diazabicyclo[3.2.2]nonan-4-yl)-3-methylquinazolin-4(3H)-one (from Intermediate 7F)

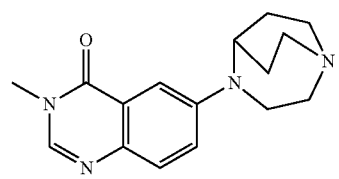 [SMILES: Cn1cnc2ccc(N3CCN4CCC3CC4)cc2c1=O]

MS (ESI) m/z 285.2 [M+H]+

Example 3J tert-Butyl 2-(6-(1,4-diazabicyclo[3.2.2]nonan-4-yl)-2-ethyl-4-oxoquinazolin-3(4H)-yl)acetate (from Intermediate 7B)

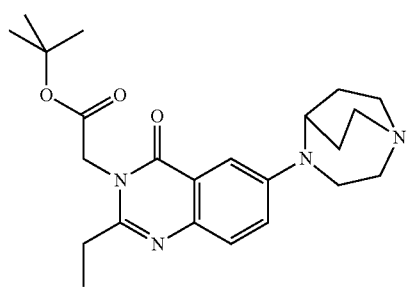 [SMILES: CCc1nc2ccc(N3CCN4CCC3CC4)cc2c(=O)n1CC(=O)OC(C)(C)C]

MS (ESI) m/z 413.2 [M+H]+

Example 3K 6-(1,4-Diazabicyclo[3.2.2]nonan-4-yl)-2-phenylquinazolin-4(3H)-one (from Intermediate 8D)

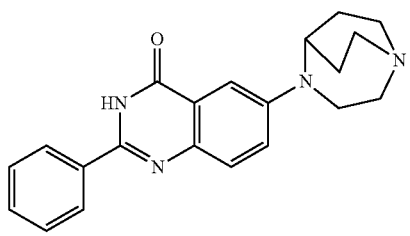 [SMILES: O=c1[nH]c(-c2ccccc2)nc2ccc(N3CCN4CCC3CC4)cc12]

MS (ESI) m/z 347.2 [M+H]+

Example 3L 6-(1,4-Diazabicyclo[3.2.2]nonan-4-yl)-3-methyl-2-phenylquinazolin-4(3H)-one (from Intermediate 7F)

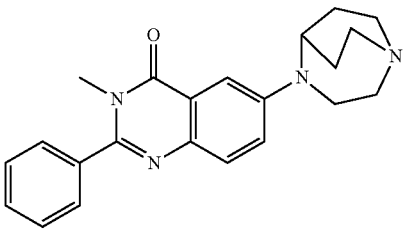 [SMILES: Cn1c(-c2ccccc2)nc2ccc(N3CCN4CCC3CC4)cc2c1=O]

MS (ESI) m/z 361.2 [M+H]+

Example 3M 6-(1,4-Diazabicyclo[3.2.2]nonan-4-yl)-2-methyl-3-methylquinazolin-4(3H)-one (from Intermediate 7F)

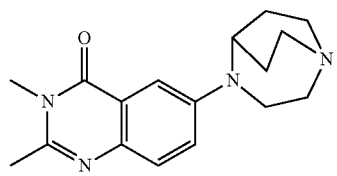 [SMILES: Cc1nc2ccc(N3CCN4CCC3CC4)cc2c(=O)n1C]

MS (ESI) m/z 299.2 [M+H]+

Example 3N 6-(1,4-Diazabicyclo[3.2.2]nonan-4-yl)-3-(3-hydroxy-2,2-dimethylpropyl)quinazolin-4(3H)-one (from Intermediate 8F)

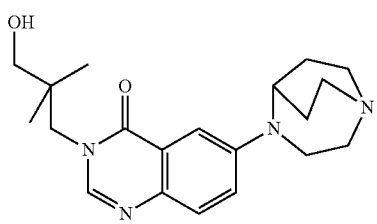 [SMILES: CC(C)(CO)Cn1cnc2ccc(N3CCN4CCC3CC4)cc2c1=O]

MS (ESI) m/z 357.2 [M+H]+

Example 3O 6-(1,4-Diazabicyclo[3.2.2]nonan-4-yl)-2-ethyl-3-(3-hydroxy-2,2-dimethylpropyl)quinazolin-4(3H)-one (from Intermediate 8F)

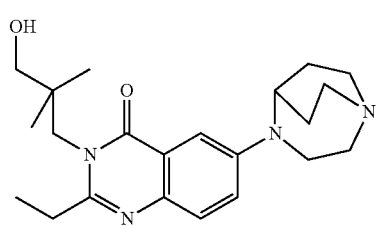 [SMILES: CCc1nc2ccc(N3CCN4CCC3CC4)cc2c(=O)n1CC(C)(C)CO]

MS (ESI) m/z 357.2 [M+H]+

Example 3P 6-(1,4-Diazabicyclo[3.2.2]nonan-4-yl)-3-(2-methoxyethyl)quinazolin-4(3H)-one (from Intermediate 8G)

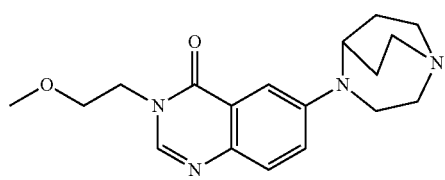 [SMILES: COCCn1cnc2ccc(N3CCN4CCC3CC4)cc2c1=O]

MS (ESI) m/z 329.2 [M+H]+

Example 3Q 6-(1,4-Diazabicyclo[3.2.2]nonan-4-yl)-3-(2-methoxyethyl)-2-methylquinazolin-4(3H)-one (from Intermediate 8G)

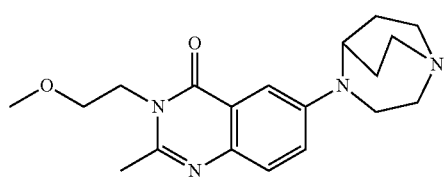 [SMILES: COCCn1c(C)nc2ccc(N3CCN4CCC3CC4)cc2c1=O]

MS (ESI) m/z 343.2 [M+H]+

Example 3R 6-(1,4-Diazabicyclo[3.2.2]nonan-4-yl)-3-cyclobutylquinazolin-4(3H)-one (from Intermediate 7M)

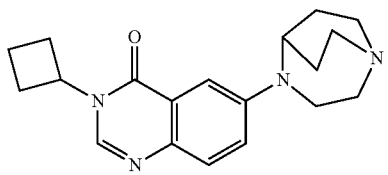 [SMILES: O=c1c2cc(N3CCN4CCC3CC4)ccc2ncn1C1CCC1]

MS (ESI) m/z 325.2 [M+H]+

Example 3S 6-(1,4-Diazabicyclo[3.2.2]nonan-4-yl)-3-cyclobutyl-2-ethylquinazolin-4(3H)-one (from Intermediate 7M)

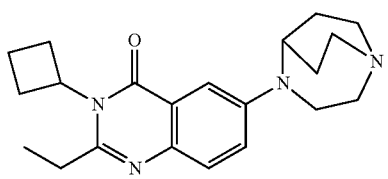 [SMILES: CCc1nc2ccc(N3CCN4CCC3CC4)cc2c(=O)n1C1CCC1]

MS (ESI) m/z 353.2 [M+H]+

Example 3T 7-(1,4-Diazabicyclo[3.2.2]nonan-4-yl)-2,3-dimethylquinazolin-4(3H)-one (from Intermediate 8H)

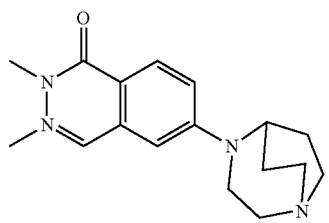

MS (ESI) m/z 299.2 [M+H]+

Example 3U 7-(1,4-Diazabicyclo[3.2.2]nonan-4-yl)-2-ethyl-3-methylquinazolin-4(3H)-one (from Intermediate 8H)

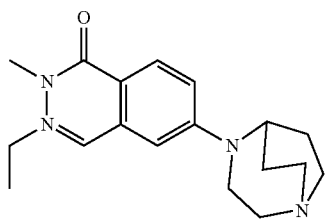

MS (ESI) m/z 313.2 [M+H]+

Example 3V 7-(1,4-Diazabicyclo[3.2.2]nonan-4-yl)-3-methylquinazolin-4(3H)-one (from Intermediate 8H)

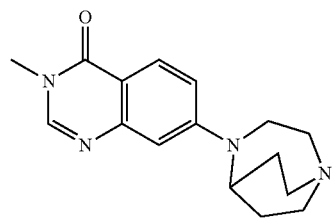 [SMILES: Cn1cnc2cc(N3CCN4CCC3CC4)ccc2c1=O]

MS (ESI) m/z 285.0 [M+H]+

Example 3W 6-(1,4-Diazabicyclo[3.2.2]nonan-4-yl)-3-(3-hydroxy-2,2-dimethylpropyl)quinazolin-4(3H)-one (from Intermediate 8F)

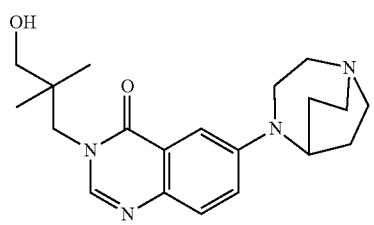 [SMILES: CC(C)(CO)Cn1cnc2ccc(N3CCN4CCC3CC4)cc2c1=O]

MS (ESI) m/z 357.2 [M+H]+

Example 3X 6-(1,4-Diazabicyclo[3.2.2]nonan-4-yl)-2-ethyl-3-(3-hydroxy-2,2-dimethylpropyl)quinazolin-4(3H)-one (from Intermediate 8F)

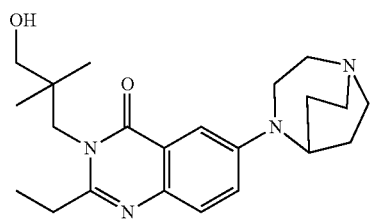 [SMILES: CCc1nc2ccc(N3CCN4CCC3CC4)cc2c(=O)n1CC(C)(C)CO]

MS (ESI) m/z 385.2 [M+H]+

Example 3Y 4-(3-Ethyl-2-methyl-1,1-dioxo-1,2-dihydro-1$\lambda^{6}$-benzo[1,2,4]thiadiazin-7-yl)-1,4-diaza-bicyclo[3.2.2]nonane (from Intermediate 18A)

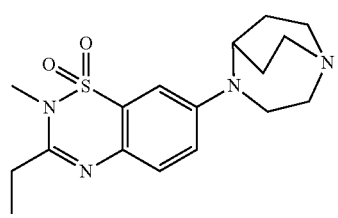 [SMILES: CCC1=Nc2ccc(N3CCN4CCC3CC4)cc2S(=O)(=O)N1C]

MS (ESI) m/z 349.2 [M+H]+

Example 3Z 4-(2,3-Dimethyl-1,1-dioxo-1,2-dihydro-1$\lambda^{6}$-benzo[1,2,4]thiadiazin-7-yl)-1,4-diaza-bicyclo[3.2.2]nonane (from Intermediate 18A)

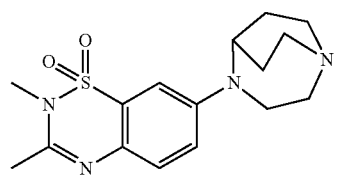 [SMILES: CC1=Nc2ccc(N3CCN4CCC3CC4)cc2S(=O)(=O)N1C]

MS (ESI) m/z 335.4 [M+H]+

Example 3AA 6-(1,4-Diazabicyclo[3.2.2]nonan-4-yl)-3-methylpyrido[3,4-d]pyrimidin-4(3H)-one (from Intermediate 31A)

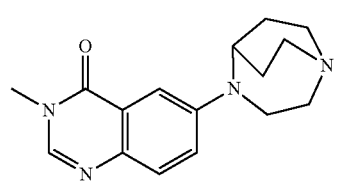 [SMILES: Cn1cnc2ccc(N3CCN4CCC3CC4)cc2c1=O]

MS (ESI) m/z 286.2 [M+H]+

Example 3AB 6-(1,4-Diazabicyclo[3.2.2]nonan-4-yl)-2-ethyl-3-methylpyrido[3,4-d]pyrimidin-4(3H)-one (from Intermediate 31A)

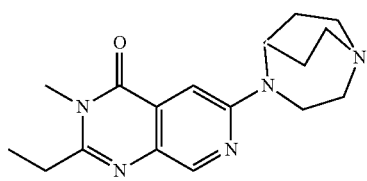

MS (ESI) m/z 314.2 [M+H]+

Example 3AC 6-(1,4-Diazabicyclo[3.2.2]nonan-4-yl)-3-methyl-2-phenylpyrido[3,4-d]pyrimidin-4(3H)-one (from Intermediate 31A)

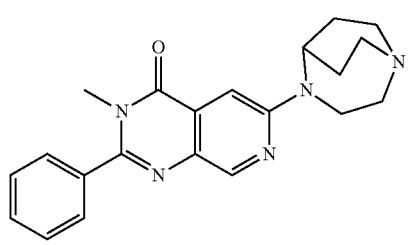 [SMILES: Cn1c(-c2ccccc2)nc2cnc(N3CCN4CCC3CC4)cc2c1=O]

MS (ESI) m/z 362.2 [M+H]+

Example 3AD 6-(1,4-Diazabicyclo[3.2.2]nonan-4-yl)-2-ethylpyrido[3,4-d]pyrimidin-4(3H)-one (from Intermediate 31B)

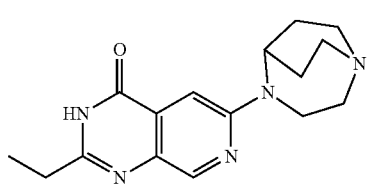 [SMILES: CCc1nc2cnc(N3CCN4CCC3CC4)cc2c(=O)[nH]1]

MS (ESI) m/z 300.2 [M+H]+

Example 3AE 6-(1,4-Diazabicyclo[3.2.2]nonan-4-yl)-2-phenylpyrido[3,4-d]pyrimidin-4(3H)-one (from Intermediate 31B)

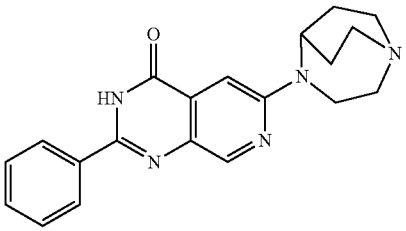

MS (ESI) m/z 348.2 [M+H]+

Example 3AF 6-(1,4-Diazabicyclo[3.2.2]nonan-4-yl)-3-(3-hydroxy-2,2-dimethylpropyl)pyrido[3,4-d]pyrimidin-4(3H)-one (from Intermediate 31C)

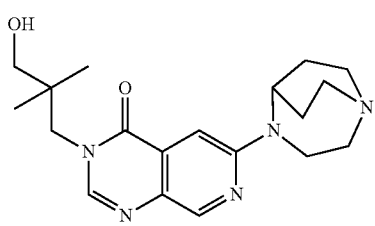 [SMILES: CC(C)(CO)Cn1cnc2cnc(N3CCN4CCC3CC4)cc2c1=O]

MS (ESI) m/z 358.2 [M+H]+

Example 3AG 6-(1,4-Diazabicyclo[3.2.2]nonan-4-yl)-2-ethyl-3-(3-hydroxy-2,2-dimethylpropyl)pyrido[3,4-d]pyrimidin-4(3H)-one (from Intermediate 31C)

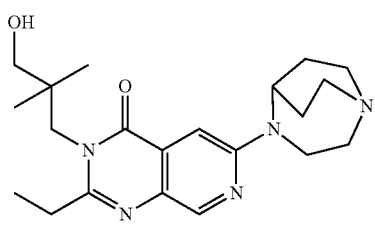 [SMILES: CCc1nc2cnc(N3CCN4CCC3CC4)cc2c(=O)n1CC(C)(C)CO]

MS (ESI) m/z 386.2 [M+H]+

Example 4A 2-(6-(Hexahydropyrrolo[3,4-c]pyrrol-2(1H)-yl)-4-oxo-2-phenylquinazolin-3(4H)-yl-N-isopropylacetamide

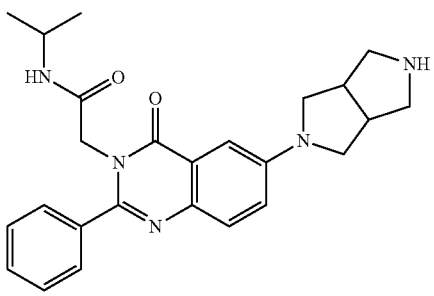 [SMILES: CC(C)NC(=O)Cn1c(-c2ccccc2)nc2ccc(N3CC4CNCC4C3)cc2c1=O]

2,2,2-Trifluoroacetic acid (0.2 g, 1.72 mmol) was added to a solution of tert-butyl 5-(3-(2-(isopropylamino)-2-oxoethyl)-4-oxo-2-phenyl-3,4-dihydroquiazolin-6-yl)hexahydropyrrolo[3,4-c]pyrrole-2(1H)-carboxylate (Intermediate 12A) (129 mg, 0.24 mmol) in dichloromethane (5 mL). The resulting solution was stirred for 2 hours. The resultant crude material was purified using a 1 g SCX cartridge to afford 2-(6-(hexahydropyrrolo[3,4-c]pyrrol-2(1H)-yl)-4-oxo-2-phenylquinazolin-3(4H)-yl-N-isopropylacetamide (65 mg, 0.15 mmol).

MS (ESI) m/z 432.2 [M+H]+

Similarly Prepared were

Example 4B 2-(6-(Hexahydropyrrolo[3,4-c]pyrrol-2(1H)-yl)-4-oxoquinazolin-3(4H)-yl)-N-isopropylacetamide (from Intermediate 12B)

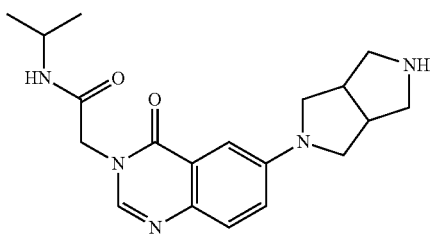 [SMILES: CC(C)NC(=O)Cn1cnc2ccc(N3CC4CNCC4C3)cc2c1=O]

MS (ESI) m/z 396.2 [M+H]+

Example 4C 2-(2-Cyclopropyl-6-(hexahydropyrrolo[3,4-c]pyrrol-2(1H)-yl)-4-oxoquinazolin-3(4H)-yl)-N-isopropylacetamide (from Intermediate 12C)

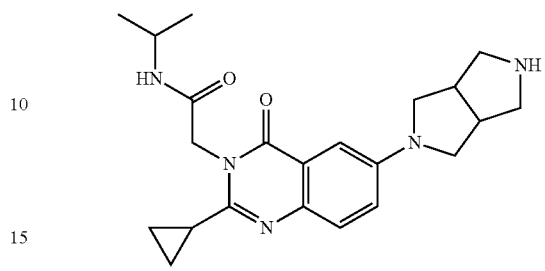

MS (ESI) m/z 396.2 [M+H]+

Example 4D 7-(Hexahydropyrrolo[3,4-c]pyrrol-2(1H)-yl)-2-methylisoquinolin-1(2H)-one (from Intermediate 20B)

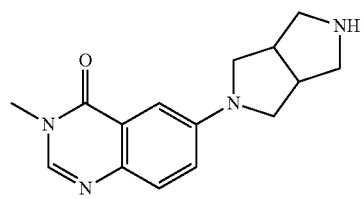 [SMILES: Cn1cnc2ccc(N3CC4CNCC4C3)cc2c1=O]

MS (ESI) m/z 270 [M+H]+

Example 5A

N-Isopropyl-2-(6-(5-methylhexahydropyrrolo[3,4-c]pyrrol-2(1H)-yl)-4-oxo-2-phenylquinazolin-3(4H)-yl)acetamide

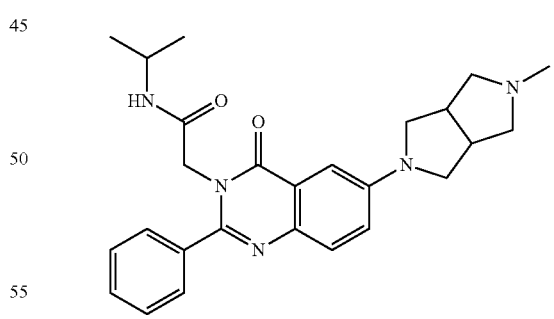

2-(6-(hexahydropyrrolo[3,4-c]pyrrol-2(1H)-yl)-4-oxo-2-phenylquinazolin-3(4H)-yl-N-isopropylacetamide (EXAMPLE 4A) (100 mg, 0.23 mmol) was dissolved in acetonitrile (2 mL) before addition of formaldehyde (28 mg, 0.35 mmol) and MP-cyanoborohydride (140 mg, 0.36 mmol) followed by 2 drops of acetic acid. The resulting solution was sealed in a microwave vial and heated at 130° C. for 20 minutes. Reaction mixture was then diluted with methanol before loading directly onto a 1 g SCX cartridge. The crude material was purified by SCX. The solvent was removed under reduced pressure and then re-dissolved in methanol (1 mL) and purified by preparative-HPLC. Purified sample was free-based using 500 mg SCX cartridge to afford N-isopropyl-2-(6-(5-methylhexahydropyrrolo[3,4-c]pyrrol-2(1H)-yl)-4-oxo-2-phenylquinazolin-3(4H)-yl)acetamide (38 mg, 0.09 mmol).

MS (ESI) m/z 446.2 [M+H]+

Similarly Prepared were

Example 5B

N-Isopropyl-2-(6-((1S,4S)-5-methyl-2,5-diazabicyclo[2.2.1]heptan-2-yl)-4-oxo-2-phenylquinazolin-3(4H)-yl)acetamide (from EXAMPLE 2AAY)

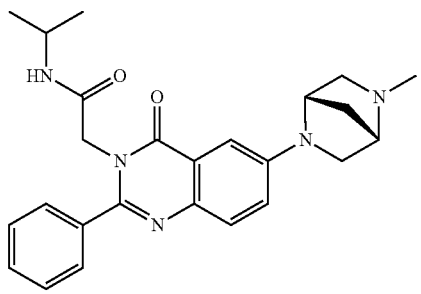 [SMILES: CC(C)NC(=O)Cn1c(-c2ccccc2)nc2ccc(N3C[C@@H]4C[C@H]3CN4C)cc2c1=O]

MS (ESI) m/z 432.2 [M+H]+

Example 5C 2-(2-Cyclopropyl-6-((1S,4S)-5-methyl-2,5-diazabicyclo[2.2.1]heptan-2-yl)-4-oxoquinazolin-3(4H)-yl)-N-isopropylacetamide (from Intermediate 12D)

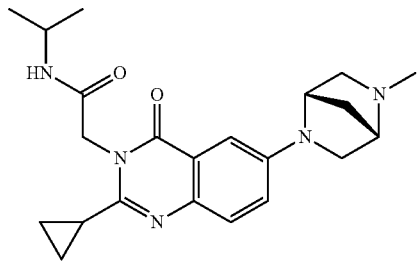 [SMILES: CC(C)NC(=O)Cn1c(C2CC2)nc2ccc(N3C[C@@H]4C[C@H]3CN4C)cc2c1=O]

MS (ESI) m/z 396.2 [M+H]+

Example 5D

2-Methyl-7-(5-methylhexahydropyrrolo[3,4-O]pyrrol-2(1H)-ylisoquinolin-1(2H)-one (from Example 4D)

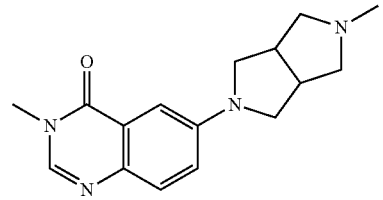

MS (ESI) m/z 284 [M+H]+

Example 6A 2-(6-(1,4-Diazabicyclo[3.2.2]nonan-4-yl)-2-(3-chlorophenyl)-4-oxoquinazolin-3(4H)-yl)-N,N-dimethylacetamide

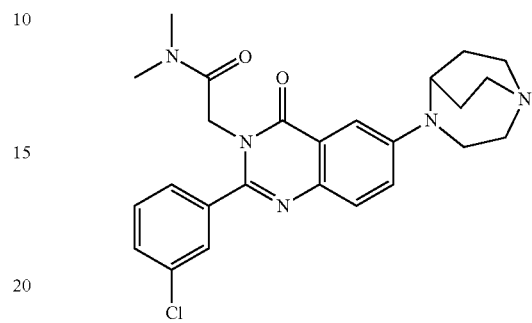

2-(6-(1,4-Diazabicyclo[3.2.2]nonan-4-yl)-2-(3-chlorophenyl)-4-oxoquinazolin-3(4H)-yl)acetic acid (Intermediate 11A) (49 mg, 0.11 mmol) and dimethylamine hydrochloride (18.2 mg, 0.22 mmol) were weighed into a round bottomed flask and dichloromethane (1 mL) added to form a suspension. Triethylamine (33.8 mg, 0.33 mmol) was added and the suspension stirred for 5 minutes before dropwise addition of 1-propanephosphonic acid cyclic anhydride as a 50% wt solution in ethyl acetate (107 mg, 0.17 mmol) and the resulting reaction mixture stirred for 2 hours. Reaction mixture was washed with sodium bicarbonate solution and the organics were separated using a hydrophobic frit. The solvent was removed under reduced pressure and then re-dissolved in methanol (1 mL) and purified by preparative-HPLC. To afford the title compound 2-(6-(1,4-diazabicyclo[3.2.2]nonan-4-yl)-2-(3-chlorophenyl)-4-oxoquinazolin-3(4H)-yl)-N,N-dimethylacetamide (5.4 mg, 0.012 mmol).

MS (ESI) m/z 466.2 [M+H]+

Similarly Prepared were

Example 6B 2-(6-(1,4-Diazabicyclo[3.2.2]nonan-4-yl)-2-ethyl-4-oxoquinazolin-3(4H)-yl)-N,N-dimethylacetamide (from Intermediate 14A)

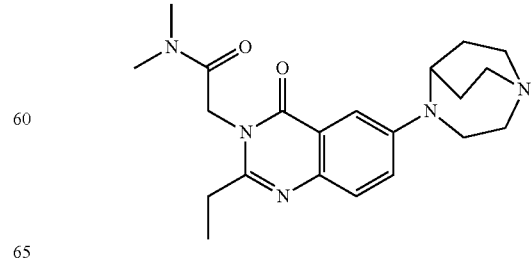

MS (ESI) m/z 384.2 [M+H]+

Example 6C 2-(6-(1,4-Diazabicyclo[3.2.2]nonan-4-yl)-2-ethyl-4-oxoquinazolin-3(4H)-yl)-N-isopropyl-N-methylacetamide (from Intermediate 14A)

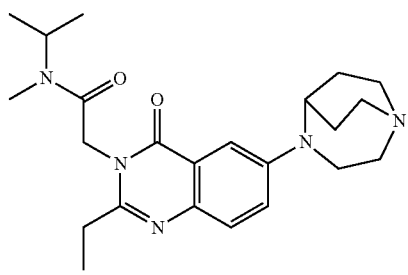 [SMILES: CCc1nc2ccc(N3CCN4CCC3CC4)cc2c(=O)n1CC(=O)N(C)C(C)C]

MS (ESI) m/z 412.2 [M+H]+

Example 7A 7-(1,4-Diazabicyclo[3.2.2]nonan-4-yl)-3-(3-chlorophenyl)-2-methylisoquinolin-1(2H)-one

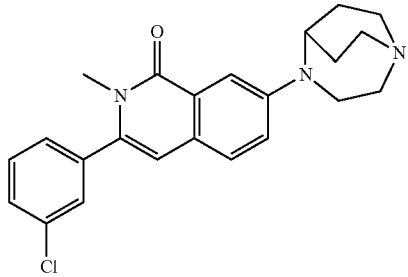 [SMILES: Cn1c(-c2cccc(Cl)c2)cc2ccc(N3CCN4CCC3CC4)cc2c1=O]

A mixture of 7-bromo-3-(3-chlorophenyl)-2-methylisoquinolin-1(2H)-one (Intermediate 24A) (50 mg, 0.143 mmol), 1,4-diazabicyclo[3.2.2]nonane (27.2 mg, 0.215 mmol), sodium t-butoxide (55.1 mg, 0.574 mmol), tris(dibenzylideneacetone)dipalladium(0) (13.13 mg, 0.014 mmol) and (+/−) BINAP (26.8 mg, 0.043 mmol) in degassed dioxane (1 mL) was heated to 85° C. under N₂ in a sealed vessel overnight. Reaction mixture allowed to cool to room temperature, diluted with water and the product extracted into ethyl acetate. Organics washed several times with water, dried (MgSO₄), filtered and then evaporated to dryness. The crude product was added to a silica gel column (25 g) and was eluted with 0-50% 2M ammonia in methanol in ethylacetate to afford 7-(1,4-diazabicyclo[3.2.2]nonan-4-yl)-3-(3-chlorophenyl)-2-methylisoquinolin-1(2H)-one (19.4 mg, 0.05 mmol).

MS (ESI) m/z 394 [M+H]+

Similarly Prepared were

Example 7B 7-(1,4-Diazabicyclo[3.2.2]nonan-4-yl)-3-(3-chlorophenyl)isoquinolin-1(2H)-one (from Intermediate 23A)

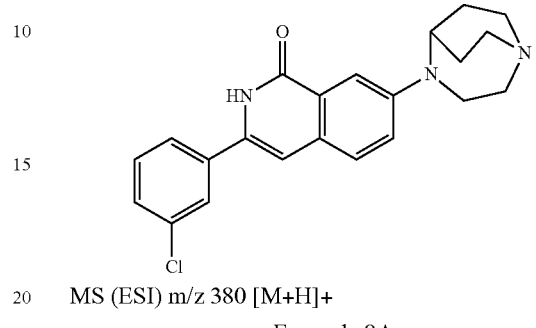

MS (ESI) m/z 380 [M+H]+

Example 8A 4-(2-(3-Chlorophenyl)-3-methyl-4-oxo-3,4-dihydroquinazolin-6-yl)-1-methyl-4-aza-1-azoniabicyclo[3.2.2]nonane iodide (from Example 2AL)

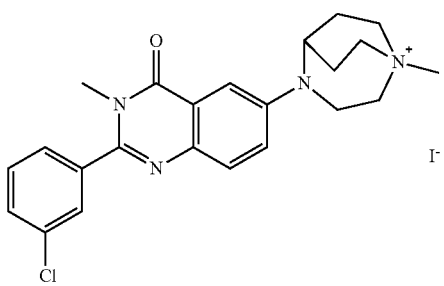 [SMILES: Cn1c(-c2cccc(Cl)c2)nc2ccc(N3CC[N+]4(C)CCC3CC4)cc2c1=O ; [I-]]

To a solution of iodomethane (0.18 g, 1.3 mmol) in THF (12 mL) was added 6-(1,4-diazabicyclo[3.2.2]nonan-4-yl)-2-(3-chlorophenyl)-3-methylquinazolin-4(3H)-one (Example 2AL) (0.5 g, 1.3 mmol) and reaction stirred for two days. The resultant precipitate was collected via filtration, triturated with minimum amount of methanol and dried to afford 4-(2-(3-chlorophenyl)-3-methyl-4-oxo-3,4-dihydroquinazolin-6-yl)-1-methyl-4-aza-1-azoniabicyclo[3.2.2]nonane iodide (0.44 g, 0.82 mmol).

MS (ESI) m/z 409.4 [M+H]+

Example 9A 4-(2-(3-Chlorophenyl)-3-methyl-4-oxo-3,4-dihydroquinazolin-6-yl)-1,4-diazabicyclo[3.2.2]nonane 1-oxide

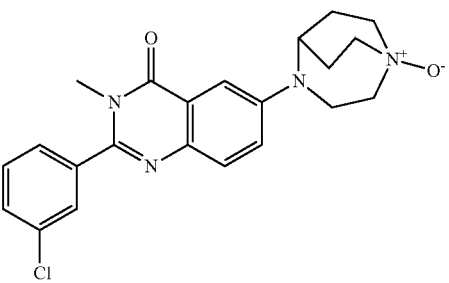 [SMILES: Cn1c(-c2cccc(Cl)c2)nc2ccc(N3CC[N+]4([O-])CCC3CC4)cc2c1=O]

To a solution of 6-(1,4-Diazabicyclo[3.2.2]nonan-4-yl)-2-(3-chlorophenyl)-3-methylquinazolin-4(3H)-one (400 mg, 1.013 mmol) (Example 2AL) in dichloromethane (12 mL) was added 3-chloroperbenzoic acid (250 mg, 1.013 mmol) and the reaction stirred at ambient temperature for 3 h. Sodium carbonate solution was added to neutralise the acid and the aqueous saturated with sodium chloride. The organic layer was separated off and chromatographed on 10 g silica, eluting with dichloromethane with 10% ammonia in methanol (1 M). To remove the remaining impurities the mixture was purified by acidic prep hplc, product passed through a carbonate on silica cartridge (2 g) to remove the acid to afford 4-(2-(3-chlorophenyl)-3-methyl-4-oxo-3,4-dihydroquinazolin-6-yl)-1,4-diazabicyclo[3.2.2]nonane 1-oxide (112 mg, 0.273 mmol).

MS (ESI) m/z 411.2 [M+H]+

Example 10A 6-((1S,4S)-5-Methyl-2,5-diazabicyclo[2.2.1]heptan-2-yl)quinazolin-4(3H)-one

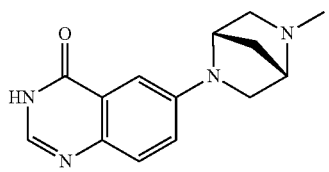 [SMILES: CN1C[C@@H]2C[C@H]1CN2c1ccc2nc[nH]c(=O)c2c1]

To a solution 2-amino-5-((1S,4S)-5-methyl-2,5-diazabicyclo[2.2.1]heptan-2-yl)benzamide (Intermediate 31D) (1 g, 3.83 mmol) in methanol (15 ml) was added trimethyl orthoformate (812 mg, 7.66 mmol) and ammonium acetate (0.60 g, 7.66 mmol). The vessel was sealed and the reaction heated at 120° C. for 4 hours. The methanol was then removed and the product chromatographed on silica elueting with 5% methanol in dichloromethane to afford 6-((1S,4S)-5-Methyl-2,5-diazabicyclo[2.2.1]heptan-2-yl)quinazolin-4(3H)-one (0.60 g, 2.33 mmol) as an off-white solid.

MS (ESI) m/z 257.0 [M+H]+

Example 11A 6-((1S,4S)-5-Methyl-2,5-diazabicyclo[2.2.1]heptan-2-yl)-3-((5-methylisoxazol-3-yl)methyl)quinazolin-4(3H)-one

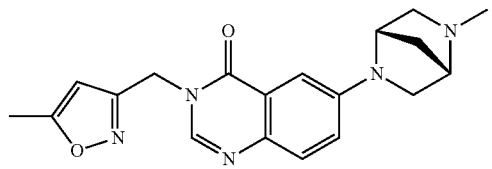

To a solution of 6-((1S,4S)-5-Methyl-2,5-diazabicyclo[2.2.1]heptan-2-yl)quinazolin-4(3H)-one (Example 10A) (150 mg, 0.583 mmol) in dimethylformamide was cooled to 0° C. added and sodium hydride (21 mg, 0.875 mmol) was added, after 5 minutes 3-bromomethyl-5-methylisoxazole (75 mg, 0.426 mmol) was added and the reaction stirred at room temp for 1 h. The reaction was quenched with ammonium chloride and the dimethylformamide evaporated off. The residue was dissolved in 10% methanol in dichloromethane and dried over sodium sulphate before evaporation to dryness. The product was purified by silica chromatography, elueting with 10% methanol in dichloromethane to afford 6-((1S,4S)-5-Methyl-2,5-diazabicyclo[2.2.1]heptan-2-yl)-3-((5-methylisoxazol-3-yl)methyl)quinazolin-4(3H)-one (0.10 g, 0.284 mmol).

MS (ESI) m/z 352.1 [M+H]+

Example 12A 6-(1,4-Diazabicyclo[3.2.2]nonan-4-yl)-3-methylthieno[2,3-d]pyrimidin-4(3H)-one

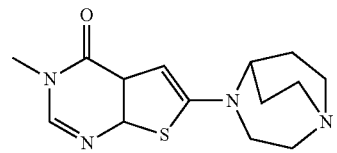 [SMILES: CN1C=NC2SC(N3CCN4CCC3CC4)=CC2C1=O]

A mixture of 6-bromo-3-methylthieno[2,3-d]pyrimidin-4(3H)-one (70 mg, 0.28 mmol), copper(I) iodide (13.6 mg, 0.071 mmol), L-proline (16.4 mg, 0.143 mmol), 1,4-diazabicyclo[3.2.2]nonane (54.1 mg, 0.428 mmol) and potassium phosphate (132 mg, 0.571 mmol) in DMSO (1 mL) was heated at 90° C. in a sealed vessel for 3 days. The reaction was acidified with acetic acid, diluted with methanol and purified on a scx cartridge (1 g), further purified by acid prep HPLC, passed through a scx cartridge (500 mg) and evaporated to dryness to afford 6-(1,4-Diazabicyclo[3.2.2]nonan-4-yl)-3-methylthieno[2,3-d]pyrimidin-4(3H)-one (1.8 mg, 0.006 mmol).

MS (ESI) m/z 291.0 [M+H]+

Example 13A 2-(3-Chlorophenyl)-3-methyl-6-(quinuclidin-3-yloxy)quinazolin-4(3H)-one

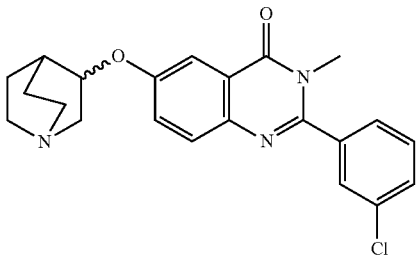 [SMILES: Cn1c(-c2cccc(Cl)c2)nc2ccc(OC3CN4CCC3CC4)cc2c1=O]

To a solution of 2-(3-chlorophenyl)-6-hydroxy-3-methylquinazolin-4(3H)-one (Intermediate 33A) (100 mg, 0.35 mmol), 3-quinuclidinol (44 mg, 0.35 mmol) and triphenylphosphine (137 mg, 0.35 mmol) in tetrahydrofuran (2 mL) was added dropwise diisopropyl azodicarboxylate (0.103 mL, 0.52 mmol). The reaction was stirred for 20 h. The mixture was purified by scx cartridge (1 g) followed by acidic prep hplc then scx (500 mg) to afford 2-(3-chlorophenyl)-3-methyl-6-(quinuclidin-3-yloxy)quinazolin-4(3H)-one (18 mg, 0.045 mmol).

MS (ESI) m/z 396.0 [M+H]+

143

Similarly Prepared were

Example 13B (S)-2-(3-Chlorophenyl)-3-methyl-6-(quinuclidin-3-yloxy)quinazolin-4(3H)-one (from Intermediate 33A)

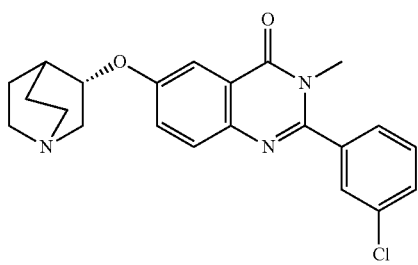 [SMILES: Cn1c(-c2cccc(Cl)c2)nc2ccc(O[C@@H]3CN4CCC3CC4)cc2c1=O]

MS (ESI) m/z 396.0 [M+H]$^+$

Example 13C (R)-2-(3-Chlorophenyl)-3-methyl-6-(quinuclidin-3-yloxy)quinazolin-4(3H)-one (from Intermediate 33A)

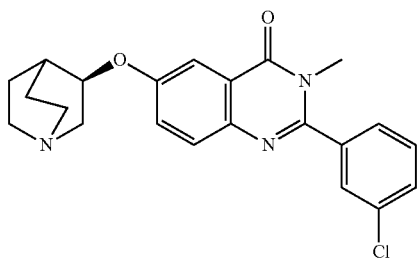 [SMILES: Cn1c(-c2cccc(Cl)c2)nc2ccc(O[C@H]3CN4CCC3CC4)cc2c1=O]

MS (ESI) m/z 396.0 [M+H]$^+$

Example 13D (S)-3-Ethyl-2-phenyl-6-(quinuclidin-3-yloxy)quinazolin-4(3H)-one (from Intermediate 33C)

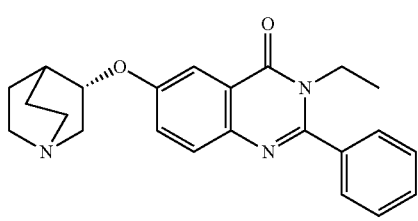 [SMILES: CCn1c(-c2ccccc2)nc2ccc(O[C@@H]3CN4CCC3CC4)cc2c1=O]

MS (ESI) m/z 376.2 [M+H]$^+$

144

Example 13E (R)-3-Ethyl-2-phenyl-6-(quinuclidin-3-yloxy)quinazolin-4(3H)-one (from Intermediate 33C)

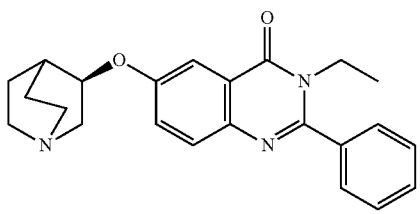 [SMILES: CCn1c(-c2ccccc2)nc2ccc(O[C@H]3CN4CCC3CC4)cc2c1=O]

MS (ESI) m/z 376.2 [M+H]$^+$

Example 13F (S)-3-Methyl-6-(quinuclidin-3-yloxy)quinazolin-4(3H)-one (from Intermediate 33B)

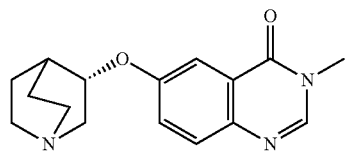 [SMILES: Cn1cnc2ccc(O[C@@H]3CN4CCC3CC4)cc2c1=O]

MS (ESI) m/z 286.2 [M+H]$^+$

Example 14

Nicotinic Acetylcholine α7 Receptor FLIPR Assay

Test compounds were prepared as a stock solution in 100% dimethylsulfoxide (DMSO) and then further diluted in assay buffer so that the final concentration of DMSO in the assay was 1%. Each compound was tested for activity over 10 concentrations at half log intervals (ranging 300 pM-10 µM).

HEK 293 cells stably co-expressing the human nicotinic receptor α7 subunit with human RIC3 (HEK α7/RIC3) were grown in MEM+glutamax (Invitrogen Corp., Paisley, UK) supplemented with 10% FetalClone II (Hyclone, Thermo Scientific, Logan, Utah, USA), non-essential amino acids, 1 mg/ml G418 (Invitrogen Corp., Paisley, UK), 0.5 mg/ml zeocin (Invitrogen Corp., Carlsbad, Calif., USA) at 37° C., 5% $CO_2$ and 100% relative humidity. 24 hours prior to the assay, cells were seeded into 384 well black walled plates with clear bottoms, at a density of 5000 cells per well, in growth medium containing no antibiotic selection. Assay plates were pre-treated with Matrigel (BD Biosciences, California, USA).

On the day of the assay, the growth medium was aspirated and replaced with 25 µl of Fluo3-AM (10 µM; Invitrogen Molecular Probes, Eugene, Oreg., USA) prepared in α7 assay buffer (1×HBSS [Invitrogen Corp., Paisley, UK], 20 mM HEPES; pH 7.4, 200 mM probenecid) and incubated for 1 hour at 37° C. The dye was then aspirated and the cells washed with 50 µl of assay buffer. The cells were transferred to the FLIPR 3 (Molecular Devices Corp., Sunnyvale, Calif. USA) before being incubated with 25 µl of the selective α7 receptor positive allosteric modulator PNU 120596 (commercially available-7 µM in assay buffer) for 2 minutes at room temperature. 12.5 µl of the test compound was added and agonist evoked responses, mediated by nicotinic acetylcholine α7 receptors, were measured as a function of the change in fluorescence of the Fluo3-AM dye.

Typical $EC_{50}$ values measured in the in vitro assay described above for the compounds of the invention are 100 μM or less. For some compounds of the invention the $EC_{50}$ was found to be below 10 μM. For many compounds of the invention the $EC_{50}$ was found to be below 100 nM.

The invention claimed is:

1. A heterocyclic derivative of formula I

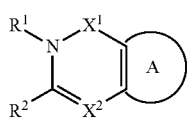

formula I wherein $R^1$ is H, $C_{1-8}$alkyl, $C_{2-8}$alkenyl, $C_{2-8}$alkynyl, $C_{3-8}$cycloalkyl, $C_{3-8}$cycloalkyl$C_{1-2}$alkyl, Z—$C_{1-2}$alkyl or a 4-8 membered heterocyclyl comprising one or more heteroatomic moiety independently selected from O, S, SO and $SO_2$, wherein Z is a 5-6 membered heteroaryl comprising one or more heteroatom independently selected from O, N, and S, said $C_{1-8}$alkyl, $C_{3-8}$cycloalkyl, $C_{3-8}$cycloalkyl$C_{1-2}$alkyl, 5-6 membered heteroaryl and 4-8 membered heterocyclyl being optionally substituted with one or more substituent independently selected from halogen, hydroxyl, $C_{1-6}$alkoxyl, $CONR^3R^4$, $SO_2NR^5R^6$ and $CO_2C_{1-6}$alkyl;

$R^2$ is H, $C_{1-8}$alkyl, $C_{3-8}$cycloalkyl or $C_{3-8}$cycloalkyl$C_{1-2}$alkyl, said $C_{1-8}$alkyl, $C_{3-8}$cycloalkyl and $C_{3-8}$cycloalkyl$C_{1-2}$alkyl being optionally substituted with one or more substituent independently selected from halogen, hydroxyl and methoxy or $R^2$ is $C_{6-10}$aryl optionally substituted with one or more substituent independently selected from halogen, hydroxy, cyano, $C_{1-8}$alkyl, $C_{3-8}$cycloalkyl, $C_{1-6}$alkyloxy and $C_{3-6}$cycloalkyloxy, said $C_{1-8}$alkyl, $C_{3-8}$cycloalkyl, $C_{1-6}$alkyloxy and $C_{3-6}$cycloalkyloxy being optionally substituted with one or more halogens or $R^2$ is a 5-10 membered heteroaryl ring system comprising a heteroatom selected from N, O and S and optionally substituted with methyl, $C_{1-6}$alkyloxy, halogen or cyano;

$R^3$ and $R^4$ are independently H or $C_{1-6}$alkyl or $R^3$ and $R^4$ together with the N to which they are bonded form a 4-7 membered heterocyclic ring optionally comprising a further heteroatomic moiety selected from 0, S, SO and $SO_2$, said $C_{1-6}$alkyl and 4-7 membered heterocyclic ring being optionally substituted with one or more halogens;

$R^5$ and $R^6$ are independently H or $C_{1-6}$alkyl or $R^5$ and $R^6$ together with the N to which they are bonded form a 4-7 membered heterocyclic ring optionally comprising a further heteroatomic moiety selected from 0, S, SO and $SO_2$, said $C_{1-6}$alkyl and 4-7 membered heterocyclic ring being optionally substituted with one or more halogens;

$X^1$ is CO;

$X^2$ is N;

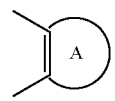

is a moiety selected from:

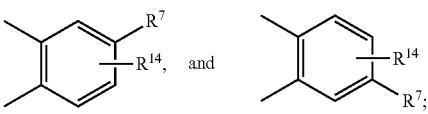

$R^7$ is $(Y)_mR^8$, wherein

Y is O, $NR^9$ or $CR^{10}R^{11}$, m is 0 or 1, and $R^8$ is a moiety selected from the group consisting of:

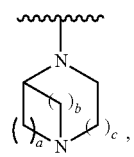

wherein a, b and c are independently 1 or 2;

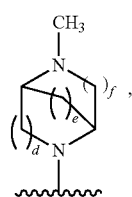

wherein d, e and f are independently 1 or 2;

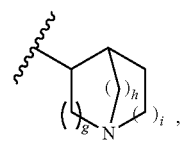

wherein g, h and i are independently 1 or 2;

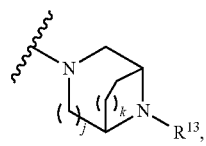

wherein j, and k are independently 1 or 2;

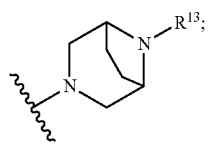

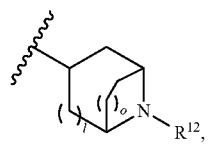

wherein l, and o are independently 1 or 2; and

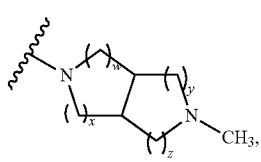

wherein w, x, y and z are independently 1 or 2;

R⁹ is H or $C_{1-6}$alkyl;

R¹⁰ and R¹¹ are independently H or $C_{1-6}$alkyl;

R¹² and R¹³ are independently H, $C_{1-6}$alkyl or oxo;

R¹⁴ is a further optional substituent selected from methyl, halogen and cyano;

n is 0 or 1, and p is 0 or 1, with the proviso that when R⁷ is 1,4-diazabicyclo[3.2.2]non-4-yl or octahydropyrrolo[1,2-a]pyrazin-2-yl, one or both of R³ and R⁴ cannot be H, or a pharmaceutically acceptable salt thereof.

2. The heterocyclic derivative according to claim 1 or a pharmaceutically acceptable salt thereof, wherein R¹ is H, methyl, ethyl, propyl or isopropyl, optionally substituted with hydroxyl or methoxyl.

3. The heterocyclic derivative according to claim 1 or a pharmaceutically acceptable salt thereof, wherein R¹ is H or methyl.

4. The heterocyclic derivative according to claim 1 or a pharmaceutically acceptable salt thereof, wherein R² is H, methyl, ethyl, isopropyl, t-butyl, cyclopropyl, cyclobutyl, cyclopentyl or cyclohexyl.

5. The heterocyclic derivative according to claim 1 or a pharmaceutically acceptable salt thereof, wherein R² is phenyl optionally substituted with one or two substituents selected from chloro, fluoro, methyl, methoxyl and cyano.

6. The heterocyclic derivative according to claim 1 or a pharmaceutically acceptable salt thereof, wherein R² is pyridyl, thiazolyl or furanyl optionally substituted with methyl or halogen.

7. The heterocyclic derivative according to claim 1 or a pharmaceutically acceptable salt thereof, wherein R⁷ is selected from the group consisting of:

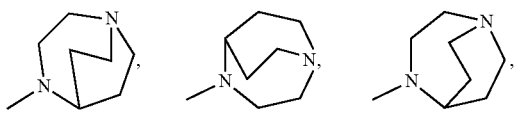

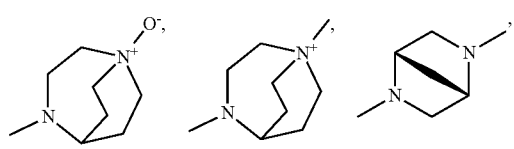

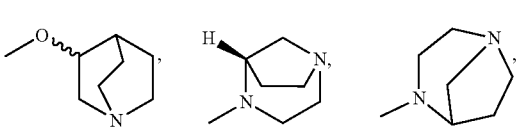

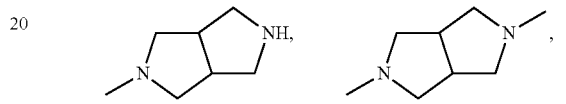

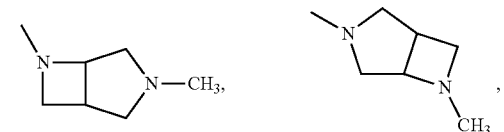

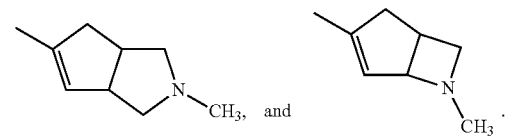

8. The heterocyclic derivative according to claim 7 or a pharmaceutically acceptable salt thereof, wherein a is 2, b is 2 and c is 1.

9. The heterocyclic derivative according to claim 1 or a pharmaceutically acceptable salt thereof, wherein R⁷ is

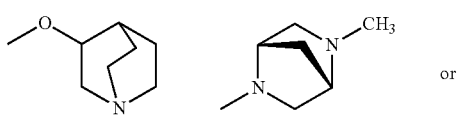

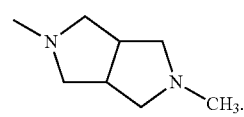

10. A heterocyclic derivative selected from the group consisting of:

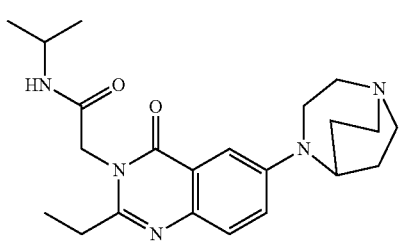

149
-continued
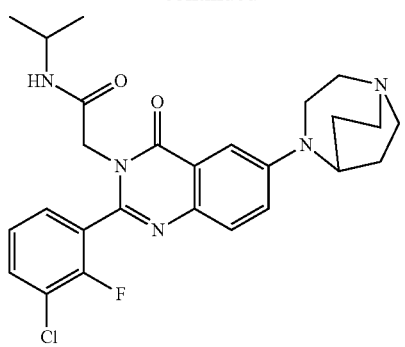
150
-continued
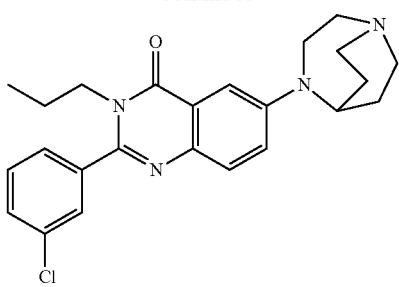
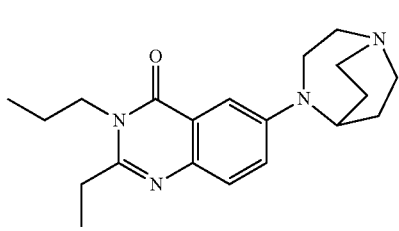
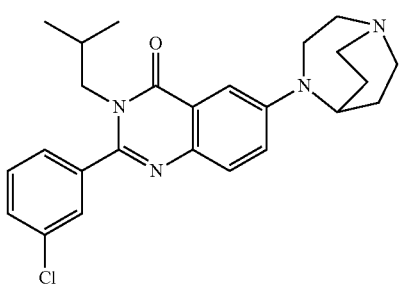
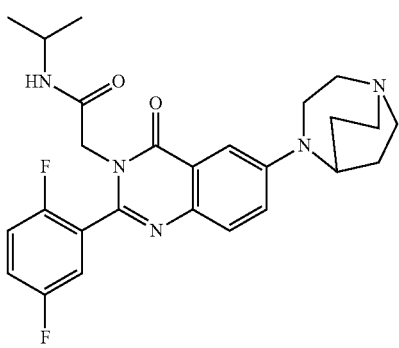
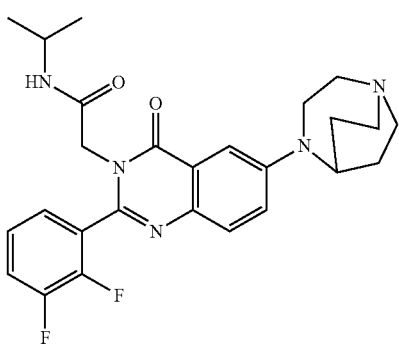

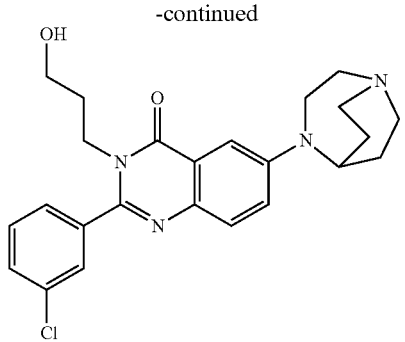
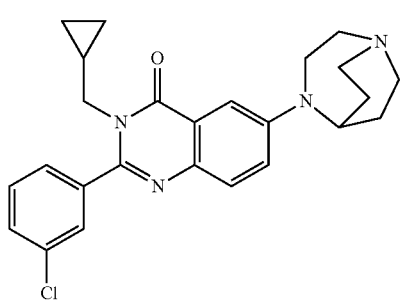
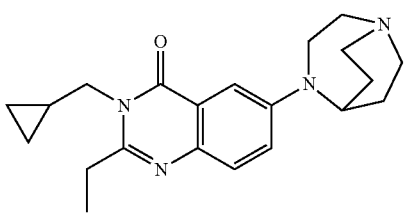
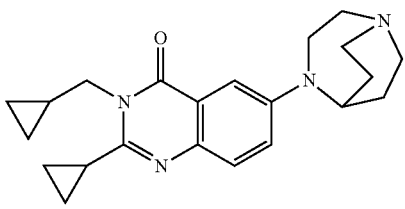
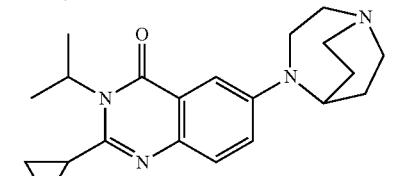
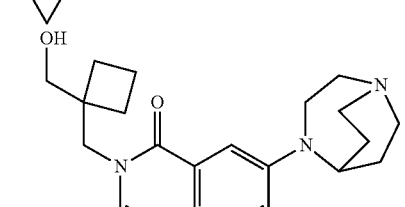
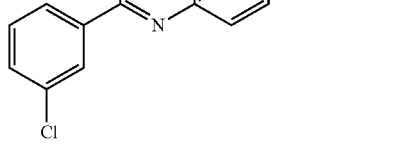
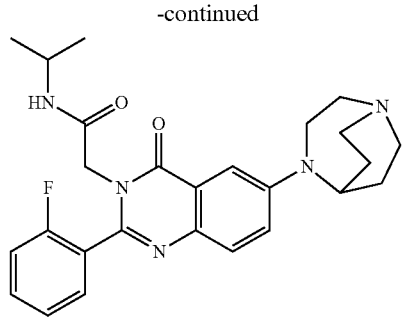
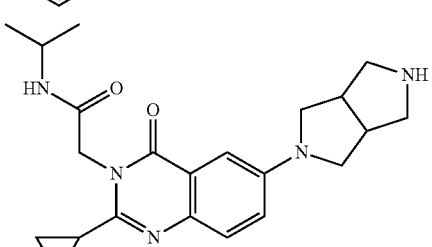
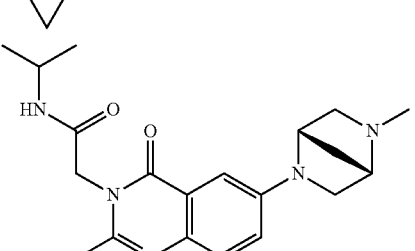
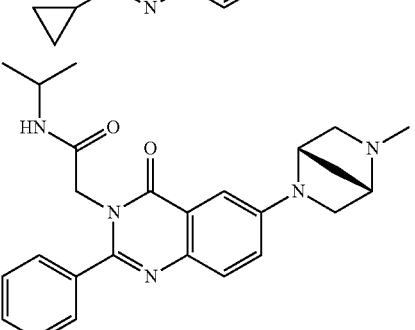
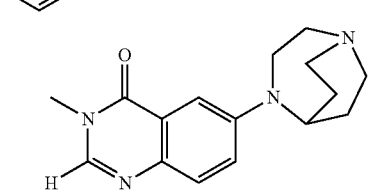
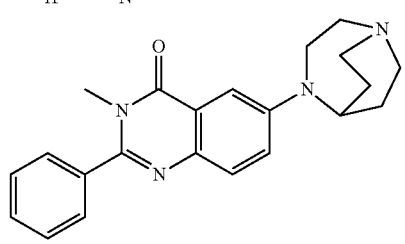
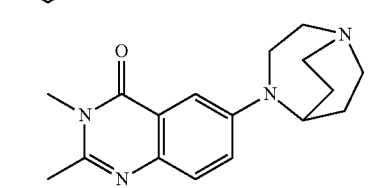

| 153 -continued | 154 -continued |
|---|---|
| 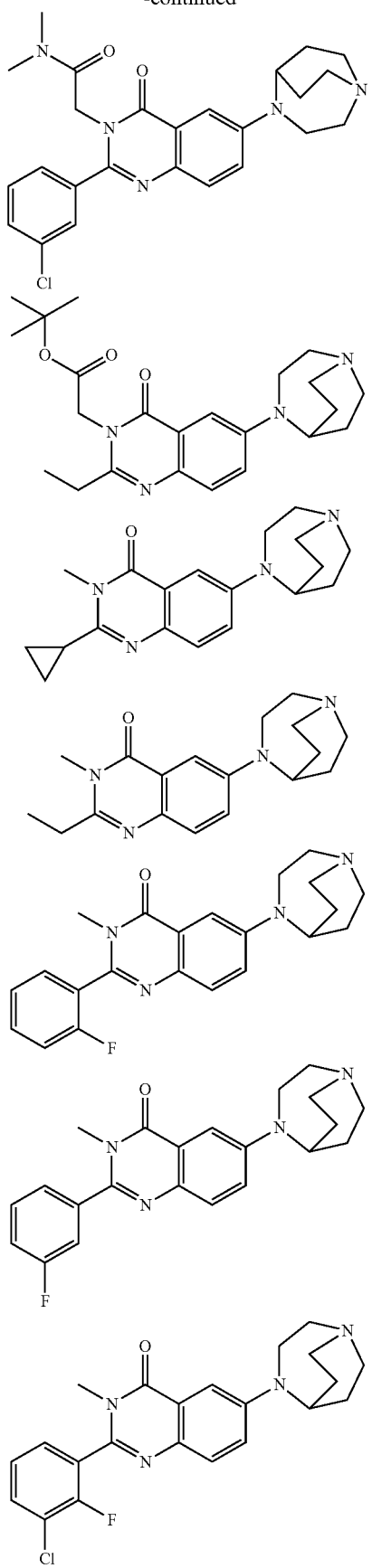 | 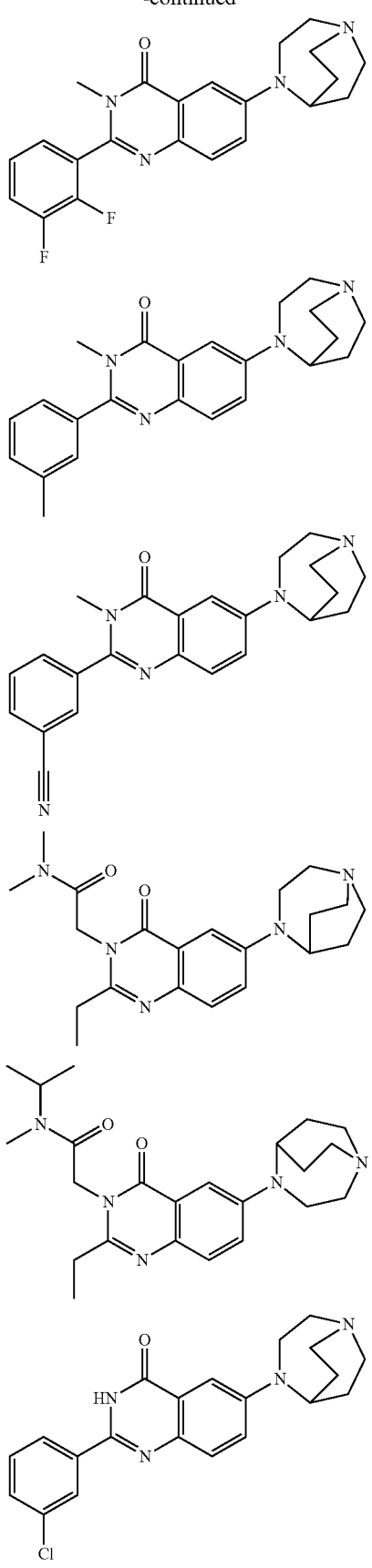 |

155
-continued
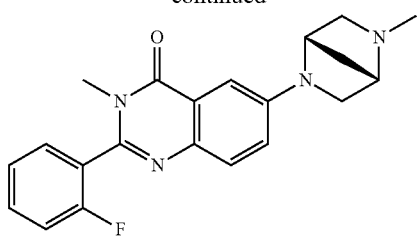
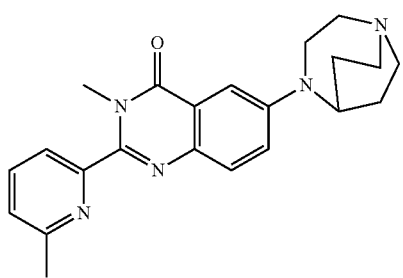
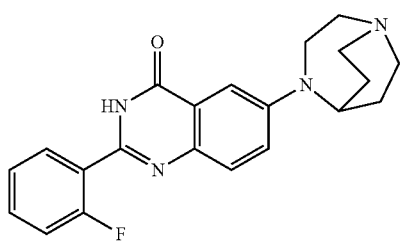
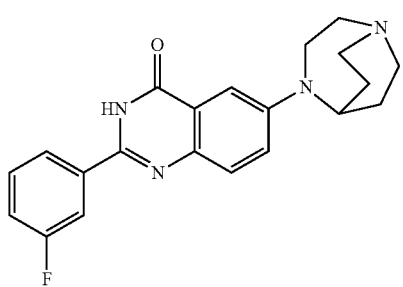
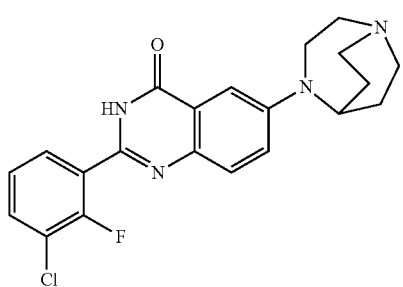
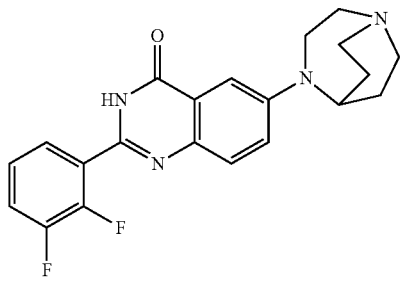
156
-continued
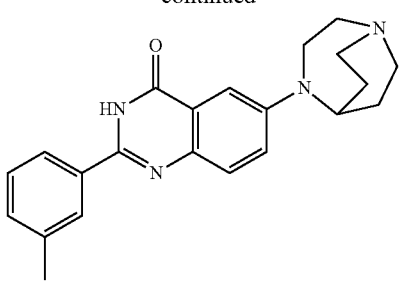
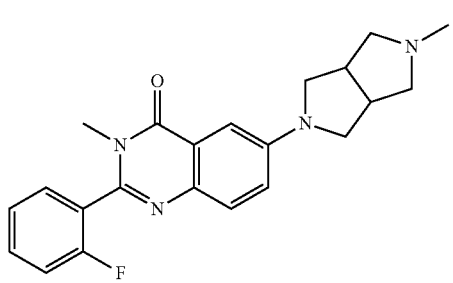
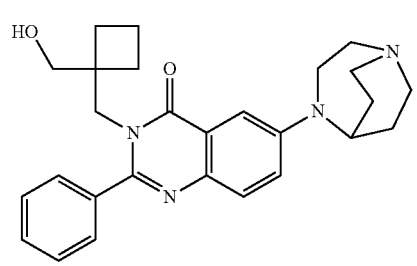
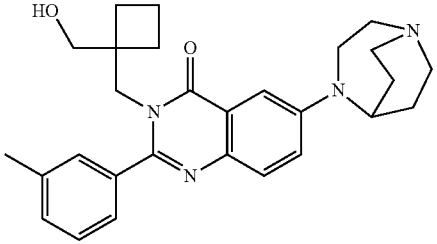
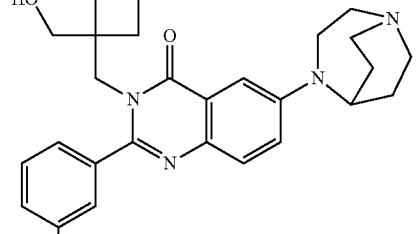
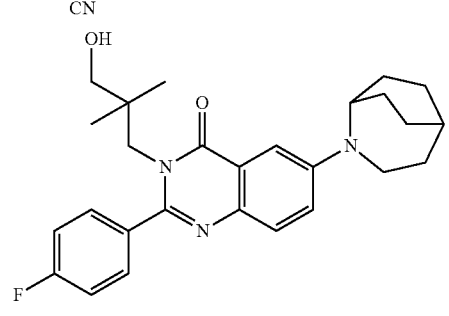

157
-continued
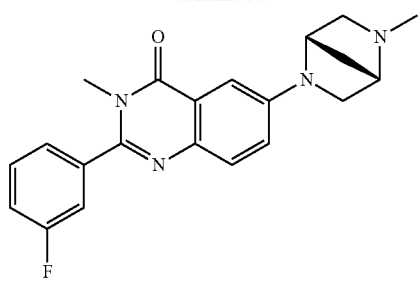
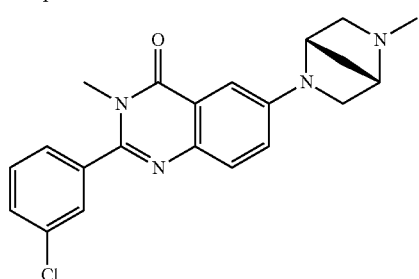
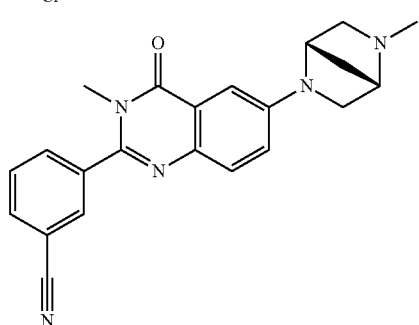
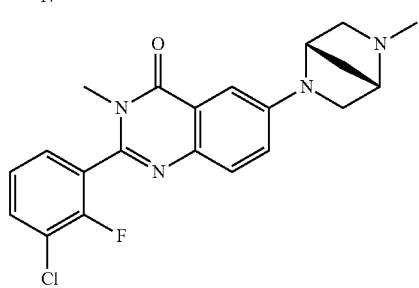
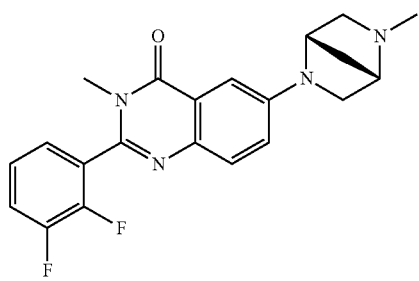
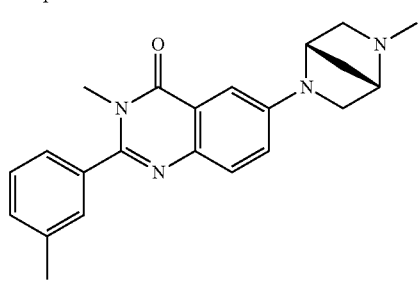
158
-continued
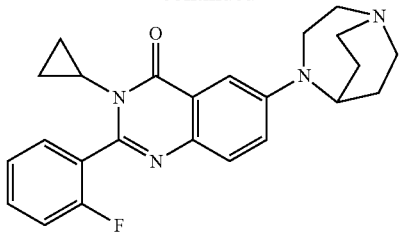
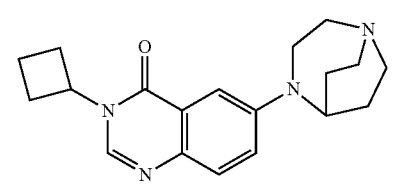
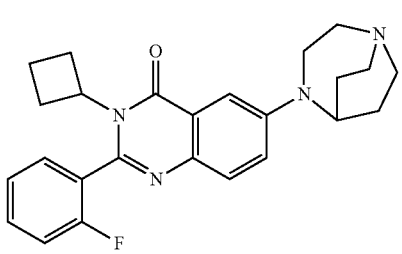
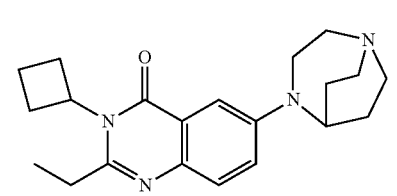
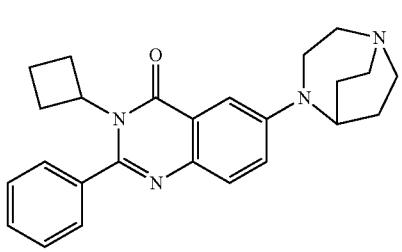
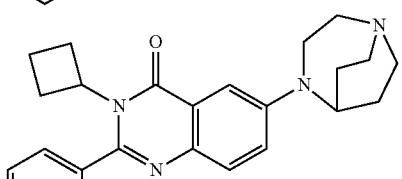
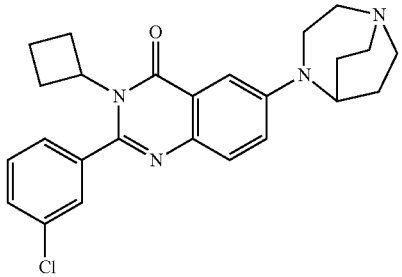

159
-continued
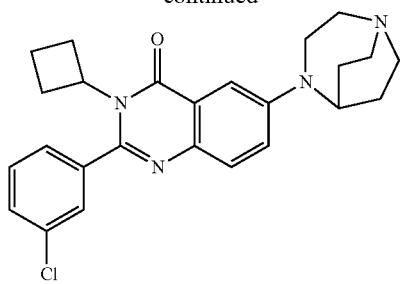
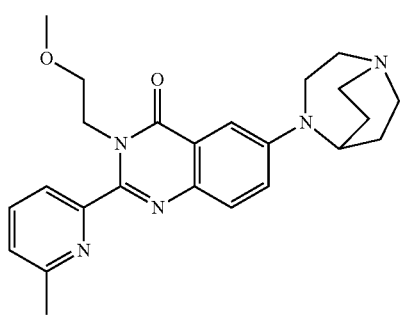
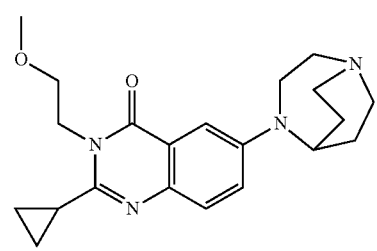
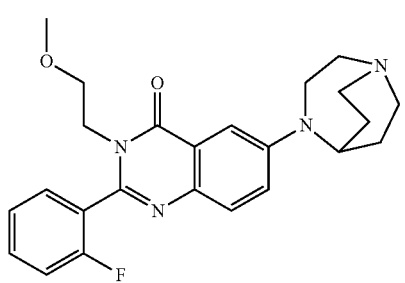
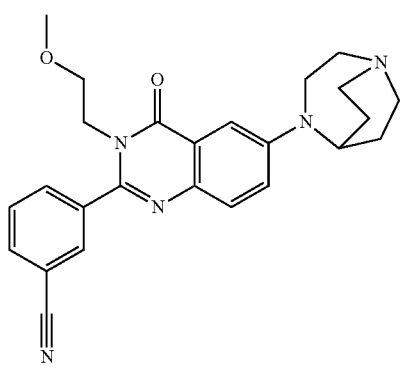
160
-continued
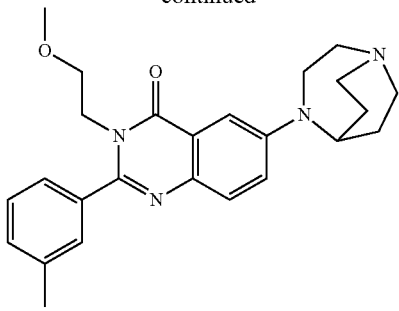
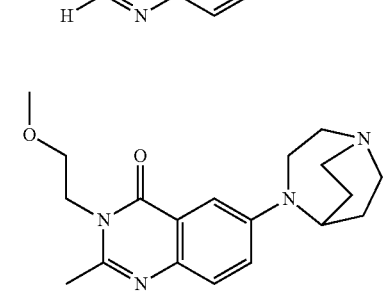
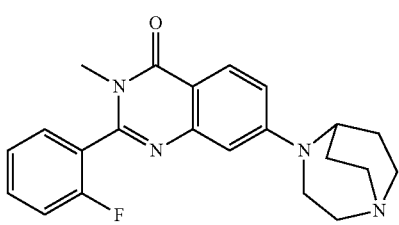
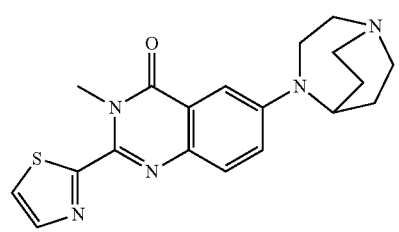
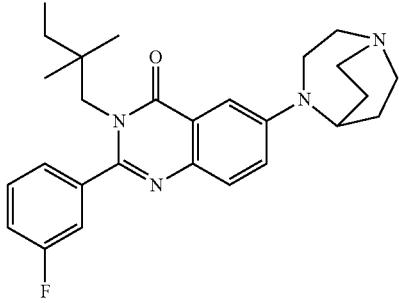

161
-continued
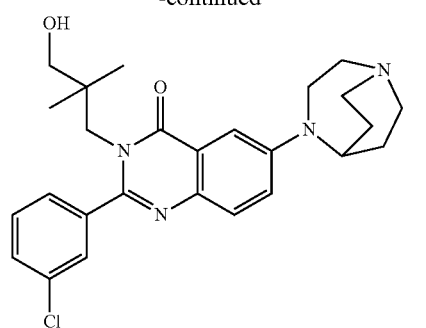
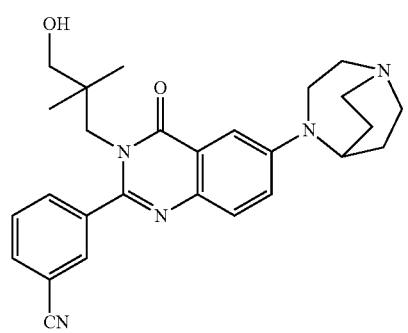
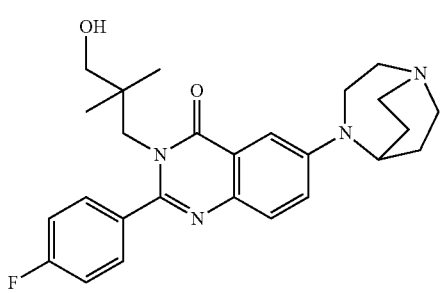
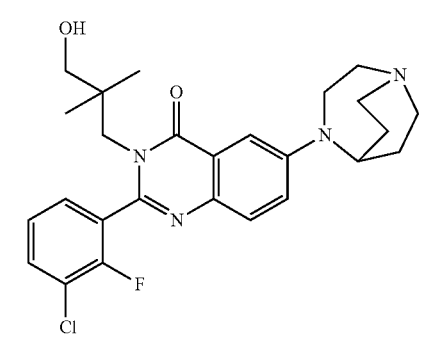
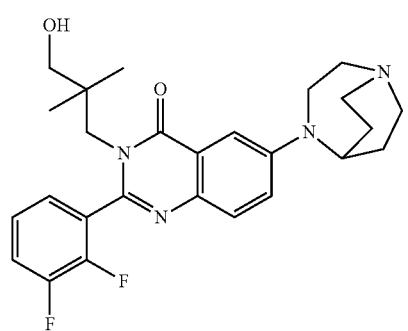
162
-continued
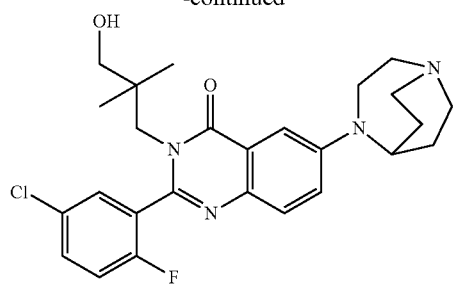
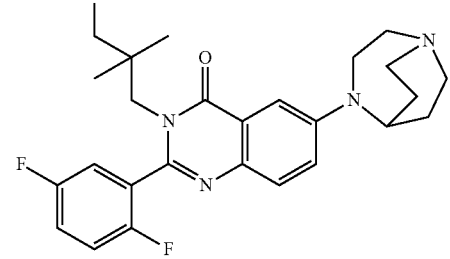
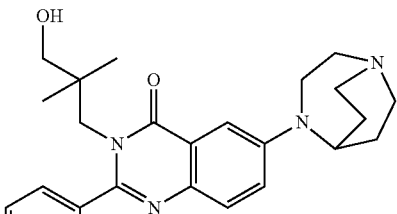
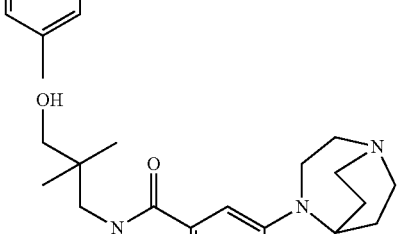
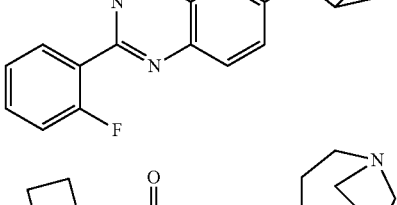
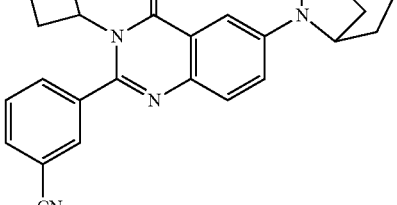
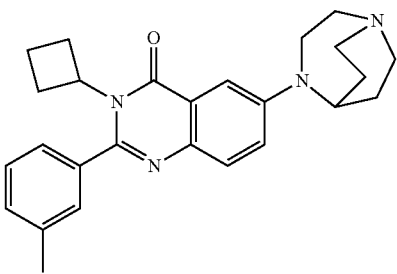

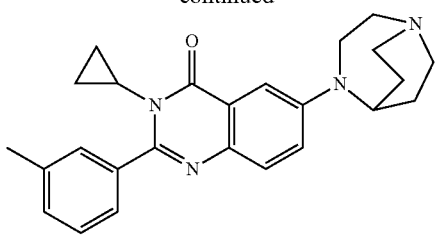
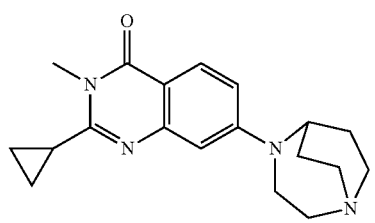
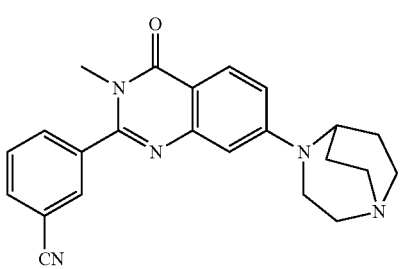
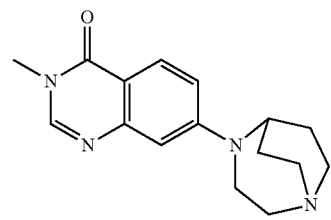
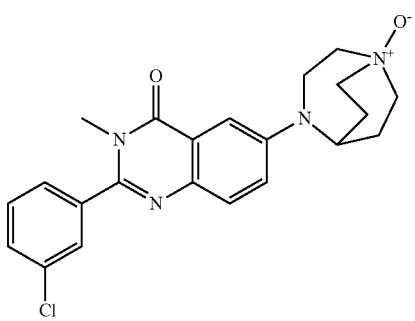
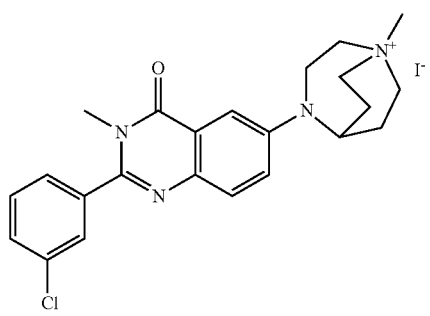
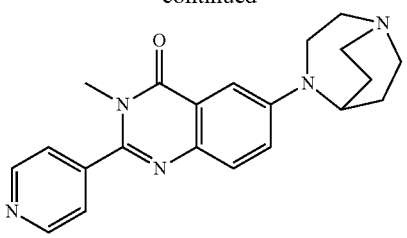
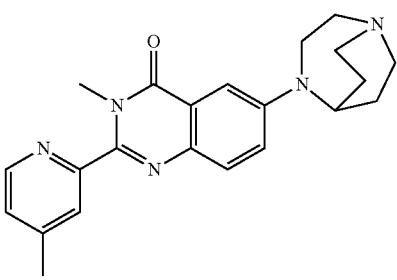
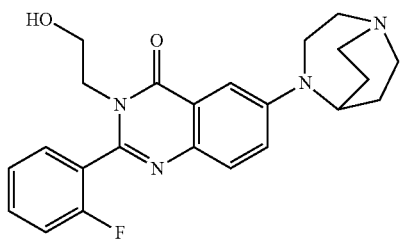
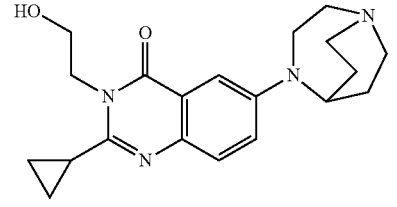
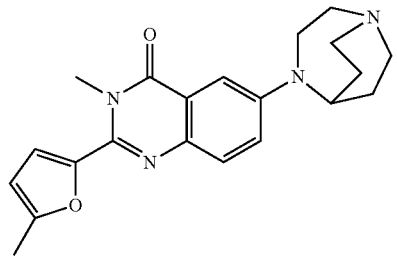
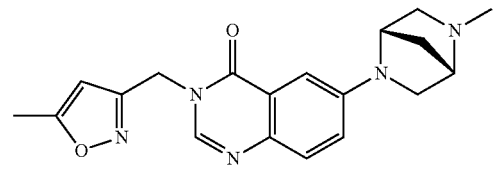
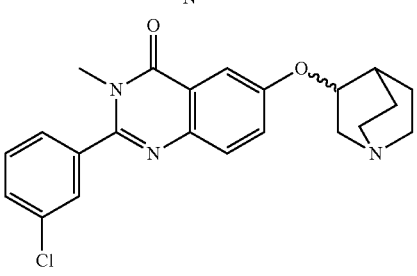

-continued

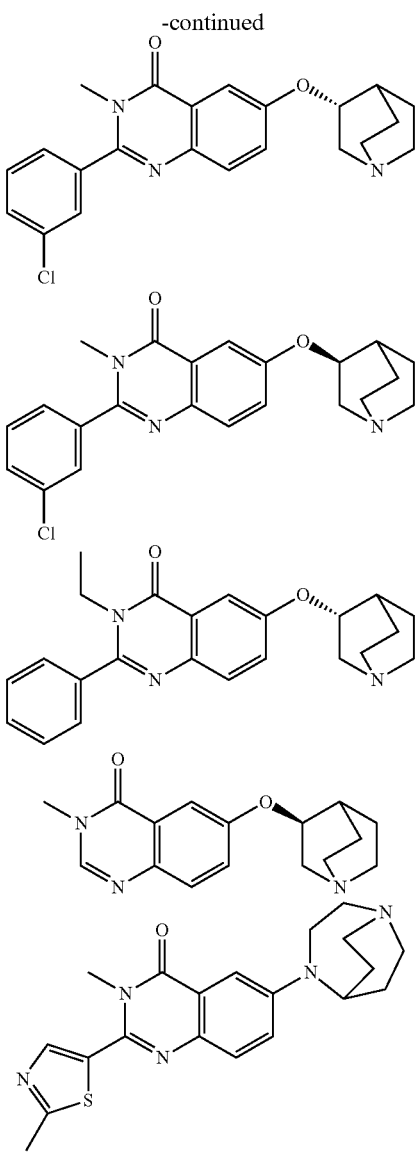

-continued

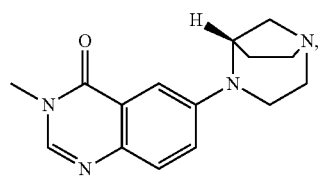

or a pharmaceutically acceptable salt thereof.

11. A pharmaceutical composition comprising a heterocyclic derivative according to claim 1 or a pharmaceutically acceptable salt thereof in admixture with one or more pharmaceutically acceptable excipients.

12. A method for treating schizophrenia in a patient in need thereof, the method comprising administering to the patient a therapeutically effective amount of a heterocyclic derivative according to claim 1 or a pharmaceutically acceptable salt thereof.

13. A method for treating Alzheimer's Disease in a patient in need thereof, the method comprising administering to the patient a therapeutically effective amount of a heterocyclic derivative according to claim 1 or a pharmaceutically acceptable salt thereof.

14. A pharmaceutical composition comprising a heterocyclic derivative according to claim 10 or a pharmaceutically acceptable salt thereof in admixture with one or more pharmaceutically acceptable excipients.

15. A method for treating schizophrenia in a patient in need thereof, the method comprising administering to the patient a therapeutically effective amount of a heterocyclic derivative according to claim 10 or a pharmaceutically acceptable salt thereof.

16. A method for treating Alzheimer's Disease in a patient in need thereof, the method comprising administering to the patient a therapeutically effective amount of a heterocyclic derivative according to claim 10 or a pharmaceutically acceptable salt thereof.

* * * * *